United States Patent
Lim et al.

(10) Patent No.: US 12,195,469 B2
(45) Date of Patent: Jan. 14, 2025

(54) COMPOUNDS HAVING PDE9A INHIBITORY ACTIVITY, AND PHARMACEUTICAL USES THEREOF

(71) Applicant: KOREA RESEARCH INSTITUTE OF CHEMICAL TECHNOLOGY, Daejeon (KR)

(72) Inventors: Chae Jo Lim, Daejeon (KR); Kwang-Seok Oh, Daejeon (KR); Jeong Hyun Lee, Daejeon (KR); Kyu Yang Yi, Daejeon (KR); Nack Jeong Kim, Daejeon (KR); Byung Ho Lee, Daejeon (KR); Ho Won Seo, Daejeon (KR); Soo Hee Kim, Daejeon (KR); Junyoung Choi, Daejeon (KR); Mi Young Lee, Daejeon (KR); Ju Hee Lee, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 816 days.

(21) Appl. No.: 17/311,287

(22) PCT Filed: Dec. 5, 2019

(86) PCT No.: PCT/KR2019/017127
§ 371 (c)(1),
(2) Date: Jun. 4, 2021

(87) PCT Pub. No.: WO2020/116971
PCT Pub. Date: Jun. 11, 2020

(65) Prior Publication Data
US 2022/0024932 A1     Jan. 27, 2022

(30) Foreign Application Priority Data
Dec. 6, 2018 (KR) .................. 10-2018-0156031

(51) Int. Cl.
C07D 487/04 (2006.01)
(52) U.S. Cl.
CPC .................. C07D 487/04 (2013.01)
(58) Field of Classification Search
CPC .................................. C07D 487/04
See application file for complete search history.

(56) References Cited

U.S. PATENT DOCUMENTS 8,236,809 B2    8/2012   Tegtmeier et al.

FOREIGN PATENT DOCUMENTS

| CN | 108101910 A | 6/2018 |
|---|---|---|
| JP | 2012/110441 A1 | 8/2012 |
| KR | 10-2007-0043938 A | 4/2007 |
| KR | 10-2013-0112248 A | 10/2013 |
| WO | 2009-062118 A2 | 5/2009 |
| WO | 2012/020022 A1 | 2/2012 |
| WO | 2012/110441 A1 | 8/2012 |
| WO | 2016/192083 A1 | 12/2016 |
| WO | 2017-123766 A1 | 7/2017 |

OTHER PUBLICATIONS

Zheng, An overview of phosphodiesterase 9 inhibitors: Insights from skeletal structure, pharmacophores, and therapeutic potential, 2023, European Journal of Medicinal Chemistry, vol. 259, p. 1-15 (Year: 2023).*
Al-Chalabi, Preventing neurodegenerative disease, 2021, Brain, vol. 144, p. 1279-1280. (Year: 2021).*
RN 2183345-16-4, Chemical Abstract compound STN express, Mar. 3, 2018, 5 pages.
Antonio Valencia et al., "Elevated NADPH oxidase activity contributes to oxidative stress and cell death in Huntington's disease", Human molecular genetics, 2013, vol. 22, No. 6, pp. 1112-1131.
International Search Report issued Mar. 20, 2020, corresponding to International Application No. PCT/KR2019/017127.
Written Opinion issued Mar. 20, 2020, corresponding to International Application No. PCT/KR2019/017127.
Zhang Chen et al., "Discovery of novel PED9A inhibitors with antioxidant activities for treatment of Alzehimer's disease" Journal of Enzyme Inhibition and Medicinal Chemistry, vol. 33, No. 1, Dec. 22, 2017, pp. 260-270.
Verhoest Patrick R. et al., "Design and Discovery of Discovery of 6~", Journal of Medicinal Chemistray, vol. 55, No. 21, Jul. 10, 2012, pp. 9045-9054.

* cited by examiner

Primary Examiner — Joseph K Mckane
Assistant Examiner — Karen Cheng
(74) Attorney, Agent, or Firm — Hauptman Ham, LLP

(57) ABSTRACT

The present invention provides a compound having a specific chemical structure and having PDE9A inhibitory activity, or a pharmaceutically acceptable salt thereof. The present invention provides a composition containing the compound or a pharmaceutically acceptable salt thereof. The present invention provides a pharmaceutical use, for treating or preventing PDE9A-related diseases, of the compound according to the present invention, a salt thereof, and a composition containing the compound or salt. The present invention also provides a method for treating or preventing PDE9A-related diseases, the method comprising administering an effective amount of the compound according to the present invention, a salt thereof, or a composition containing the compound or salt to a subject in need of treatment.

5 Claims, No Drawings

COMPOUNDS HAVING PDE9A INHIBITORY ACTIVITY, AND PHARMACEUTICAL USES THEREOF

CROSS-REFERENCE TO RELATED APPLICATION

This present application is a national stage filing under 35 U.S.C § 371 of PCT application number PCT/KR2019/017127 filed on Dec. 5, 2019 which is based upon and claims the benefit of priority to Korean Patent Application No. 10-2018-0156031 filed Dec. 6, 2018 in the Korean Intellectual Property Office. The disclosures of the above-listed applications are hereby incorporated by reference herein in their entireties.

The present invention relates to a group of compounds having a specific structure and excellent PDE9A inhibitory activity. The invention also relates to pharmaceutical compositions comprising such compounds. The present invention relates to a useful method for treating diseases related to PDE9A using these compounds. That is, the present invention relates to a medical use of the compounds according to the present invention for treating or preventing PDE9A-related diseases.

BACKGROUND ART

Phosphodiesterase 9A (PDE9A) is mainly expressed in the brain, particularly in the neocortex of the cerebellum and hippocampus, and is known to be associated with the regulation of cGMP concentration, i.e. glutamate-related signals through memory and learning. Therefore, inhibition of phosphodiesterase 9A is known to be useful in the treatment of Alzheimer's disease, CNS disorders, or cognitive disorders caused by various neurodegenerative processes. Therefore, it is recognized as a useful pharmacological target for the treatment or alleviation of cognitive disorders such as dementia with frontal lobe degeneration including Lewy body dementia, Pick's syndrome, Parkinson's disease and Alzheimer's disease with learning and memory problems.

Furthermore, in addition to cranial nerve diseases, overexpression of phosphodiesterase 9A has recently been found in patients with heart disease, especially in patients with cardiac output-preserving heart failure, and overexpression of phosphodiesterase 9A has been observed in animal models that induce pathological conditions of the heart. In addition, the effects of improving cardiac function and relieving myocardial hypertrophy through the inhibition of phosphodiesterase 9A have been reported, and thus, it is attracting attention recently as a useful pharmacological target for patients with cardiovascular disease, especially those with cardiac output-preserving heart failure.

DISCLOSURE

Technical Problem

Accordingly, a problem to be solved by the present invention is to provide a compound having PDE9A inhibitory activity, a pharmaceutical composition comprising the compound as an active ingredient, and a medical use for the treatment or prevention of PDE9A-related diseases thereof.

Another problem to be solved by the present invention is to provide a method for treating or alleviating PDE9A-related diseases, characterized in that it inhibits PDE9A activity, and it comprises administering the compound according to the present invention to a patient in need of treatment, improvement or prevention of PDE9A-related diseases.

Technical Solution

In order to solve the above problem, one embodiment of the present invention provides a compound represented by the following Chemical Formula 1 or a pharmaceutically acceptable salt thereof.

[Chemical Formula 1]

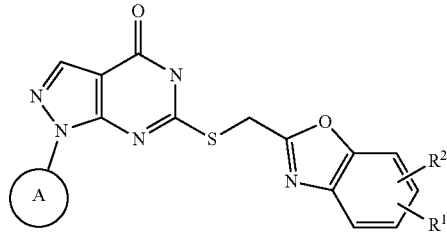

In the Chemical Formula 1,

A is phenyl unsubstituted or substituted with one or more halogens, $C_{1-5}$ straight or branched alkyl unsubstituted or substituted with one or more halogens, 3 to 6 membered cycloalkyl unsubstituted or substituted with one or more halogens, or 3 to 6 membered heterocycloalkyl unsubstituted or substituted with one or more halogens, $R^1$ and $R^2$ are each independently —H, halogen, —$NO_2$, —$CF_3$, phenyl unsubstituted or substituted with one or more halogens, $C_{1-5}$ straight or branched alkyl unsubstituted or substituted with one or more halogens, or $C_{1-5}$ straight or branched alkoxy unsubstituted or substituted with one or more halogens.

As used herein, the terms "halogen" and "halo" mean fluorine, chlorine, bromine or iodine.

As used herein, the term "cycloalkyl" means a monocyclic or polycyclic saturated ring having carbon and hydrogen atoms and having no carbon-carbon multiple bonds. Examples of cycloalkyl groups include, but are not limited to, ($C_3$-$C_6$)cycloalkyl groups, including cyclopropyl, cyclobutyl, cyclopentyl, cyclohexyl, and cycloheptyl. A cycloalkyl group can be unsubstituted or optionally substituted. In one embodiment, the cycloalkyl group is a monocyclic ring or bicyclic ring.

As used herein, the term "heterocycloalkyl" means a ring in which at least one of the carbon atoms of cycloalkyl is independently substituted from nitrogen, oxygen and sulfur.

As used herein, the term "pharmaceutically acceptable salt(s)" refers to a salt prepared from active compounds according to the present disclosure with relatively non-toxic acids or bases, depending on the particular substituents of those compounds. When the compounds have a relatively acidic group, base-added salts can be obtained by contacting the neutral compounds with a sufficient amount of the desired base and a pure or inert solvent. Suitable pharmaceutically acceptable base addition salts include, but are not limited to sodium, potassium, calcium, aluminum, organic amino, magnesium salts and the like. When the compounds have a relatively basic group, acid-added salts can be obtained by contacting the neutral compounds with a sufficient amount of the desired acid and pure or inert solvent. Suitable pharmaceutically acceptable acid addition salts include salts derived from non-toxic organic acids including, but are not limited to, acetic acid, propionic acid, isobutyl acid, oxalic acid, maleic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, and the like, and non-toxic inorganic acids including, but are not limited to, hydrochloric acid, hydrobromic acid, nitric acid, carbonic acid, monohydrogencarbonic acid, phosphoric acid, monohydrogenphosphric acid, dihydrogenphosphoric acid, sulfuric acid, monohydrogensulfuric acid, hydrogen iodide, phosphorous acid and the like. Also it includes a salt of amino acid such as arginate or its analogues, and it also includes analogues of organic acid such as glucuronic or galacturonic acid. Some specific compounds of this disclosure have both basic and acidic functionality for the conversion of compounds with a basic or acidic portion (addition) salts.

As used herein, the phrase "compound(s) of this/the invention" includes any compound(s) of Chemical Formula 1, as well as clathrates, hydrates, solvates, or polymorphs thereof. And, even if the term "compound(s) of the invention" does not mention its pharmaceutically acceptable sat, the term includes salts thereof. In one embodiment, the compounds of this disclosure include stereo-chemically pure compounds, e.g., those substantially free (e.g., greater than 85% ee, greater than 90% ee, greater than 95% ee, greater than 97% ee, or greater than 99% ee) of other stereoisomers. That is, if the compounds of Chemical Formula 1 according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

In one embodiment according to the present invention, preferably, the substituent A of Chemical Formula 1 is phenyl, straight or branched $C_{1-5}$ alkyl unsubstituted or substituted with one or more halogens, or 3 or 6 membered heterocycloalkyl comprising a heteroatom of O or S unsubstituted or substituted with one or more halogens, and $R^1$ and $R^2$ are each independently —H, halogen, —NO$_2$, —CF$_3$, phenyl, straight or branched $C_{1-5}$ alkyl unsubstituted or substituted with one or more halogens, or $C_{1-5}$ straight or branched alkoxy unsubstituted or substituted with one or more halogens.

In one embodiment according to the present invention, more preferably, the substituent A of Chemical Formula 1 is phenyl,

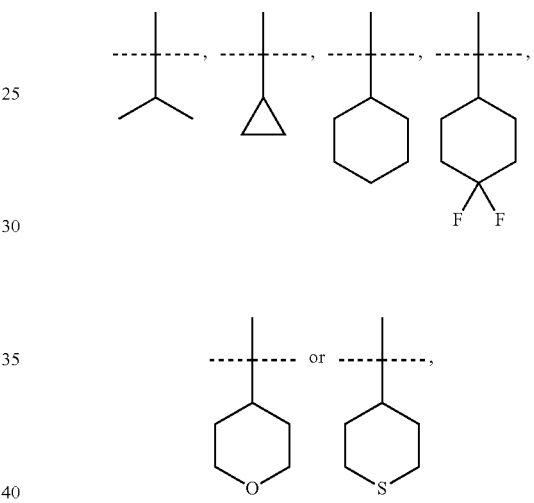

and $R^1$ and $R^2$ are each independently —H, halogen, —NO$_2$, —CF$_3$, —CH$_3$, —C(CH$_3$)$_3$, or phenyl.

In order to achieve the above-mentioned object, the present inventors performed various evaluation experiments after synthesizing various compounds in order to secure compounds having high PDE9A inhibitory activity and high selectivity for them and their use, and finally the present invention was completed by confirming that the compounds of the present invention were suitable for the purposes of the present invention.

Non-limiting examples of preferred compounds according to the present invention include the compounds of Table 1 below and pharmaceutically acceptable salts thereof.

In addition, the present invention provides, as shown in Scheme 1 below, a method A for obtaining a compound represented by Chemical Formula 1 by reacting a compound represented by Chemical Formula 2 with a compound represented by Chemical Formula 3; and a method B for preparing a compound represented by Chemical Formula 1 by reacting a compound represented by Chemical Formula 4 with a compound represented by Chemical Formula 5.

[Scheme 1]

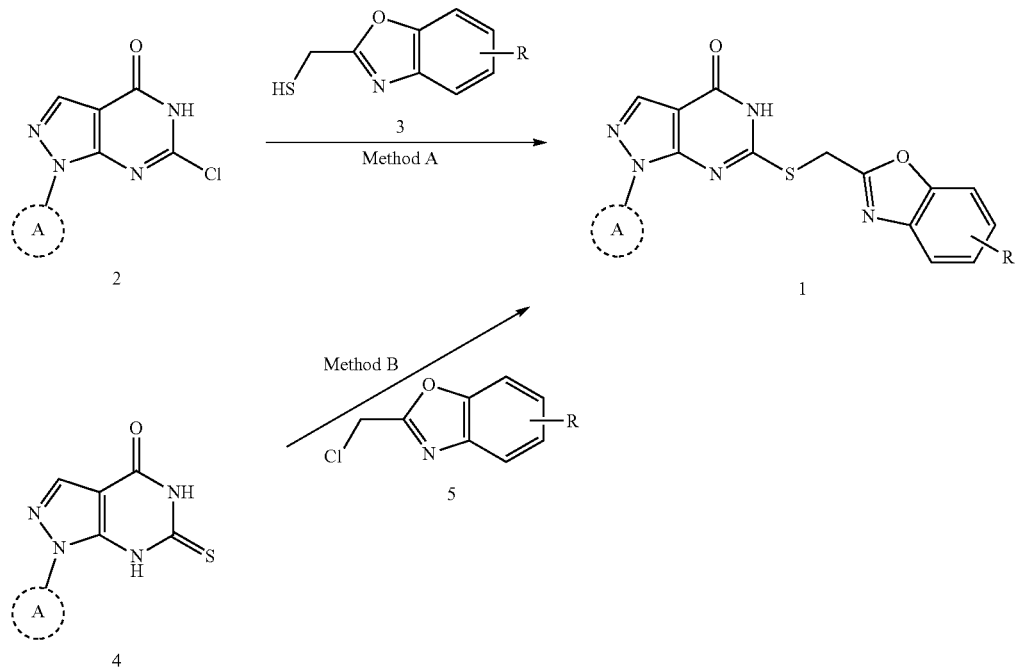

In Scheme 1, A and R are as defined in Chemical Formula 1.

Hereinafter, the manufacturing method represented by Scheme 1 according to the present invention will be described in detail.

The compound represented by Chemical Formula 1 according to the present invention can be obtained by coupling a pyrazolo pyrimidinone compound represented by Chemical Formula 2 as a starting material with a benzoxazole compound represented by Chemical Formula 3 in the presence of a base (Method A), and also can be obtained by coupling a thioxo compound represented by Chemical Formula 4 as a starting material with a halogen compound represented by Chemical Formula 5 in the presence of a base (Method B), as shown in Scheme 1 above. Specific examples are as follows.

Manufacturing Method

As shown in Scheme 1, a compound represented by Chemical Formula 1 can be prepared by coupling a compound represented by Chemical Formula 2 and a compound represented by Chemical Formula 3 (Method A), or coupling a compound represented by Chemical Formula 4 and a compound represented by Chemical Formula 5 (Method B) in the presence of a base.

At this time, the base is used to accelerate the reaction and increase the yield, and the available bases include organic bases such as N,N-dimethylaminopyridine (DMAP), pyridine, triethylamine, N,N-diisopropylethylamine, and 1,8-diazabicyclo[5.4.0]-7-undecene (DBU) or inorganic bases such as sodium bicarbonate, cesium carbonate, potassium carbonate, sodium hydroxide, and potassium hydroxide. These may be used alone or in combination, and may be used in an equivalent amount or in excess.

Further, solvents that can be used in the reaction include ether solvents such as tetrahydrofuran, dioxane, dichloromethane, and 1,2-dimethoxyethane; aromatic hydrocarbon solvents such as benzene, toluene, and xylene; dimethylformamide (DMF); dimethyl sulfoxide; acetonitrile, and the like. These may be used alone or in combination. The reaction temperature is from 0° C. to the boiling point of the solvent.

Preparation 1 of the Starting Material (Compound Represented by Chemical Formula 2)

The compound of Chemical Formula 2, which is the starting material of Scheme 1, can be prepared by a manufacturing method comprising a step of obtaining a compound represented by Chemical Formula 8 by reacting a compound represented by Chemical Formula 6 with a compound represented by Chemical Formula 7 (Step 1); and a step of reacting the compound represented by Chemical Formula 8 obtained in said step 1 to obtain a compound represented by Chemical Formula 2 (Step 2) as shown in Scheme 2 below.

[Scheme 2]

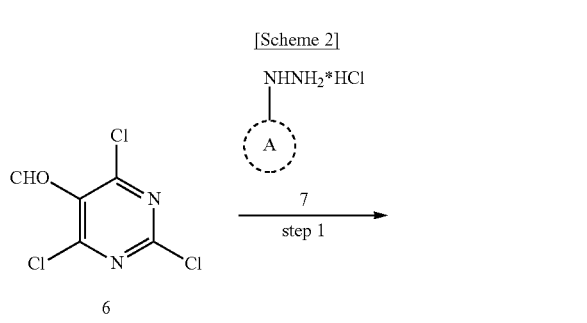

-continued

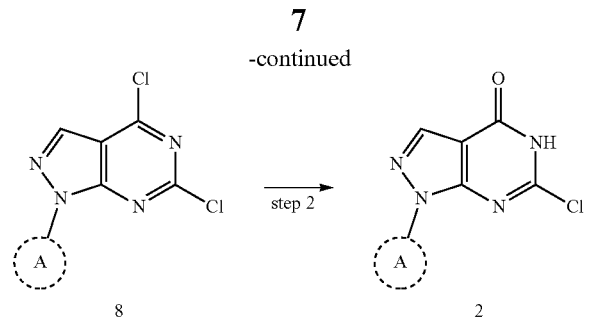

In Scheme 2, A is as defined in Chemical Formula 1.

Hereinafter, the manufacturing method represented by Scheme 2 will be described in detail.

In the manufacturing method represented by Scheme 2, Step 1 is a step to obtain a compound represented by Chemical Formula 8 by reacting a compound represented by Chemical Formula 6 with a compound represented by Chemical Formula 7. Specifically, it is a step to obtain a compound represented by Chemical Formula 8 by condensation reaction of the halide represented by Chemical Formula 6 under basic conditions.

In the above reaction, the compound represented by Chemical Formula 6 was a commercially available compound.

In addition, the bases usable in the reaction include organic bases such as pyridine, triethylamine, N,N-diisopropylethylamine, and 1,8-diazabicyclo[5.4.0]-7-undecene (DBU), and inorganic bases such as sodium hydroxide, sodium carbonate, potassium carbonate, cesium carbonate, and the like, and these may be used in an equivalent amount or in excess.

In addition, the reaction solvent is an ether solvent such as tetrahydrofuran, dioxane, and 1,2-dimethoxyethane, an aromatic hydrocarbon solvent such as benzene, toluene, and xylene, a lower alcohol such as methanol, ethanol, propanol, and butanol, dimethylformamide (DMF), dimethyl sulfoxide (DMSO), acetonitrile, water, etc. can be used alone or in combination, and the reaction temperature is from 0° C. to the boiling point of the solvent.

In the manufacturing method represented by Scheme 2, Step 2 is a step of obtaining a compound represented by Chemical Formula 2 by reacting the compound represented by Chemical Formula 8 obtained in Step 1. Specifically, in this step, a pyrazole pyrimidinone compound represented by Chemical Formula 2 is prepared by hydrolyzing a halogen compound represented by Chemical Formula 8, which is obtained in Step 1, under basic conditions.

In this reaction, the base includes inorganic bases such as sodium carbonate, potassium carbonate, potassium hydroxide, sodium hydroxide, cesium carbonate, barium hydroxide, and the like, and may be used alone or in combination in an equivalent amount or in excess.

In addition, solvents that can be used in the reaction include ether solvents such as tetrahydrofuran, dioxane, dichloromethane, and 1,2-dimethoxyethane, aromatic hydrocarbon solvents such as benzene, toluene, and xylene, alcohol-based solvents such as methanol and ethanol, dimethylformamide (DMF), dimethyl sulfoxide (DMSO), acetonitrile, water, and the like. These may be used alone or in combination. The reaction temperature is from 0° C. to the boiling point of the solvent.

Preparation 2 of the Starting Material (Compound Represented by Chemical Formula 3 or 5)

The compound of Chemical Formula 3, which is a starting material of Scheme 1, can be prepared by a manufacturing method comprising a step of obtaining a compound represented by Chemical Formula 5 by reacting a compound represented by Chemical Formula 9 (Step 1); a step of obtaining a compound represented by Chemical Formula 10 by reacting the compound represented by Chemical Formula 5 obtained in Step 1 (Step 2); and a step of obtaining a compound represented by Chemical Formula 3 by reacting the compound represented by Chemical Formula 10 obtained in Step 2 (Step 3), as shown in Scheme 3 below.

[Scheme 3]

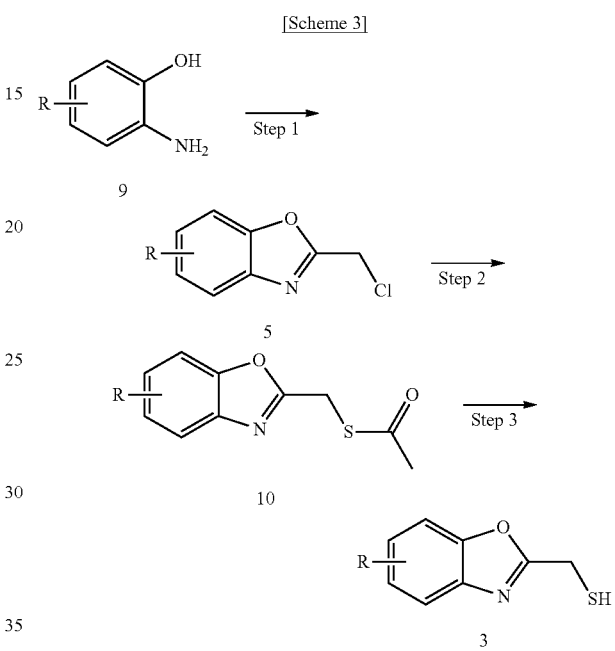

In Reaction Scheme 3, R is as defined in Chemical Formula 1.

Hereinafter, the manufacturing method represented by Scheme 3 will be described in detail.

In the manufacturing method represented by Scheme 3, Step 1 is a step in which a compound represented by Chemical Formula 5 is obtained from a compound represented by Chemical Formula 9. Specifically, this is a step to obtain a compound represented by Chemical Formula 5 by condensation reaction of an amino phenol represented by Chemical Formula 9 under basic conditions.

In the above reaction, the compound represented by Chemical Formula 9 was a commercially available compound.

In addition, the bases usable in the reaction include organic bases such as pyridine, triethylamine, N,N-diisopropylethylamine, and 1,8-diazabicyclo[5.4.0]-7-undecene (DBU), and inorganic bases such as sodium hydroxide, sodium carbonate, potassium carbonate, cesium carbonate, and the like, and these may be used in an equivalent amount or in excess.

In addition, the reaction solvent is an ether solvent such as tetrahydrofuran, dioxane, and 1,2-dimethoxyethane, an aromatic hydrocarbon solvent such as benzene, toluene, and xylene, a lower alcohol such as methanol, ethanol, propanol, and butanol, dimethylformamide (DMF), dimethyl sulfoxide (DMSO), acetonitrile, water, etc. can be used alone or in combination, and the reaction temperature is from 0° C. to the boiling point of the solvent.

In the manufacturing method represented by Scheme 3, Step 2 is a step of obtaining a compound represented by Chemical Formula 10 by reacting the compound represented by Chemical Formula 5 obtained in Step 1. Specifically, this is a step of preparing a thio acetyl compound represented by Chemical Formula 10 by substituting a halogen compound represented by Chemical Formula 5 obtained in Step 1.

At this time, the solvents usable in the reaction include ether solvents such as tetrahydrofuran, dioxane, dichloromethane, and 1,2-dimethoxyethane, aromatic hydrocarbon solvents such as benzene, toluene, and xylene, alcohol-based solvents such as methanol and ethanol, dimethylformamide (DMF), dimethyl sulfoxide (DMSO), acetonitrile, acetone, water, and the like. These may be used alone or in combination. The reaction temperature is from 0° C. to the boiling point of the solvent.

In the manufacturing method represented by Scheme 3, Step 3 is a step of obtaining a compound represented by Chemical Formula 3 by reacting the compound represented by Chemical Formula 10 obtained in Step 2. Specifically, this is a step of preparing a thiol compound represented by Chemical Formula 3 by deprotecting the thio acetyl compound represented by Chemical Formula 10 obtained in Step 2.

In this reaction, the bases usable in the reaction include organic bases such as pyridine, triethylamine, N,N-diisopropylethylamine, and 1,8-diazabicyclo[5.4.0]-7-undecene (DBU), and inorganic bases such as sodium hydroxide, sodium carbonate, potassium carbonate, cesium carbonate, and the like, and these may be used in an equivalent amount or in excess.

In addition, the reaction solvent include an ether solvent such as tetrahydrofuran, dioxane, and 1,2-dimethoxyethane, an aromatic hydrocarbon solvent such as benzene, toluene, and xylene, a lower alcohol such as methanol, ethanol, propanol, and butanol, dimethylformamide (DMF), dimethyl sulfoxide (DMSO), acetonitrile, water, etc. These can be used alone or in combination, and the reaction temperature is from 0° C. to the boiling point of the solvent.

Preparation 3 of the starting material (compound represented by Chemical Formula 4)

The compound of Chemical Formula 4, which is the starting material of Scheme 1, can be obtained by a manufacturing method comprising a step of obtaining a compound represented by Chemical Formula 12 by reacting a compound represented by Chemical Formula 11 with a compound represented by Chemical Formula 7 (Step 1); a step of obtaining a compound represented by Chemical Formula 13 by reacting the compound represented by Chemical Formula 12 obtained in Step 1 (Step 2); and a step of obtaining a compound represented by Chemical Formula 4 by reacting the compound represented by Chemical Formula 13 obtained in Step 2 (Step 3) as shown in Scheme 4 below.

[Scheme 4]

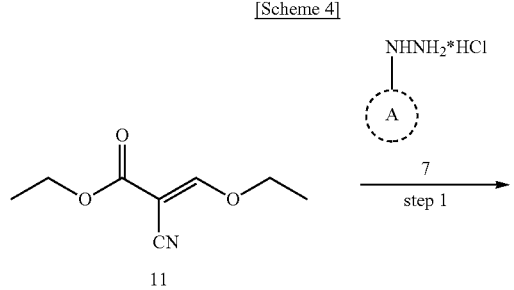

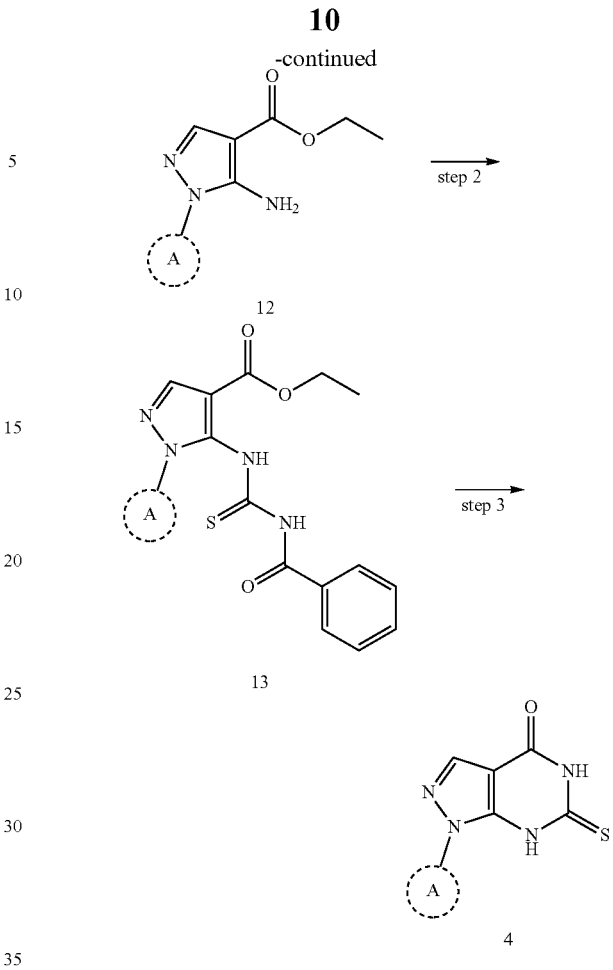

In Reaction Scheme 4, A is as defined in Chemical Formula 1.

Hereinafter, the manufacturing method represented by Scheme 4 will be described in detail.

In the manufacturing method represented by Scheme 4, Step 1 is a step of obtaining a compound represented by Chemical Formula 12 by reacting a compound represented by Chemical Formula 11 with a compound represented by Chemical Formula 7. Specifically, this is a step of obtaining a compound represented by Chemical Formula 12 by a condensation reaction of an acrylate compound represented by Chemical Formula 11 with a hydrazine compound under basic conditions.

In the above reaction, the compound represented by Chemical Formula 11 was a commercially available compound.

In addition, the bases usable in the reaction include organic bases such as pyridine, triethylamine, N,N-diisopropylethylamine, and 1,8-diazabicyclo[5.4.0]-7-undecene (DBU), and inorganic bases such as sodium hydroxide, sodium carbonate, potassium carbonate, cesium carbonate, and the like. These may be used in an equivalent amount or in excess.

In addition, the reaction solvent include an ether solvent such as tetrahydrofuran, dioxane, and 1,2-dimethoxyethane, an aromatic hydrocarbon solvent such as benzene, toluene, and xylene, a lower alcohol such as methanol, ethanol, propanol, and butanol, dimethylformamide (DMF), dimethyl sulfoxide (DMSO), acetonitrile, water, etc. These can be used alone or in combination, and the reaction temperature is from 0° C. to the boiling point of the solvent.

In the manufacturing method represented by Scheme 4, Step 2 is a step of obtaining a compound represented by Chemical Formula 13 by reacting the compound represented by Chemical Formula 12 obtained in Step 1. Specifically, this is a step of preparing a thiourea compound represented by Chemical Formula 13 by coupling reaction of an amine compound represented by Chemical Formula 12 obtained in Step 1 with a thioisocyanate compound.

At this time, the solvents usable in the reaction include ether solvents such as tetrahydrofuran, dioxane, dichloromethane, and 1,2-dimethoxyethane, aromatic hydrocarbon solvents such as benzene, toluene, and xylene, alcohol-based solvents methanol and ethanol, dimethylformamide (DMF), dimethyl sulfoxide (DMSO), acetonitrile, water, and the like. These may be used alone or in combination. The reaction temperature is from 0° C. to the boiling point of the solvent.

In the manufacturing method represented by Scheme 4, Step 3 is a step of obtaining a compound represented by Chemical Formula 4 by reacting the compound represented by Chemical Formula 13 obtained in Step 2. Specifically, this is a step of preparing a thioxo compound represented by Chemical Formula 4 by cyclizing a thiourea compound represented by Chemical Formula 13 obtained in Step 2.

In this case, the bases usable in the reaction include organic bases such as pyridine, triethylamine, N,N-diisopropylethylamine, and 1,8-diazabicyclo[5.4.0]-7-undecene (DBU), and inorganic bases such as sodium hydroxide, sodium carbonate, potassium carbonate, cesium carbonate, and the like. These may be used in an equivalent amount or in excess.

In addition, the reaction solvent is an ether solvent such as tetrahydrofuran, dioxane, and 1,2-dimethoxyethane, an aromatic hydrocarbon solvent such as benzene, toluene, and xylene, a lower alcohol such as methanol, ethanol, propanol, and butanol, dimethylformamide (DMF), dimethyl sulfoxide (DMSO), acetonitrile, water, etc. These can be used alone or in combination, and the reaction temperature is from 0° C. to the boiling point of the solvent.

In another embodiment, the present invention provides a pharmaceutical composition comprising a therapeutically effective amount of the compound of Chemical Formula 1 according to the present invention or a pharmaceutically acceptable salt thereof, and a pharmaceutically acceptable carrier.

In another embodiment, the present invention provides a method for treating a disease or condition comprising administering a therapeutically effective amount of a compound of Chemical Formula 1 or a pharmaceutically acceptable salt thereof to an individual in need thereof, wherein the disease or condition is a phosphodiesterase 9A related disease.

That is, the present invention provides a medical use, characterized in that the compound of Chemical Formula 1 according to the present invention or a pharmaceutically acceptable salt thereof is used as an active ingredient. In one embodiment, the medical use of the present invention is a phosphodiesterase 9A related disease.

In one embodiment, the phosphodiesterase 9A-related disease is a neurological disease or a mental disease. In one embodiment, the neurological or mental disorder is Alzheimer's disease, Huntington's disease, Lewy body dementia, or Pick's syndrome.

In another embodiment, the phosphodiesterase 9A-related disease is heart failure, particularly cardiac output-preserving heart failure or sickle cell disease.

The compounds of the present invention are generally administered in a therapeutically effective amount. The compounds of the present invention can be administered by any suitable route in the form of a pharmaceutical composition suitable for this route, and in an effective dosage for the intended treatment. Effective dosages are generally about 0.001 to about 100 mg/kg body weight/day, preferably about 0.01 to about 50 mg/kg/day, in single or divided doses. Depending on the age, species, and disease or condition being treated, dosage levels below the lower limit of this range may be suitable. In other cases, still larger dosages can be used without harmful side effects. Larger dosages can be divided into several smaller dosages, for administration throughout the day. Methods for determining an appropriate dosage are well known in the art to which the present invention pertains, and for example, Remington: The Science and Practice of Pharmacy, Mack Publishing Co., 20th ed., 2000 can be used.

For the treatment of the diseases or conditions referred to above, the compounds described herein or pharmaceutically acceptable salts thereof can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™

(Nikkol), oleyl ester, Gelucire™, caprylic/caprylic acid mono/diglyceride, sorbitan fatty acid esters, and Solutol HS™

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and isotonic agents.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Administration

Compounds of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

Advantageous Effects

The present invention provides a compound capable of exhibiting various pharmacological activities by inhibiting PDE 9A activity, a pharmaceutical composition containing the compound as an active ingredient, their medical use (especially for treating or alleviating neuropathic diseases and mental diseases), and a method for treating or preventing comprising administering to an individual in need thereof.

MODE FOR INVENTION

The present invention will be described in more detail based on the following examples, but this is not intended to limit the scope of the present invention. In addition, those of ordinary skill in the art will be able to add various modifications and variations to the present invention within the scope not detrimental to the spirit of the present invention.

<Preparation Example 1> Preparation of 6-chloro-1-(tetrahydro-2H-pyran-4-yl)-1,5-dihydro-4H-pyrazolo[3,4-d]pyrimidin-4-one

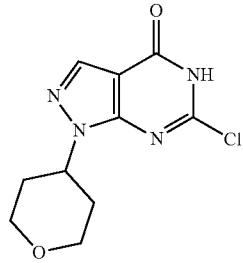 [SMILES: O=c1[nH]c(Cl)nc2c1cnn2C1CCOCC1]

Step 1: Preparation of tert-butyl 2-(tetrahydro-4H-pyran-4-ylidene)hydrazine-1-carboxylate

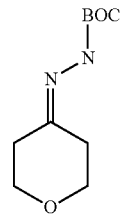 [SMILES: CC(C)(C)OC(=O)NN=C1CCOCC1]

3 g of tetrahydro-4H-pyran-4-one (29.96 mmol) was dissolved in 60 ml of hexane, 3.96 g of tert-butyl carbazite (29.96 mmol) was added, followed by reflux stirring for 3 hours. After completion of the reaction, the mixture was concentrated under reduced pressure to give 6.4 g of the title compound (29.95 mmol) in 100% yield.

Rf=0.19 (hexane:ethyl acetate=1:1, v/v)

$^1$H NMR (500 MHz, DMSO-$d_6$) δ 9.65 (br s, 1H), 3.69 (t, J=5.7 Hz, 2H), 3.60 (t, J=5.7 Hz, 2H), 2.41 (t, J=5.7 Hz, 2H), 2.27 (t, J=5.7 Hz, 2H), 1.43 (s, 9H)

Step 2: Preparation of tert-butyl 2-(tetrahydro-2H-pyran-4-yl)hydrazine-1-carboxylate 6.4 g of tert-butyl 2-(tetrahydro-4H-pyran-4-ylidene)hydrazine-1-carboxylate (29.95 mmol) prepared in Step 1 was dissolved in 80 ml of THF and 12.7 g of sodium triacetoxyborohydride (59.92 mmol) was added, and stirred at room temperature for 15 hours. After completion of the reaction, the reaction solution was extracted with 30 ml of ethyl acetate, washed with 30 ml of an inorganic salt solution, dried over anhydrous sodium sulfate ($Na_2SO_4$), and concentrated under reduced pressure. The residue was purified by column chromatography (hexane:ethyl acetate=1:2, v/v) to give 6 g of the title compound (27.74 mmol) in 92% yield.

Rf=0.38 (hexane:ethyl acetate=1:2, v/v)

$^1$H NMR (500 MHz, $CDCl_3$) δ 6.24 (br s, 1H), 3.95-3.99 (m, 2H), 3.38-3.43 (m, 2H), 3.05-3.11 (m, 1H), 1.75-1.81 (m, 2H), 1.40-1.52 (m, 11H)

Step 3: Preparation of (tetrahydro-2H-pyran-4-yl)hydrazine hydrogen chloride 6 g of tert-butyl 2-(tetrahydro-2H-pyran-4-yl)hydrazine-1-carboxylate (27.74 mmol) obtained in Step 2 was dissolved in 60 ml of methanol, and hydrochloric acid was added thereto, and then stirred at 50° C. for 3 hours. After completion of the reaction, the reaction solution was concentrated under reduced pressure to give 4 g of the title compound (26.21 mmol) in 94% yield.

$^1$H NMR (500 MHz, DMSO-$d_6$) δ 7.25 (br s, 1H), 3.83-3.92 (m, 2H), 3.23-3.31 (m, 2H), 3.08-3.18 (m, 1H), 1.84-1.95 (m, 2H), 1.41-1.54 (m, 2H)

Step 4: Preparation of 4,6-dichloro-1-(tetrahydro-2H-pyran-4-yl)-1H-pyrazolo[3,4-d]pyrimidine

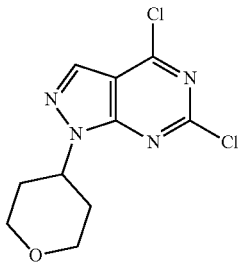 [SMILES: Clc1nc(Cl)c2cnn(C3CCOCC3)c2n1]

5.55 g of 2,4,6-trichloropyrimidine-5-carbaldehyde (26.21 mmol) was dissolved in 60 ml of ethanol and 4 g of (tetrahydro-2H-pyran-4-yl)hydrazine hydrogen chloride (26.21 mmol) obtained in Step 3 above and 14 ml of N,N-diisopropylethylamine (78.63 mmol) were added at −78° C. and stirred for 3 hours. After completion of the reaction, the resultant was extracted with 20 ml of ethyl acetate, washed with 20 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 6.5 g of the title compound (23.80 mmol) in 91% yield.

Rf=0.20 (hexane:ethyl acetate=9:1, v/v)

$^1$H NMR (500 MHz, DMSO-$d_6$) δ 8.57 (s, 1H), 4.96-5.03 (m, 1H), 3.98-4.02 (m, 2H), 3.56-3.61 (m, 2H), 2.10-2.19 (m, 2H), 1.90-1.95 (m, 2H)

Step 5: Preparation of 6-chloro-1-(tetrahydro-2H-pyran-4-yl)-1,5-dihydro-4H-pyrazolo[3,4-d]pyrimidin-4-one 6.5 g of 4,6-dichloro-1-(tetrahydro-2H-pyran-4-yl)-1H-pyrazolo[3,4-d]pyrimidine (23.80 mmol) prepared in Step 4 above was dissolved in 50 ml of THF, and 25 ml of 2N sodium hydroxide (47.60 mmol) was added, and the mixture was stirred under reflux for 15 hours. After completion of the reaction, the mixture was acidified with 6N hydrochloric acid, and the precipitated solid compound was filtered to give 5.4 g of the title compound (21.20 mmol) in 89% yield.

Rf=0.30 (dichloromethane:methanol=20:1, v/v)

$^1$H NMR (500 MHz, DMSO-$d_6$) δ 13.21 (br s, 1H), 8.11 (s, 1H), 4.75-4.81 (m, 1H), 3.95-3.99 (m, 2H), 3.51-3.56 (m, 2H), 2.05-2.12 (m, 2H), 1.81-1.86 (m, 2H)

<Preparation Example 2> Preparation of benzo[d]oxazol-2-ylmethanethiol

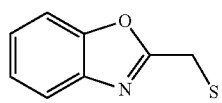 [SMILES: SCc1nc2ccccc2o1]

Step 1: Preparation of 2-(chloromethyl)benzo[d]oxazole

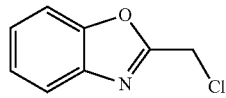

500 mg of 2-aminophenol (4.58 mmol) was dissolved in 15 ml of xylene, and 0.55 ml of chloroacetyl chloride (6.87 mmol) was added at 0° C., followed by stirring. After 30 minutes, 0.7 ml of triethylamine (5.04 mmol) was added, and the mixture was stirred under reflux for 3 hours.

After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=7:1, v/v) to give 600 mg of the title compound (3.58 mmol) in 78% yield.

Rf=0.47 (hexane:ethyl acetate=5:1, v/v)

$^1$H NMR (500 MHz, DMSO-$d_6$) δ 7.76-7.80 (m, 2H), 7.41-7.48 (m, 2H), 5.07 (s, 2H)

Step 2: Preparation of S-(benzo[d]oxazol-2-ylmethyl)ethanethioate 280 mg of 2-(chloromethyl)benzo[d]oxazole (1.67 mmol) obtained in Step 1 was dissolved in 8 ml of acetone, and 286 mg of potassium thioacetate (2.50 mmol) was added, followed by stirring for 1 hour at 60° C. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 290 mg of the title compound (1.39 mmol) in 84% yield.

Rf=0.28 (hexane:ethyl acetate=5:1, v/v)

$^1$H NMR (500 MHz, CDCl$_3$) δ 7.68-7.73 (m, 1H), 7.49-7.54 (m, 1H), 7.30-7.37 (m, 2H), 4.41 (s, 2H), 2.45 (s, 3H)

Step 3: Preparation of benzo[d]oxazol-2-ylmethanethiol 290 mg of S-(benzo[d]oxazol-2-ylmethyl)ethanethioate (1.39 mmol) obtained in Step 1 was dissolved in a mixture of 4 ml of methanol and 1 ml of water, and 386 mg of potassium carbonate (2.79 mmol) was added, followed by stirring at room temperature for 2 hours. After completion of the reaction, the resultant was extracted with 30 ml of ethyl acetate, washed with 20 ml of an inorganic salt solution, dried over anhydrous sodium sulfate (Na$_2$SO$_4$), and concentrated under reduced pressure to give 170 mg of the title compound (1.03 mmol) in 74% yield.

Rf=0.40 (hexane:ethyl acetate=3:1, v/v)

$^1$H NMR (500 MHz, CDCl$_3$) δ 7.70-7.73 (m, 1H), 7.49-7.55 (m, 1H), 7.32-7.39 (m, 2H), 4.17 (s, 1.3H), 3.99 (d, J=8.3 Hz, 0.7H), 2.24 (t, J=8.3 Hz, 0.4H), 1.65 (s, 0.6H)

<Example 1> Preparation of 6-((benzo[d]oxazol-2-ylmethyl)thio)-1-(tetrahydro-2H-pyran-4-yl)-1,5-dihydro-4H-pyrazolo[3,4-d]pyrimidin-4-one

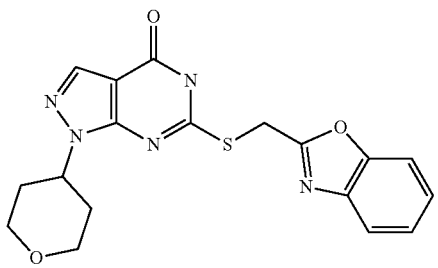

50 mg of 6-chloro-1-(tetrahydro-2H-pyran-4-yl)-1,5-dihydro-4H-pyrazolo[3,4-d]pyrimidin-4-one (0.20 mmol) obtained in Preparation Example 1 above was dissolved in 3 ml of DMF, and 65 mg of benzo[d]oxazol-2-ylmethanethiol (0.39 mmol) obtained in Preparation Example 2 and 83 mg of potassium carbonate (0.60 mmol) were added. The mixture was stirred at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 55 mg of the title compound (0.14 mmol) in 72% yield.

Rf=0.21 (dichloromethane:methanol=20:1, v/v)

$^1$H NMR (500 MHz, DMSO-d$_6$) δ 12.65 (br s, 1H), 7.95 (s, 1H), 7.68-7.71 (m, 2H), 7.33-7.39 (m, 2H), 4.80 (s, 2H), 4.50-4.57 (m, 1H), 3.84-3.89 (m, 2H), 3.35-3.40 (m, 2H), 1.89-1.97 (m, 2H), 1.51-1.56 (m, 2H)

<Preparation Example 3> Preparation of 6-chloro-1-phenyl-1,5-dihydro-4H-pyrazolo[3,4-d]pyrimidin-4-one

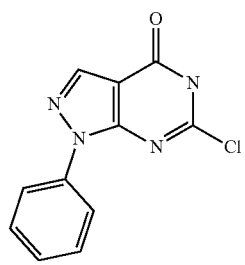 [SMILES: O=c1[nH]c(Cl)nc2c1cnn2-c1ccccc1]

Step 1: Preparation of 4,6-dichloro-1-phenyl-1H-pyrazolo[3,4-d]pyrimidine

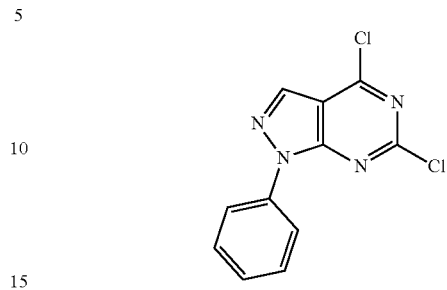

2 g of 2,4,6-trichloropyrimidine-5-carbaldehyde (9.44 mmol) was dissolved in 30 ml of ethonol and 0.9 ml of phenylhydrazine hydrochloride (9.44 mmol) and 4.8 ml of N,N-diisopropylethylamine (28.32 mmol) were added at −78° C., followed by stirring for 3 hours. After completion of the reaction, the resultant was extracted with 300 ml of ethyl acetate, washed with 200 ml of an inorganic salt solution, dried over anhydrous sodium sulfate (Na$_2$SO$_4$), and concentrated under reduced pressure. The residue was purified by column chromatography (hexane:ethyl acetate=20:1, v/v) to give 1.7 g of the title compound (6.41 mmol) in 68% yield.

Rf=0.50 (hexane:ethyl acetate=10:1, v/v)

$^1$H NMR (300 MHz, CD$_3$OD) δ 8.35 (s, 1H), 8.17 (d, J=8.5 Hz, 2H), 7.59 (dd, J=8.5, 7.6 Hz, 2H), 7.44 (dd, J=7.6, 7.6 Hz, 1H)

Step 2: Preparation of 6-chloro-1-phenyl-1,5-dihydro-4H-pyrazolo[3,4-d]pyrimidin-4-one 1.9 g of 4,6-dichloro-1-phenyl-1H-pyrazolo[3,4-d]pyrimidine (8.98 mmol) prepared in Step 1 was dissolved in 20 ml of THF and 10 ml of 2N sodium hydroxide (17.96 mmol) was added and the mixture was stirred under reflux for 15 hours. After completion of the reaction, the mixture was acidified with 6N hydrochloric acid, and the precipitated solid compound was filtered to give 2.2 g of the title compound (8.98 mmol) in 99% yield.

Rf=0.23 (dichloromethane:methanol=20:1, v/v)

$^1$H NMR (500 MHz, DMSO-d$_6$) δ 13.47 (br s, 1H), 8.35 (s, 1H), 7.94 (d, J=8.0 Hz, 2H), 7.58 (dd, J=8.0, 7.4 Hz, 2H), 7.43 (dd, J=7.4, 7.4 Hz, 1H)

<Example 2> Preparation of 6-((benzo[d]oxazol-2-ylmethyl)thio)-1-phenyl-1,5-dihydro-4H-pyrazolo[3,4-d]pyrimidin-4-one

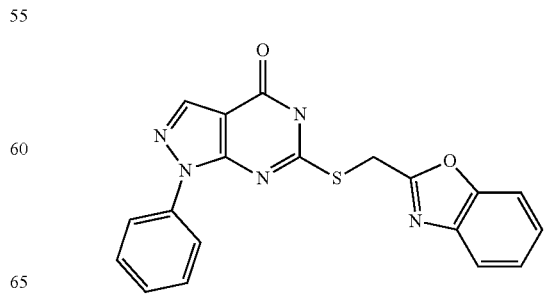

60 mg of 6-chloro-1-phenyl-1,5-dihydro-4H-pyrazolo[3,4-d]pyrimidin-4-one (0.24 mmol) obtained in Preparation Example 2 was dissolved in 5 ml of DMF, and 150 mg of benzo[d]oxazol-2-ylmethanethiol (0.91 mmol) obtained in Preparation Example 2 and 186 mg of potassium carbonate (1.35 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 70 mg of the title compound (0.19 mmol) in 78% yield.

Rf=0.27 (dichloromethane:methanol=20:1, v/v)

$^1$H NMR (500 MHz, DMSO-d$_6$) δ 12.96 (br s, 1H), 8.22 (s, 1H), 7.93 (d, J=7.8 Hz, 2H), 7.69 (dd, J=8.8, 8.3 Hz, 2H), 7.45 (dd, J=7.8, 7.5 Hz, 2H), 7.32-7.38 (m, 3H), 5.75 (s, 2H)

<Preparation Example 4> Preparation of (5-methylbenzo[d]oxazol-2-yl)methanethiol

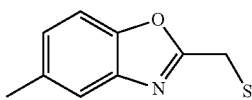

Step 1: Preparation of 2-(chloromethyl)-5-methylbenzo[d]oxazole

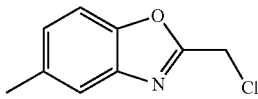

500 mg of 2-amino-4-methylphenol (4.06 mmol) was dissolved in 15 ml of xylene, and 0.48 ml of chloroacetyl chloride (6.09 mmol) was added at 0° C., followed by stirring. After 30 minutes, 0.62 ml of triethylamine (4.47 mmol) was added, and the mixture was stirred under reflux for 3 hours. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 240 mg of the title compound (1.32 mmol) in 33% yield.

Rf=0.54 (hexane:ethyl acetate=5:1, v/v)

$^1$H NMR (500 MHz, CDCl$_3$) δ 7.54 (s, 1H), 7.45 (d, J=8.3 Hz, 1H), 7.22 (d, J=8.3 Hz, 1H), 4.76 (s, 2H), 2.49 (s, 3H)

Step 2: Preparation of S-((-5-methylbenzo[d]oxazol-2-yl)methyl)ethanethioate 220 mg of 2-(chloromethyl)-5-methylbenzo[d]oxazole (1.21 mmol) obtained in Step 1 was dissolved in 6 ml of acetone, and 208 mg of potassium thioacetate (1.82 mmol) was added, followed by stirring at 60° C. for 1 hour. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 250 mg of the title compound (1.13 mmol) in 93% yield.

Rf=0.40 (hexane:ethyl acetate=5:1, v/v)

$^1$H NMR (500 MHz, CDCl$_3$) δ 7.49 (s, 1H), 7.39 (d, J=8.3 Hz, 1H), 7.16 (d, J=8.3 Hz, 1H), 4.40 (s, 2H), 2.47 (s, 3H), 2.45 (s, 3H)

Step 3: Preparation of (5-methylbenzo[d]oxazol-2-yl)methanethiol 230 mg of S-((-5-methylbenzo[d]oxazol-2-yl)methyl)ethanethioate (1.04 mmol) obtained in Step 2 was dissolved in a mixture of 4 ml of methanol and 1 ml of water, and 287 mg of potassium carbonate (2.08 mmol) was added, followed by stirring at room temperature for 2 hours. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 170 mg of the title compound (0.95 mmol) in 91% yield.

Rf=0.17 (hexane:ethyl acetate=5:1, v/v)

$^1$H NMR (500 MHz, CDCl$_3$) δ 7.49 (s, 1H), 7.41 (d, J=8.3 Hz, 1H), 7.17 (d, J=8.3 Hz, 1H), 3.96 (d, J=8.4 Hz, 2H), 2.48 (s, 3H), 2.23 (t, J=8.4 Hz, 1H)

<Example 3> Preparation of 6-(((5-methylbenzo[d]oxazol-2-yl)methyl)thio)-1-phenyl-1,5-dihydro-4H-pyrazolo[3,4-d]pyrimidin-4-one

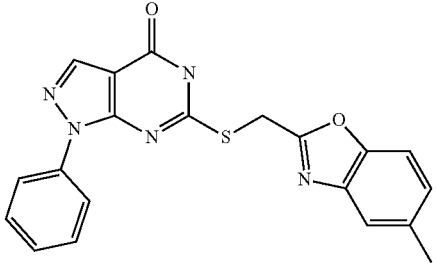 [SMILES: Cc1ccc2oc(CSc3nc4c(cnn4-c4ccccc4)c(=O)[nH]3)nc2c1]

50 mg of 6-chloro-1-phenyl-1,5-dihydro-4H-pyrazolo[3,4-d]pyrimidin-4-one (0.20 mmol) obtained in Preparation Example 2 was dissolved in 5 ml of DMF, and 100 mg of (5-methylbenzo[d]oxazol-2-yl)methanethiol (0.55 mmol) obtained in Preparation Example 4 above and 83 mg of potassium carbonate (0.60 mmol) were added, followed by stirring 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 60 mg of the title compound (0.15 mmol) in 77% yield.

Rf=0.27 (dichloromethane:methanol=20:1, v/v)

$^1$H NMR (500 MHz, DMSO-d$_6$) δ 12.91 (br s, 1H), 7.94 (d, J=7.8 Hz, 2H), 7.56 (d, J=8.5 Hz, 1H), 7.49 (s, 1H), 7.47

(dd, J=7.8, 7.4 Hz, 2H), 7.36 (dd, J=7.4, 7.4 Hz, 1H), 7.18 (d, J=8.5 Hz, 1H), 4.79 (s, 2H), 2.38 (s, 3H)

<Preparation Example 5> Preparation of (5-fluorobenzo[d]oxazol-2-yl)methanethiol

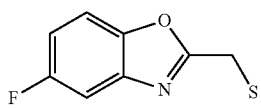 [SMILES: Fc1ccc2oc(CS)nc2c1]

Step 1: Preparation of 2-(chloromethyl)-5-methylbenzo[d]oxazole

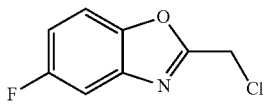 [SMILES: Fc1ccc2oc(CCl)nc2c1]

500 mg of 2-amino-4-fluorophenol (3.93 mmol) was dissolved in 15 ml of xylene, and 0.50 ml of chloroacetyl chloride (5.90 mmol) was added at 0° C., followed by stirring. After 30 minutes, 0.60 ml of triethylamine (4.32 mmol) was added, and the mixture was stirred under reflux for 3 hours. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 200 mg of the title compound (1.08 mmol) in 27% yield.

Rf=0.56 (hexane:ethyl acetate=5:1, v/v)

$^1$H NMR (500 MHz, CDCl$_3$) δ 7.52 (dd, J=8.9, 4.8 Hz, 1H), 7.45 (dd, J=8.1, 2.5 Hz, 1H), 7.16 (ddd, J=9.1, 8.9, 2.5 Hz, 1H), 4.76 (s, 2H)

Step 2: Preparation of S-((-5-fluorobenzo[d]oxazol-2-yl)methyl)ethanethioate 180 mg of 2-(chloromethyl)-5-fluorobenzo[d]oxazole (0.97 mmol) obtained in Step 1 was dissolved in 6 ml of acetone, and 166 mg of potassium thioacetate (1.45 mmol) was added, followed by stirring at 60° C. for 1 hour. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 210 mg of the title compound (0.93 mmol) in 96% yield.

Rf=0.44 (hexane:ethyl acetate=5:1, v/v)

$^1$H NMR (500 MHz, CDCl$_3$) δ 7.45 (dd, J=8.8, 4.2 Hz, 1H), 7.39 (dd, J=8.3, 2.7 Hz, 1H), 7.09 (ddd, J=9.0, 8.8, 2.7 Hz, 1H), 4.40 (s, 2H), 2.46 (s, 3H)

Step 3: Preparation of (5-fluorobenzo[d]oxazol-2-yl)methanethiol 190 mg of S-((-5-fluorobenzo[d]oxazol-2-yl)methyl)ethanethioate (0.84 mmol) obtained in Step 2 was dissolved in a mixture of 4 ml of methanol and 1 ml of water, and 233 mg of potassium carbonate (1.69 mmol) was added, followed by stirring at room temperature for 2 hours. After completion of the reaction, the resultant was extracted with 20 ml of ethyl acetate, washed with 20 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 115 mg of the title compound (0.63 mmol) in 75% yield.

Rf=0.22 (hexane:ethyl acetate=5:1, v/v)

$^1$H NMR (500 MHz, CDCl$_3$) δ 7.47 (dd, J=8.8, 4.1 Hz, 1H), 7.40 (dd, J=9.2, 2.5 Hz, 1H), 7.10 (ddd, J=9.2, 8.8, 2.5 Hz, 1H), 3.97 (d, J=8.2 Hz, 2H), 2.25 (t, J=8.2 Hz, 1H)

<Example 4> Preparation of 6-(((5-fluorobenzo[d]oxazol-2-yl)methyl)thio)-1-phenyl-1,5-dihydro-4H-pyrazolo[3,4-d]pyrimidin-4-one

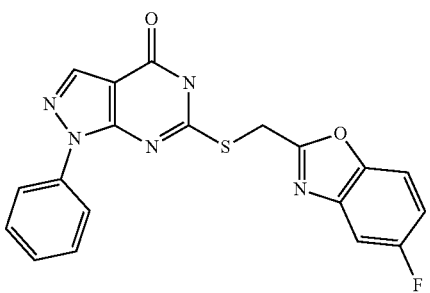 [SMILES: O=c1[nH]c(SCc2nc3cc(F)ccc3o2)nc2c1cnn2-c1ccccc1]

50 mg of 6-chloro-1-phenyl-1,5-dihydro-4H-pyrazolo[3,4-d]pyrimidin-4-one (0.20 mmol) obtained in Preparation Example 2 was dissolved in 5 ml of DMF, and 90 mg of (5-fluorobenzo[d]oxazol-2-yl)methanethiol (0.49 mmol) obtained in Preparation Example 5 and 83 mg of potassium carbonate (0.60 mmol) were added, followed by stirring 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 54 mg of the title compound (0.14 mmol) in 69% yield.

Rf=0.27 (dichloromethane:methanol=20:1, v/v)

$^1$H NMR (500 MHz, DMSO-d$_6$) δ 12.91 (br s, 1H), 8.22 (s, 1H), 7.90 (d, J=8.3 Hz, 2H), 7.72 (dd, J=8.3, 4.7 Hz, 1H), 7.60 (dd, J=9.2, 2.6 Hz, 1H), 7.46 (dd, J=8.3, 7.4 Hz, 2H), 7.36 (dd, J=7.4, 7.4 Hz, 1H), 7.22 (ddd, J=9.1, 8.3, 2.6 Hz, 1H), 4.82 (s, 2H)

<Preparation Example 6> Preparation of (6-methylbenzo[d]oxazol-2-yl)methanethiol

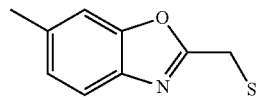

Step 1: Preparation of 2-(chloromethyl)-6-methylbenzo[d]oxazole

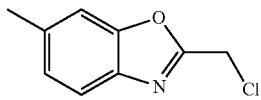

500 mg of 6-amino-m-cresol (4.00 mmol) was dissolved in 15 ml of xylene, and 0.48 ml of chloroacetyl chloride (6.09 mmol) was added at 0° C., followed by stirring. After 30 minutes, 0.62 ml of triethylamine (4.47 mmol) was added, and the mixture was stirred under reflux for 3 hours. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=20:1, v/v) to give 640 mg of the title compound (3.52 mmol) in 88% yield.

Rf=0.64 (hexane:ethyl acetate=9:1, v/v)
$^1$H NMR (500 MHz, CDCl$_3$) δ 7.52 (dd, J=8.9, 4.8 Hz, 1H), 7.45 (dd, J=8.1, 2.5 Hz, 1H), 7.16 (ddd, J=9.1, 8.9, 2.5 Hz, 1H), 4.76 (s, 2H)

Step 2: Preparation of S-((-6-methylbenzo[d]oxazol-2-yl)methyl)ethanethioate 600 mg of 2-(chloromethyl)-6-methylbenzo[d]oxazole (3.30 mmol) obtained in Step 1 was dissolved in 10 ml of acetone, and 566 mg of potassium thioacetate (4.96 mmol) was added, followed by stirring 60° C. for 1 hour. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 690 mg of the title compound (3.12 mmol) in 94% yield.

Rf=0.18 (hexane:ethyl acetate=9:1, v/v)
$^1$H NMR (500 MHz, CDCl$_3$) δ 7.57 (d, J=8.0 Hz, 1H), 7.31 (s, 1H), 7.15 (d, J=8.0 Hz, 1H), 4.39 (s, 2H), 2.48 (s, 3H), 2.44 (s, 3H)

Step 3: Preparation of (6-methylbenzo[d]oxazol-2-yl)methanethiol 500 mg of S-((-6-methylbenzo[d]oxazol-2-yl)methyl)ethanethioate (2.26 mmol) obtained in Step 2 was dissolved in a mixture of 6 ml of methanol and 1 ml of water, and 624 mg of potassium carbonate (4.52 mmol) was added, followed by stirring at room temperature for 2 hours. After completion of the reaction, the resultant was extracted with 50 ml of ethyl acetate, washed with 50 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 370 mg of the title compound (2.06 mmol) in 91% yield.

Rf=0.36 (hexane:ethyl acetate=3:1, v/v)
$^1$H NMR (500 MHz, CDCl$_3$) δ 7.58 (d, J=8.0 Hz, 1H), 7.33 (s, 1H), 7.17 (d, J=8.0 Hz, 1H), 3.96 (d, J=8.3 Hz, 2H), 2.50 (s, 3H), 2.22 (t, J=8.3 Hz, 1H)

<Example 5> Preparation of 6-((((6-methylbenzo[d]oxazol-2-yl)methyl)thio)-1-phenyl-1,5-dihydro-4H-pyrazolol[3,4-d]pyrimidin-4-one

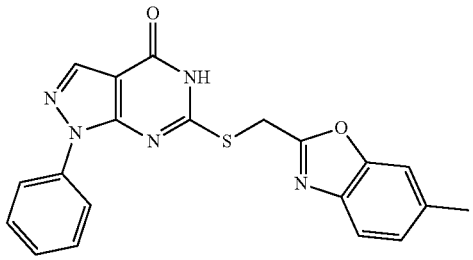 [SMILES: Cc1ccc2nc(CSc3nc4c(cnn4-c4ccccc4)c(=O)[nH]3)oc2c1]

50 mg of 6-chloro-1-phenyl-1,5-dihydro-4H-pyrazolo[3,4-d]pyrimidin-4-one (0.20 mmol) obtained in Preparation Example 2 was dissolved in 5 ml of DMF and 108 mg of (6-methylbenzo[d]oxazol-2-yl)methanethiol (0.60 mmol) obtained in Preparation Example 6 and 83 mg of potassium carbonate (0.60 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 67 mg of the title compound (0.17 mmol) in 86% yield.

Rf=0.27 (dichloromethane:methanol=20:1, v/v)
$^1$H NMR (500 MHz, DMSO-d$_6$) δ 12.94 (br s, 1H), 8.23 (s, 1H), 7.94 (d, J=7.8 Hz, 1H), 7.57 (d, J=8.2 Hz, 1H), 7.45-7.49 (m, 3H), 7.37 (dd, J=7.5, 7.5 Hz, 1H), 7.16 (d, J=8.2 Hz, 1H), 4.79 (s, 2H), 2.41 (s, 3H)

<Preparation Example 7> Preparation of (5-chlorobenzo[d]oxazol-2-yl)methanethiol

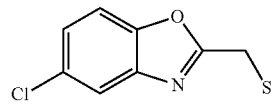 [SMILES: SCc1nc2cc(Cl)ccc2o1]

Step 1: Preparation of 2-chloro-N-(5-chloro-2-hydroxyphenyl)acetamide

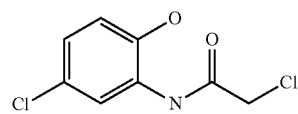 [SMILES: O=C(CCl)Nc1cc(Cl)ccc1O]

1 g of 2-amino-4-chlorophenol (6.96 mmol) was dissolved in 20 ml of MC, and 0.83 ml of chloroacetyl chloride (10.44 mmol) was added at 0° C., followed by stirring. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=3:1, v/v) to give 1.3 g of the title compound (5.91 mmol) in 85% yield.

Rf=0.20 (hexane:ethyl acetate=5:1, v/v)

$^1$H NMR (500 MHz, DMSO-d$_6$) 10.81 (br s, 1H), 6.94-6.98 (m, 2H), 6.90 (d, J=2.0 Hz, 1H), 4.59 (s, 2H)

Step 2: Preparation of 5-chloro-2-(chloromethyl)benzo[d]oxazole 200 mg of 2-chloro-N-(5-chloro-2-hydroxyphenyl)acetamide (0.91 mmol) obtained in Step 1 was dissolved in 5 ml of phenol, and 78 mg of p-toluenesulfonyl acid (0.45 mmol)) was added, followed by stirring under reflux for 3 hours. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane: ethyl acetate=10:1, v/v) to give 180 mg of the title compound (0.89 mmol) in 98% yield.

Rf=0.48 (hexane:ethyl acetate=5:1, v/v)

$^1$H NMR (500 MHz, DMSO-d$_6$) δ 7.93 (d, J=2.0 Hz, 1H), 7.85 (d, J=8.6 Hz, 1H), 7.53 (dd, J=8.6, 2.0 Hz, 1H), 5.09 (s, 2H)

Step 3: Preparation of S-((5-chlorobenzo[d]oxazol-2-yl)methyl)ethanethioate 180 mg of 5-chloro-2-(chloromethyl)benzo[d]oxazole (0.89 mmol) obtained in Step 2 was dissolved in 6 ml of acetone, and 152 mg of potassium thioacetate (1.33 mmol) was added, followed by stirring 60° C. for 1 hour. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethylacetate=5:1, v/v) to give 200 mg of the title compound (0.83 mmol) in 93% yield.

Rf=0.38 (hexane:ethyl acetate=5:1, v/v)

$^1$H NMR (500 MHz, DMSO-d$_6$) δ 7.84 (d, J=1.9 Hz, 1H), 7.76 (d, J=8.5 Hz, 1H), 7.45 (dd, J=8.5, 1.9 Hz, 1H), 4.47 (s, 2H), 2.43 (s, 3H)

Step 4: Preparation of (5-chlorobenzo[d]oxazol-2-yl)methanethiol 200 mg of S-((5-chlorobenzo[d]oxazol-2-yl)methyl)ethanethioate (0.83 mmol) obtained in Step 3 was dissolved in a mixture of 5 ml of methanol and 1 ml of water, and 229 mg of potassium carbonate (1.66 mmol) was added, followed by stirring at room temperature for 2 hours. After completion of the reaction, the resultant was extracted with 30 ml of ethyl acetate, washed with 30 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 160 mg of the title compound (0.80 mmol) in 96% yield.

Rf=0.28 (hexane:ethyl acetate=5:1, v/v)

$^1$H NMR (500 MHz, CDCl$_3$) δ 7.70 (d, J=2.0 Hz, 1H), 7.46 (d, J=8.4 Hz, 1H), 7.35 (dd, J=8.4, 2.0 Hz, 1H), 3.97 (d, J=8.2 Hz, 2H), 2.25 (t, J=8.2 Hz, 1H)

<Example 6> Preparation of 6-(((5-chlorobenzo[d]oxazol-2-yl)methyl)thio)-1-phenyl-1,5-dihydro-4H-pyrazolo[3,4-d]pyrimidin-4-one

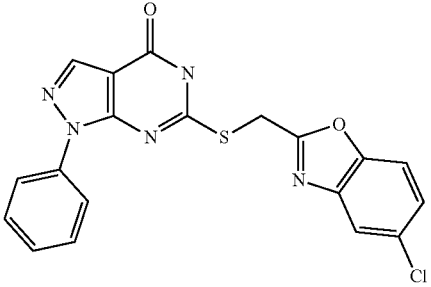 [SMILES: O=c1[nH]c(SCc2nc3cc(Cl)ccc3o2)nc2c1cnn2-c1ccccc1]

60 mg of 6-chloro-1-phenyl-1,5-dihydro-4H-pyrazolo[3,4-d]pyrimidin-4-one (0.24 mmol) obtained in Preparation Example 2 was dissolved in 5 ml of DMF and 150 mg of (5-chlorobenzo[d]oxazol-2-yl)methanethiol (0.75 mmol) obtained in Preparation Example 7 and 100 mg of potassium carbonate (0.72 mmol) were added, followed by stirring 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 95 mg of the title compound (0.23 mmol) in 96% yield.

Rf=0.17 (dichloromethane:methanol=20:1, v/v)

$^1$H NMR (500 MHz, DMSO-d$_6$) δ 12.95 (br s, 1H), 8.23 (s, 1H), 7.91 (d, J=8.3 Hz, 2H), 7.83 (d, J=2.1 Hz, 1H), 7.75 (d, J=8.6 Hz, 1H), 7.47 (dd, J=8.3, 7.5 Hz, 2H), 7.42 (dd, J=8.6, 2.1 Hz, 1H), 7.36 (dd, J=7.5, 7.5 Hz, 1H), 4.84 (s, 2H)

<Preparation Example 8> Preparation of (5-bromobenzo[d]oxazol-2-yl)methanethiol

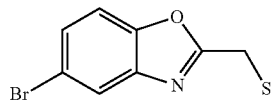 [SMILES: SCc1nc2cc(Br)ccc2o1]

Step 1: Preparation of 2-chloro-N-(5-bromo-2-hydroxyphenyl)acetamide

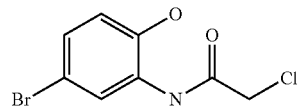 [SMILES: O=C(CCl)Nc1cc(Br)ccc1O]

500 mg of 2-amino-4-bromophenol (2.66 mmol) was dissolved in 10 ml of MC, and 0.32 ml of chloroacetyl chloride (3.99 mmol) was added at 0° C., followed by stirring. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=3:1, v/v) to give 600 mg of the title compound (2.27 mmol) in 85% yield.

Rf=0.23 (hexane:ethyl acetate=5:1, v/v)

$^1$H NMR (500 MHz, CDCl$_3$) δ 8.37 (br s, 1H), 7.12 (dd, J=8.5, 2.3 Hz, 1H), 6.98 (d, J=2.3 Hz, 1H), 6.89 (d, J=8.5 Hz, 1H), 4.65 (s, 2H)

Step 2: Preparation of 5-bromo-2-(chloromethyl)benzo[d]oxazole 600 mg of 2-chloro-N-(5-broro-2-hydroxyphenyl)acetamide (2.27 mmol) obtained in Step 1 was dissolved in 8 ml of phenol, and 195 mg of p-toluenesulfonyl acid (1.13 mmol) was added, followed by stirring under reflux for 3 hours. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 340 mg of the title compound (1.38 mmol) in 61% yield.

Rf=0.50 (hexane:ethyl acetate=5:1, v/v)

$^1$H NMR (500 MHz, DMSO-d$_6$) δ 8.06 (d, J=2.0 Hz, 1H), 7.79 (d, J=8.6 Hz, 1H), 7.65 (dd, J=8.6, 2.0 Hz, 1H), 5.09 (s, 2H)

Step 3: Preparation of S-((5-brorobenzo[d]oxazol-2-yl)methyl)ethanethioate 320 mg of 5-broro-2-(chloromethyl)benzo[d]oxazole (1.30 mmol) obtained in Step 2 was dissolved in 6 ml of acetone, and 222 mg of potassium thioacetate (1.95 mmol) was added, followed by stirring at 60° C. for 1 hour. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 360 mg of the title compound (1.26 mmol) in 97% yield.

Rf=0.39 (hexane:ethyl acetate=5:1, v/v)

$^1$H NMR (500 MHz, DMSO-d$_6$) δ 7.97 (d, J=1.7 Hz, 1H), 7.72 (d, J=8.5 Hz, 1H), 7.57 (dd, J=8.5, 1.7 Hz, 1H), 4.48 (s, 2H), 2.43 (s, 3H)

Step 4: Preparation of (5-brorobenzo[d]oxazol-2-yl)methanethiol 350 mg of S-((5-brorobenzo[d]oxazol-2-yl)methyl)ethanethioate (1.22 mmol) obtained in Step 3 was dissolved in a mixture of 5 ml of methanol and 1 ml of water, and 338 mg of potassium carbonate (2.45 mmol) was added, followed by stirring at room temperature for 2 hours. After completion of the reaction, the resultant was extracted with 30 ml of ethyl acetate, washed with 30 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 290 mg of the title compound (1.19 mmol) in 97% yield.

Rf=0.30 (hexane:ethyl acetate=5:1, v/v)

$^1$H NMR (500 MHz, CDCl$_3$) δ 7.85 (d, J=1.9 Hz, 1H), 7.49 (dd, J=8.5, 1.9 Hz, 1H), 7.42 (d, J=8.5 Hz, 1H), 3.97 (d, J=8.3 Hz, 2H), 2.25 (t, J=8.3 Hz, 1H)

<Example 7> Preparation of 6-(((5-bromobenzo[d]oxazol-2-yl)methyl)thio)-1-phenyl-1,5-dihydro-4H-pyrazolo[3,4-d]pyrimidin-4-one

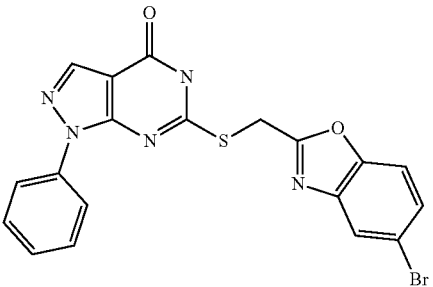 [SMILES: O=c1[nH]c(SCc2nc3cc(Br)ccc3o2)nc2c1cnn2-c1ccccc1]

60 mg of 6-chloro-1-phenyl-1,5-dihydro-4H-pyrazolo[3,4-d]pyrimidin-4-one (0.24 mmol) obtained in Preparation Example 2 was dissolved in 5 ml of DMF, and 180 mg of (5-bromobenzo[d]oxazol-2-yl)methanethiol (0.75 mmol) obtained in Preparation Example 8 and 100 mg of potassium carbonate (0.72 mmol) were added, followed by stirring at 60° C. for 3 hours.

After completion of the reaction, extraction was performed with 20 ml of ethyl acetate, washed with 30 ml of an inorganic salt solution, dried over anhydrous sodium sulfate (Na2SO4), and the reaction solution was concentrated under reduced pressure. The residue was purified by column chromatography (dichloromethane:methanol=20:1, v/v) to give 88 mg of the title compound (0.19 mmol) in 81% yield.

Rf=0.28 (dichloromethane:methanol=20:1, v/v)

$^1$H NMR (500 MHz, DMSO-d$_6$) δ 12.95 (br s, 1H), 8.23 (s, 1H), 7.96 (d, J=1.9 Hz, 1H), 7.91 (d, J=8.5 Hz, 2H), 7.70 (d, J=8.5 Hz, 1H), 7.54 (dd, J=8.5, 1.9 Hz, 1H), 7.47 (dd, J=8.5, 7.2 Hz, 2H), 7.36 (dd, J=7.2, 7.2 Hz, 1H), 4.84 (s, 2H)

<Preparation Example 9> Preparation of 6-chloro-1-(4,4-difluorocyclohexyl)-1,5-dihydro-4H-pyrazolo[3,4-d]pyrimidin-4-one

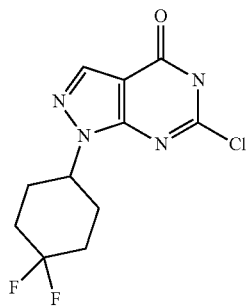 [SMILES: O=c1[nH]c(Cl)nc2c1cnn2C1CCC(F)(F)CC1]

Step 1: Preparation of tert-butyl 2-(4,4-difluorocyclohexylidene)hydrazine-1-carboxylate

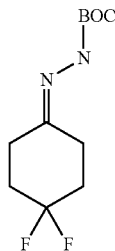

300 mg of 4,4-difluorocyclohexanone (2.24 mmol) was dissolved in 6 ml of hexane, 296 mg of tert-butyl carbazite (2.24 mmol) was added, followed by stirring under reflux for 3 hours. After completion of the reaction, the resultant was concentrated under reduced pressure to give 550 mg of the title compound (2.24 mmol) in 100% yield.

Rf=0.30 (hexane:ethyl acetate=3:1, v/v)
$^1$H NMR (300 MHz, DMSO-d$_6$) δ 9.72 (br s, 1H), 2.45 (t, J=6.4 Hz, 2H), 2.37 (t, J=6.4 Hz, 2H), 1.99-2.12 (m, 4H), 1.43 (s, 9H)

Step 2: Preparation of tert-butyl 2-(4,4-difluorocyclohexyl)hydrazine-1-carboxylate 550 mg of tert-butyl 2-(4,4-difluorocyclohexylidene)hydrazine-1-carboxylate (2.21 mmol) obtained in Step 1 was dissolved in 5 ml of THF, and 950 mg of sodium triacetoxy borohydride (4.48 mmol) was added, followed by stirring at room temperature for 15 hours. After completion of the reaction, the resultant was extracted with 30 ml of ethyl acetate, washed with 30 ml of an inorganic salt solution, dried over anhydrous sodium sulfate (Na$_2$SO$_4$), and concentrated under reduced pressure. The residue was purified by column chromatography (hexane:ethyl acetate=3:1, v/v) to give 465 mg of the title compound (1.86 mmol) in 84% yield.

Rf=0.45 (hexane:ethyl acetate=3:1, v/v)
$^1$H NMR (300 MHz, DMSO-d$_6$) δ 8.20 (br s, 1H), 4.38 (br s, 1H), 2.86-2.95 (m, 1H), 1.93-2.11 (m, 2H), 1.59-1.83 (m, 4H), 1.41-1.49 (m, 2H), 1.38 (s, 9H)

Step 3: Preparation of (4,4-difluorocyclohexyl)hydrazine hydrogen chloride 465 mg of tert-butyl 2-(4,4-difluorocyclohexyl)hydrazine-1-carboxylate (1.86 mmol) obtained in Step 2 was dissolved in 5 ml of methanol, and hydrochloric acid was added thereto, followed by stirring at 50° C. for 3 hours. After completion of the reaction, the reaction solution was concentrated under reduced pressure to give 335 mg of the title compound (1.79 mmol) in 96% yield.

Rf=0.00 (hexane:ethyl acetate=3:1, v/v)
$^1$H NMR (300 MHz, DMSO-d$_6$) δ 3.05-3.12 (m, 1H), 1.96-2.09 (m, 4H), 1.79-1.91 (m, 2H), 1.52-1.59 (m, 2H)

Step 4: Preparation of 4,6-dichloro-1-(4,4-difluorocyclohexyl)-1H-pyrazolo[3,4-d]pyrimidine 340 mg of 2,4,6-trichloropyrimidine-5-carbaldehyde (1.61 mmol) was dissolved in 5 ml of ethanol and 300 mg of (4,4-difluorocyclohexyl)hydrazine hydrogen chloride (1.61 mmol) obtained in Step 3 above and 0.86 ml of N,N-diisopropylethylamine (4.82 mmol) were added at −78° C., followed by stirring for 3 hours. After completion of the reaction, the resultant was extracted with 20 ml of ethyl acetate, washed with 20 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 360 mg of the title compound (1.17 mmol) in 73% yield.

Rf=0.35 (hexane:ethyl acetate=9:1, v/v)
$^1$H NMR (500 MHz, DMSO-d$_6$) δ 8.57 (s, 1H), 4.97-5.04 (m, 1H), 2.13-2.23 (m, 6H), 2.03-2.07 (m, 2H)

Step 5: Preparation of 6-chloro-1-(4,4-difluorocyclohexyl)-1,5-dihydro-4H-pyrazolo[3,4-d]pyrimidin-4-one 340 mg of 4,6-dichloro-1-(4,4-difluorocyclohexyl)-1H-pyrazolo[3,4-d]pyrimidine (1.11 mmol) obtained in Step 4 was dissolved in 5 ml of THF, and 1.2 ml of 2N sodium hydroxide (2.21 mmol) was added, followed by stirring under reflux for 15 hours. After completion of the reaction, the mixture was acidified with 6N hydrochloric acid, and the precipitated solid compound was filtered to give 320 mg of the title compound (1.11 mmol) in 99% yield.

Rf=0.38 (dichloromethane:methanol=20:1, v/v)
$^1$H NMR (500 MHz, DMSO-d$_6$) δ 8.11 (s, 1H), 4.77-4.81 (m, 1H), 2.08-2.17 (m, 6H), 1.94-2.00 (m, 2H)

<Example 8> Preparation of 6-((benzo[d]oxazol-2-ylmethyl)thio)-1-(4,4-difluorocyclohexyl)-1,5-dihydro-4H-pyrazolo[3,4-d]pyrimidin-4-one

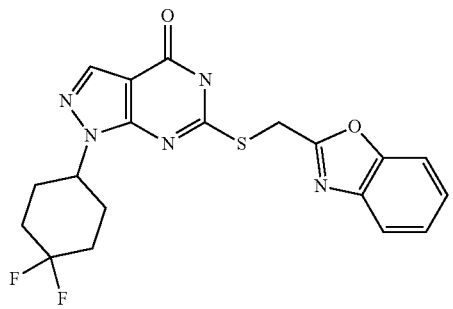

50 mg of 6-chloro-1-(4,4-difluorocyclohexyl)-1,5-dihydro-4H-pyrazolo[3,4-d]pyrimidin-4-one (0.17 mmol) obtained in Preparation Example 9 was dissolved in 3 ml of DMF, and 43 mg of benzo[d]oxazol-2-ylmethanethiol (0.26 mmol) obtained in Preparation Example 2 and 70 mg of potassium carbonate (0.51 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 57 mg of the title compound (0.13 mmol) in 80% yield.

Rf=0.20 (dichloromethane:methanol=20:1, v/v)

$^1$H NMR (500 MHz, DMSO-$d_6$) δ 12.67 (br s, 1H), 7.96 (s, 1H), 7.68-7.71 (m, 2H), 7.34-7.40 (m, 2H), 4.83 (s, 2H), 3.54-3.60 (m, 1H), 1.90-2.08 (m, 6H), 1.74-1.78 (m, 2H)

<Preparation Example 10> Preparation of 6-chloro-1-(tetrahydro-2H-thiopyran-4-yl)-1,5-dihydro-4H-pyrazolo[3,4-d]pyrimidin-4-one

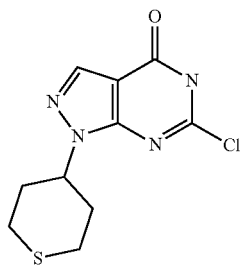 [SMILES: O=c1[nH]c(Cl)nc2c1cnn2C1CCSCC1]

Step 1: Preparation of tert-butyl 2-(tetrahydro-4H-thiopyran-4-ylidene)hydrazine-1-carboxylate

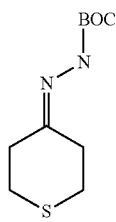

3.3 g of tetrahydro-4H-thiopyran-4-one (28.40 mmol) was dissolved in 60 ml of hexane, and 4.13 g of tert-butyl carbazite (31.24 mmol) was added, followed by stirring under reflux for 3 hours. After completion of the reaction, the mixture was concentrated under reduced pressure to give 6.5 g of the title compound (28.40 mmol) in 100% yield.

Rf=0.15 (hexane:ethyl acetate=3:1, v/v)

$^1$H NMR (500 MHz, DMSO-$d_6$) δ 9.67 (br s, 1H), 2.73-2.76 (m, 2H), 2.65-2.68 (m, 2H), 2.60-2.63 (m, 2H), 2.47-2.50 (m, 2H), 1.43 (s, 9H)

Step 2: Preparation of tert-butyl 2-(tetrahydro-2H-thiopyran-4-yl)hydrazine-1-carboxylate 6.4 g of tert-butyl 2-(tetrahydro-4H-thiopyran-4-ylidene)hydrazine-1-carboxylate (28.40 mmol) obtained in Step 1 was dissolved in 80 ml of THF, and 12 g of sodium triacetoxy borohydride (56.80 mmol) was added, followed by stirring at room temperature for 15 hours. After completion of the reaction, the resultant was extracted with 300 ml of ethyl acetate, washed with 300 ml of an inorganic salt solution, dried over anhydrous sodium sulfate (Na$_2$SO$_4$), and concentrated under reduced pressure. The residue was purified by column chromatography (hexane:ethyl acetate=2:1, v/v) to give 6.5 g of the title compound (27.97 mmol) in 98% yield.

Rf=0.34 (hexane:ethyl acetate=2:1, v/v)

$^1$H NMR (500 MHz, DMSO-$d_6$) δ 8.20 (br s, 1H), 4.28 (br s, 1H), 2.65-2.73 (m, 3H), 2.05-2.49 (m, 2H), 1.93-1.98 (m, 2H), 1.34-1.43 (m, 1H)

Step 3: Preparation of (tetrahydro-2H-thiopyran-4-yl)hydrazine hydrogen chloride 6.5 g of tert-butyl 2-(tetrahydro-2H-thiopyran-4-yl)hydrazine-1-carboxylate (27.97 mmol) obtained in Step 2 was dissolved in 60 ml of methanol, and hydrochloric acid was added, followed by stirring at 50° C. for 3 hours. After completion of the reaction, the mixture was concentrated under reduced pressure to give 4.7 g of the title compound (27.97 mmol) in 94% yield.

$^1$H NMR (500 MHz, DMSO-$d_6$) δ 2.91-2.96 (m, 1H), 2.66-2.72 (m, 2H), 2.57-2.62 (m, 2H), 2.25-2.29 (m, 2H), 1.53-1.60 (m, 2H)

Step 4: Preparation of 4,6-dichloro-1-(tetrahydro-2H-thiopyran-4-yl)-1H-pyrazolo[3,4-d]pyrimidine 5.9 g of 2,4,6-trichloropyrimidine-5-carbaldehyde (27.97 mmol) was dissolved in 60 ml of ethanol, and 4.7 g of (tetrahydro-2H-thiopyran-4-yl)hydrazine hydrogen chloride (27.97 mmol) obtained in Step 3 and 15 ml of N,N-diisopropylethylamine (83.91 mmol) were added at −78° C., followed by stirring for 3 hours. After completion of the reaction, the resultant was extracted with 200 ml of ethyl acetate, washed with 200 ml of an inorganic salt solution, dried over anhydrous sodium sulfate (Na$_2$SO$_4$), and concentrated under reduced pressure. The residue was purified by column chromatography (hexane:ethyl acetate=5:1, v/v) to give 7 g of the title compound (24.20 mmol) in 86% yield.

Rf=0.41 (hexane:ethyl acetate=10:1, v/v)

$^1$H NMR (500 MHz, DMSO-$d_6$) δ 8.57 (s, 1H), 4.78-4.85 (m, 1H), 2.93-2.98 (m, 2H), 2.73-2.78 (m, 2H), 2.15-2.25 (m, 4H)

Step 5: Preparation of 6-chloro-1-(tetrahydro-2H-thiopyran-4-yl)-1,5-dihydro-4H-pyrazolo[3,4-d]pyrimidin-4-one 7 g of 4,6-dichloro-1-(tetrahydro-2H-thiopyran-4-yl)-1H-pyrazolo[3,4-d]pyrimidine (24.20 mmol) obtained in Step 4 above was dissolved in 50 ml of THF, and 25 ml of 2N sodium hydroxide (47.60 mmol) was added, followed by stirring under reflux for 15 hours. After completion of the reaction, the mixture was acidified with 6N hydrochloric acid, and the precipitated solid compound was filtered to give 5.7 g of the title compound (21.05 mmol) in 87% yield.

Rf=0.31 (dichloromethane:methanol=20:1, v/v)

$^1$H NMR (500 MHz, DMSO-$d_6$) δ 13.20 (br s, 1H), 8.11 (s, 1H), 4.56-4.63 (m, 1H), 2.88-2.94 (m, 2H), 2.72-2.76 (m, 2H), 2.10-2.20 (m, 4H)

<Example 9> Preparation of 6-((benzo[d]oxazol-2-ylmethyl)thio)-1-(tetrahydro-2H-thiopyran-4-yl)-1,5-dihydro-4H-pyrazolo[3,4-d]pyrimidin-4-one

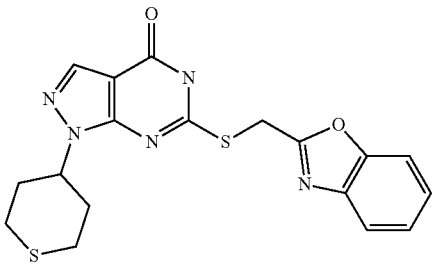

50 mg of 6-chloro-1-(tetrahydro-2H-thiopyran-4-yl)-1,5-dihydro-4H-pyrazolo[3,4-d]pyrimidin-4-one (0.18 mmol) obtained in Preparation Example 10 above was dissolved in 3 ml of DMF, and 46 mg of benzo[d]oxazol-2-ylmethanethiol (0.28 mmol) obtained in Preparation Example 2 and 75 mg of potassium carbonate (0.54 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 62 mg (0.15 mmol) of the title compound in 86% yield.

Rf=0.36 (dichloromethane:methanol=20:1, v/v)

$^1$H NMR (500 MHz, DMSO-d$_6$) δ 12.65 (br s, 1H), 7.94 (s, 1H), 7.69-7.72 (m, 2H), 7.34-7.40 (m, 2H), 4.81 (s, 2H), 4.33-4.39 (m, 1H), 2.68-2.74 (m, 2H), 2.59-2.64 (m, 2H), 1.97-2.04 (m, 2H), 1.88-1.93 (m, 2H)

<Preparation Example 11> Preparation of 6-chloro-1-cyclopropyl-1,5-dihydro-4H-pyrazolo[3,4-d]pyrimidin-4-one

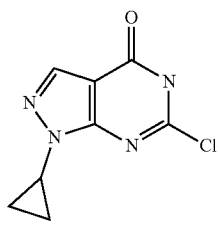 [SMILES: O=c1[nH]c(Cl)nc2c1cnn2C1CC1]

Step 1: Preparation of 4,6-dichloro-1-cyclopropyl-1H-pyrazolo[3,4-d]pyrimidine

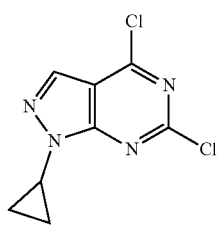 [SMILES: Clc1nc(Cl)c2cnn(C3CC3)c2n1]

1.95 g of 2,4,6-trichloropyrimidine-5-carbaldehyde (9.21 mmol) was dissolved in 30 ml of ethanol, and 1 g of cyclopropyl hydrazine hydrogen chloride (9.21 mmol) and 4.8 ml of N,N-diisopropylethylamine (27.63 mmol) were added at −78° C., followed by stirring for 3 hours. After completion of the reaction, the resultant was extracted with 200 ml of ethyl acetate, washed with 200 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 950 mg of the title compound (4.15 mmol) in 45% yield.

Rf=0.45 (hexane:ethyl acetate=10:1, v/v)

$^1$H NMR (500 MHz, CDCl$_3$) δ 8.10 (s, 1H), 3.88-3.92 (m, 1H), 1.35-1.38 (m, 2H), 1.21-1.25 (m, 2H)

Step 2: Preparation of 6-chloro-1-cyclopropyl-1,5-dihydro-4H-pyrazolo[3,4-d]pyrimidin-4-one 930 mg of 4,6-dichloro-1-cyclopropyl-1H-pyrazolo[3,4-d]pyrimidine (4.06 mmol) obtained in Step 1 was dissolved in 12 ml of THF, and 4 ml of 2N sodium hydroxide (8.12 mmol) was added, followed by stirring under reflux for 15 hours. After completion of the reaction, the mixture was acidified with 6N hydrochloric acid, and the precipitated solid compound was filtered to give 680 mg of the title compound (3.23 mmol) in 80% yield.

Rf=0.28 (dichloromethane:methanol=20:1, v/v)

$^1$H NMR (500 MHz, DMSO-d$_6$) δ 13.20 (br s, 1H), 8.02 (s, 1H), 3.78-3.82 (m, 1H), 1.05-1.15 (m, 4H)

<Example 10> Preparation of 6-((benzo[d]oxazol-2-ylmethyl)thio)-1-cyclopropyl-1,5-dihydro-4H-pyrazolo[3,4-d]pyrimidin-4-one

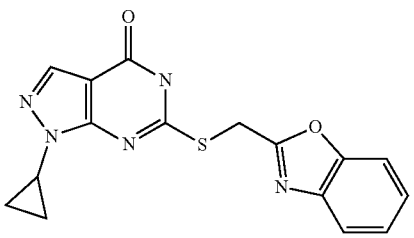 [SMILES: O=c1[nH]c(SCc2nc3ccccc3o2)nc2c1cnn2C1CC1]

50 mg of 6-chloro-1-cyclopropyl-1,5-dihydro-4H-pyrazolo[3,4-d]pyrimidin-4-one (0.24 mmol) obtained in Preparation Example 11 was dissolved in 3 ml of DMF, and 59 mg of benzo[d]oxazol-2-ylmethanethiol (0.36 mmol) obtained in Preparation Example 2 and 100 mg of potassium carbonate (0.72 mmol) were added thereto, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 48 mg of the title compound (0.14 mmol) in 59% yield.

Rf=0.28 (dichloromethane:methanol=20:1, v/v)

$^1$H NMR (500 MHz, DMSO-d$_6$) δ 12.64 (br s, 1H), 7.89 (s, 1H), 7.69-7.72 (m, 2H), 7.34-7.40 (m, 2H), 4.83 (s, 2H), 3.65-3.69 (m, 1H), 0.95-0.99 (m, 2H), 0.90-0.94 (m, 2H)

<Preparation Example 12> Preparation of 6-chloro-1-isopropyl-1,5-dihydro-4H-pyrazolo[3,4-d]pyrimidin-4-one

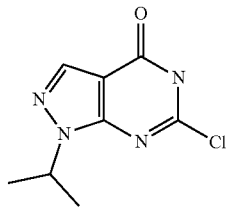

Step 1: Preparation of 4,6-dichloro-1-isopropyl-1H-pyrazolo[3,4-d]pyrimidine

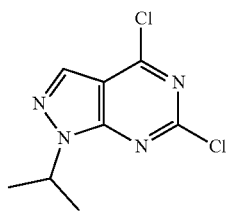

2.22 g of 2,4,6-trichloropyrimidine-5-carbaldehyde (10.49 mmol) was dissolved in 30 ml of ethanol, and 1.16 g of isopropyl hydrazine hydrogen chloride (10.49 mmol) and 5.5 ml of N,N-diisopropylethylamine (31.47 mmol) were added at −78° C., followed by stirring for 3 hours. After completion of the reaction, the resultant was extracted with 200 ml of ethyl acetate, washed with 200 ml of an inorganic salt solution, dried over anhydrous sodium sulfate ($Na_2SO_4$), and concentrated under reduced pressure. The residue was purified by column chromatography (hexane:ethyl acetate=10:1, v/v) to give 2.1 g of the title compound (9.08 mmol) in 87% yield.

Rf=0.48 (hexane:ethyl acetate=10:1, v/v)

$^1$H NMR (500 MHz, CDCl$_3$) δ 8.16 (s, 1H), 5.16-5.22 (m, 1H), 1.60 (d, J=6.7 Hz, 6H)

Step 2: Preparation of 6-chloro-1-isopropyl-1,5-dihydro-4H-pyrazolo[3,4-d]pyrimidin-4-one 2 g of 4,6-dichloro-1-isopropyl-1H-pyrazolo[3,4-d]pyrimidine (8.65 mmol) obtained in Step 1 was dissolved in 12 ml of THF, and 8.6 ml of 2N sodium hydroxide (17.13 mmol) was added, followed by stirring under reflux for 15 hours. After completion of the reaction, the mixture was acidified with 6N hydrochloric acid, and the precipitated solid compound was filtered to give 1.7 g of the title compound (7.99 mmol) in 92% yield.

Rf=0.29 (dichloromethane:methanol=20:1, v/v)

$^1$H NMR (500 MHz, DMSO-d$_6$) δ 13.16 (br s, 1H), 8.08 (s, 1H), 4.85-4.91 (m, 1H), 1.44 (d, J=7.0 Hz, 6H)

<Example 11> Preparation of 6-((benzo[d]oxazol-2-ylmethyl)thio)-1-isopropyl-1,5-dihydro-4H-pyrazolo[3,4-d]pyrimidin-4-one

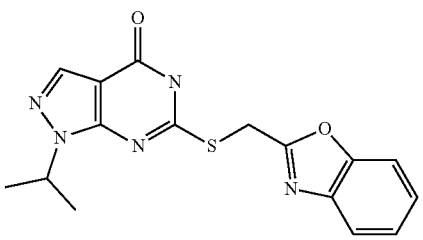 [SMILES: CC(C)n1ncc2c(=O)[nH]c(SCc3nc4ccccc4o3)nc21]

50 mg of 6-chloro-1-isopropyl-1,5-dihydro-4H-pyrazolo[3,4-d]pyrimidin-4-one (0.23 mmol) obtained in Preparation Example 12 was dissolved in 3 ml of DMF, and 58 mg of benzo[d]oxazol-2-ylmethanethiol (0.35 mmol) obtained in Preparation Example 2 and 100 mg of potassium carbonate (0.72 mmol) were added thereto, followed by stirring at 60° C. for 3 hours.

After completion of the reaction, the resultant was extracted with 20 ml of ethyl acetate, washed with 30 ml of an inorganic salt solution, dried over anhydrous sodium sulfate ($Na_2SO_4$), and concentrated under reduced pressure. The residue was purified by column chromatography (dichloromethane:methanol=20:1, v/v) to give 44 mg of the title compound (0.13 mmol) in 56% yield.

Rf=0.44 (dichloromethane:methanol=20:1, v/v)

$^1$H NMR (500 MHz, DMSO-d$_6$) δ 12.60 (br s, 1H), 7.91 (s, 1H), 7.68-7.72 (m, 2H), 7.33-7.39 (m, 2H), 4.79 (s, 2H), 4.70-4.75 (m, 1H), 1.22 (d, J=6.5 Hz, 6H)

<Preparation Example 13> Preparation of 6-chloro-1-cyclohexyl-1,5-dihydro-4H-pyrazolo[3,4-d]pyrimidin-4-one

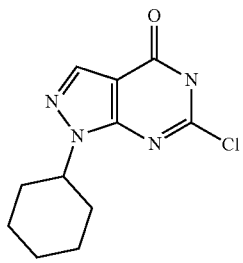 [SMILES: O=c1[nH]c(Cl)nc2c1cnn2C1CCCCC1]

Step 1: Preparation of 4,6-dichloro-1-cyclohexyl-1H-pyrazolo[3,4-d]pyrimidine

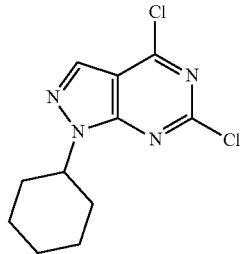 [SMILES: Clc1nc(Cl)c2cnn(C3CCCCC3)c2n1]

4.39 g of 2,4,6-trichloropyrimidine-5-carbaldehyde (20.71 mmol) was dissolved in 50 ml of ethanol, and 3.12 g of cyclohexyl hydrazine hydrogen chloride (20.71 mmol) and 11 ml of N,N-diisopropylethylamine (62.13 mmol) were added at −78° C., followed by stirring for 3 hours. After completion of the reaction, the resultant was extracted with 200 ml of ethyl acetate, washed with 200 ml of an inorganic salt solution, dried over anhydrous sodium sulfate ($Na_2SO_4$), and concentrated under reduced pressure. The residue was purified by column chromatography (hexane:ethyl acetate=10:1, v/v) to give 5.2 g of the title compound (19.18 mmol) in 92% yield.

Rf=0.39 (hexane:ethyl acetate=10:1, v/v)

$^1$H NMR (500 MHz, $CDCl_3$) δ 8.15 (s, 1H), 4.75-4.82 (m, 1H), 2.01-2.08 (m, 2H), 1.93-1.99 (m, 2H), 1.77-1.81 (m, 1H), 1.48-1.57 (m, 2H), 1.30-1.39 (m, 1H), 1.01-1.04 (m, 2H)

Step 2: Preparation of 6-chloro-1-cyclohexyl-1,5-dihydro-4H-pyrazolo[3,4-d]pyrimidin-4-one 5 g of 4,6-dichloro-1-cyclohexyl-1H-pyrazolo[3,4-d]pyrimidine (18.44 mmol) obtained in Step 1 was dissolved in 12 ml of THF, and 19 ml of 2N sodium hydroxide (36.88 mmol) was added, followed by stirring under reflux for 15 hours. After completion of the reaction, the mixture was acidified with 6N hydrochloric acid and the precipitated solid compound was filtered to five 4.6 g of the title compound (18.20 mmol) in 98% yield.

Rf=0.35 (dichloromethane:methanol=20:1, v/v)

$^1$H NMR (500 MHz, DMSO-$d_6$) δ 13.18 (br s, 1H0, 8.07 (s, 1H), 4.46-4.52 (m, 1H), 1.80-1.87 (m, 4H), 1.66-1.69 (m, 1H), 1.40-1.48 (m, 2H), 1.18-1.25 (m, 1H)

<Example 12> Preparation of 6-((benzo[d]oxazol-2-ylmethyl)thio)-1-cyclohexyl-1,5-dihydro-4H-pyrazolol[3,4-d]pyrimidin-4-one

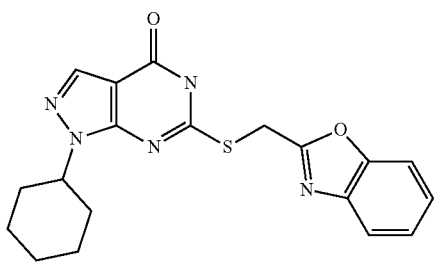 [SMILES: O=c1[nH]c(SCc2nc3ccccc3o2)nc2c1cnn2C1CCCCC1]

50 mg of 6-chloro-1-cyclohexyl-1,5-dihydro-4H-pyrazolo[3,4-d]pyrimidin-4-one (0.20 mmol) obtained in Preparation Example 13 was dissolved in 3 ml of DMF, and 49 mg of benzo[d]oxazol-2-ylmethanethiol (0.30 mmol) obtained in Preparation Example 2 and 83 mg of potassium carbonate (0.60 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate ($Na_2SO_4$), and concentrated under reduced pressure. The residue was purified by column chromatography (dichloromethane:methanol=20:1, v/v) to give 55 mg of the title compound (0.14 mmol) in 72% yield.

Rf=0.27 (dichloromethane:methanol=20:1, v/v)

$^1$H NMR (500 MHz, DMSO-$d_6$) δ 12.61 (br s, 1H), 7.90 (s, 1H), 7.67-7.69 (m, 2H), 7.33-7.39 (m, 2H), 4.79 (s, 2H), 4.25-4.31 (m, 1H), 1.56-1.74 (m, 7H), 1.26-1.34 (m, 2H), 1.16-1.21 (m, 1H)

<Example 13> Preparation of 6-(((6-methylbenzo[d]oxazol-2-yl)methyl)thio)-1-(4,4-difluorocyclohexyl)-1,5-dihydro-4H-pyrazolo[3,4-d]pyrimidin-4-one

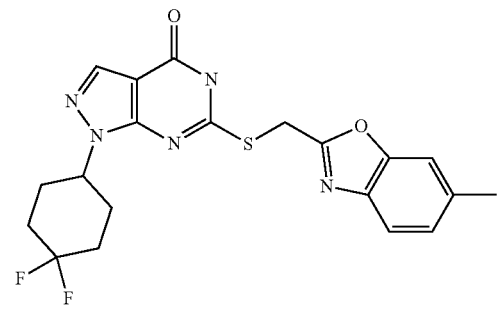 [SMILES: Cc1ccc2nc(CSc3nc4c(cnn4C4CCC(F)(F)CC4)c(=O)[nH]3)oc2c1]

50 mg of 6-chloro-1-(4,4-difluorocyclohexyl)-1,5-dihydro-4H-pyrazolo[3,4-d]pyrimidin-4-one (0.17 mmol) obtained in Preparation Example 9 above was dissolved in 3 ml of DMF, and 61 mg of (6-methylbenzo[d]oxazol-2-yl)methanethiol (0.34 mmol) obtained in Preparation Example 6 and 70 mg of potassium carbonate (0.51 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate ($Na_2SO_4$), and concentrated under reduced pressure. The residue was purified by column chromatography (dichloromethane:methanol=20:1, v/v) to give 60 mg of the title compound (0.14 mmol) in 82% yield.

Rf=0.30 (dichloromethane:methanol=20:1, v/v)

$^1$H NMR (500 MHz, DMSO-$d_6$) δ 12.67 (br s, 1H), 7.96 (s, 1H), 7.55 (d, J=8.0 Hz, 1H), 7.52 (s, 1H), 7.18 (d, J=8.0 Hz, 1H), 4.80 (s, 2H), 4.52-4.58 (m, 1H), 2.42 (s, 3H), 1.89-2.10 (m, 6H), 1.74-1.78 (m, 2H)

<Example 14> Preparation of 6-(((6-methylbenzo[d]oxazol-2-yl)methyl)thio)-1-(tetrahydro-2H-pyran-4-yl)-1,5-dihydro-4H-pyrazolo[3,4-d]pyrimidin-4-one

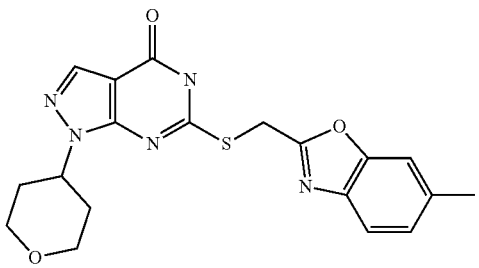 [SMILES: Cc1ccc2nc(CSc3nc4c(cnn4C4CCOCC4)c(=O)[nH]3)oc2c1]

50 mg of 6-chloro-1-(tetrahydro-2H-pyran-4-yl)-1,5-dihydro-4H-pyrazolo[3,4-d]pyrimidin-4-one (0.20 mmol) obtained in Preparation Example 1 above was dissolved in 3 ml of DMF, and 72 mg of (6-methylbenzo[d]oxazol-2-yl)methanethiol (0.40 mmol) obtained in Preparation Example 6 above and 83 mg of potassium carbonate (0.60 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 51 mg of the title compound (0.13 mmol) in 64% yield.

Rf=0.40 (dichloromethane:methanol=20:1, v/v)

$^1$H NMR (500 MHz, DMSO-d$_6$) δ 12.65 (br s, 1H), 7.95 (s, 1H), 7.54 (d, J=8.2 Hz, 1H), 7.52 (s, 1H), 7.17 (d, J=8.2 Hz, 1H), 4.77 (s, 2H), 4.51-4.57 (m, 1H), 3.86-3.89 (m, 2H), 3.37-3.41 (m, 2H), 2.42 (s, 3H), 1.90-1.98 (m, 2H), 1.52-1.55 (m, 2H)

<Example 15> Preparation of 6-(((6-methylbenzo[d]oxazol-2-yl)methyl)thio)-1-(tetrahydro-2H-thiopyran-4-yl)-1,5-dihydro-4H-pyrazolo[3,4-d]pyrimidin-4-one

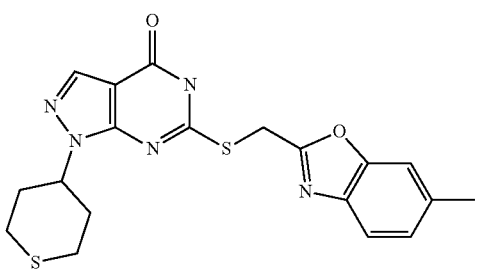

50 mg of 6-chloro-1-(tetrahydro-2H-thiopyran-4-yl)-1,5-dihydro-4H-pyrazolo[3,4-d]pyrimidin-4-one (0.18 mmol) obtained in Preparation Example 10 above was dissolved in 3 ml of DMF, and 64 mg of (6-methylbenzo[d]oxazol-2-yl)methanethiol (0.36 mmol) obtained in Preparation Example 6 above and 75 mg of potassium carbonate (0.54 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 59 mg of the title compound (0.14 mmol) in 78% yield.

Rf=0.33 (dichloromethane:methanol=20:1, v/v)

$^1$H NMR (500 MHz, DMSO-d$_6$) δ 12.64 (br s, 1H), 7.95 (s, 1H), 7.56 (d, J=7.9 Hz, 1H), 7.52 (s, 1H), 7.18 (d, J=7.9 Hz, 1H), 4.78 (s, 2H), 4.33-4.39 (m, 1H), 2.70-2.75 (m, 2H), 2.62-2.66 (m, 2H), 2.42 (s, 3H), 1.97-2.05 (m, 2H), 1.89-1.93 (m, 2H)

<Example 16> Preparation of 6-(((6-methylbenzo[d]oxazol-2-yl)methyl)thio)-1-cyclohexyl-1,5-dihydro-4H-pyrazolo[3,4-d]pyrimidin-4-one

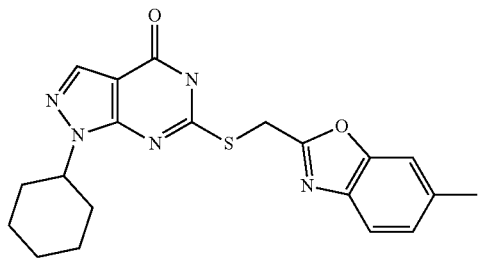 [SMILES: Cc1ccc2nc(CSc3nc4c(cnn4C4CCCCC4)c(=O)[nH]3)oc2c1]

50 mg of 6-chloro-1-cyclohexyl-1,5-dihydro-4H-pyrazolo[3,4-d]pyrimidin-4-one (0.20 mmol) obtained in Preparation Example 13 was dissolved in 3 ml of DMF, and 72 mg of (6-methylbenzo[d]oxazol-2-yl)methanethiol (0.40 mmol) obtained in Preparation Example 6 and 83 mg of potassium carbonate (0.60 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 55 mg of the title compound (0.14 mmol) in 70% yield.

Rf=0.45 (dichloromethane:methanol=20:1, v/v)

$^1$H NMR (500 MHz, DMSO-d$_6$) δ 12.62 (br s, 1H), 7.90 (s, 1H), 7.54 (d, J=8.1 Hz, 1H), 7.50 (s, 1H), 7.17 (d, J=8.1 Hz, 1H), 4.76 (s, 2H), 4.25-4.32 (m, 1H), 2.41 (s, 3H), 1.56-1.75 (m, 7H), 1.27-1.36 (m, 2H), 1.15-1.23 (m, 1H)

<Example 17> Preparation of 6-(((6-methylbenzo[d]oxazol-2-yl)methyl)thio)-1-cyclopropyl-1,5-dihydro-4H-pyrazolo[3,4-d]pyrimidin-4-one

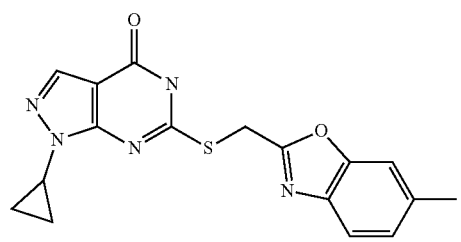 [SMILES: Cc1ccc2nc(CSc3nc4c(cnn4C4CC4)c(=O)[nH]3)oc2c1]

50 mg of 6-chloro-1-cyclopropyl-1,5-dihydro-4H-pyrazolo[3,4-d]pyrimidin-4-one (0.24 mmol) obtained in Preparation Example 11 was dissolved in 3 ml of DMF, and 86 mg of (6-methylbenzo[d]oxazol-2-yl)methanethiol (0.48 mmol) obtained in Preparation Example 6 and 100 mg of potassium carbonate (0.72 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 50 mg of the title compound (0.14 mmol) in 59% yield.

Rf=0.29 (dichloromethane:methanol=20:1, v/v)

$^1$H NMR (500 MHz, DMSO-d$_6$) δ 12.64 (br s, 1H), 7.89 (s, 1H), 7.57 (d, J=8.2 Hz, 1H), 7.53 (s, 1H), 7.17 (d, J=8.2 Hz, 1H), 4.81 (s, 2H), 3.66-3.71 (m, 1H), 2.43 (s, 3H), 0.91-1.01 (m, 4H)

<Example 18> Preparation of 6-(((6-methylbenzo[d]oxazol-2-yl)methyl)thio)-1-isopropyl-1,5-dihydro-4H-pyrazolo[3,4-d]pyrimidin-4-one

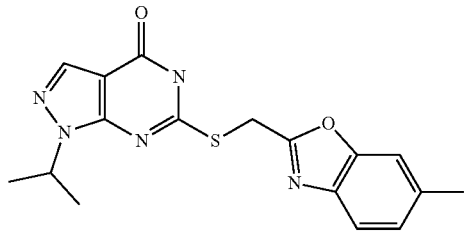 [SMILES: Cc1ccc2nc(CSc3nc4c(cnn4C(C)C)c(=O)[nH]3)oc2c1]

50 mg of 6-chloro-1-isopropyl-1,5-dihydro-4H-pyrazolo[3,4-d]pyrimidin-4-one (0.24 mmol) obtained in Preparation Example 12 was dissolved in 3 ml of DMF, and 82 mg of (6-methylbenzo[d]oxazol-2-yl)methanethiol (0.46 mmol) obtained in Preparation Example 6 above and 95 mg of potassium carbonate (0.69 mmol) were added, followed by stirring at 60° C. for 3 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 56 mg of the title compound (0.16 mmol) in 68% yield.

Rf=0.21 (dichloromethane:methanol=20:1, v/v)

$^1$H NMR (500 MHz, DMSO-d$_6$) δ 12.60 (br s, 1H), 7.92 (s, 1H), 7.55 (d, J=8.2 Hz, 1H), 7.52 (s, 1H), 7.17 (d, J=8.2 Hz, 1H), 4.76 (s, 2H), 4.71-4.75 (m, 1H), 2.42 (s, 3H), 1.23 (d, J=6.5 Hz, 6H)

<Preparation Example 14> Preparation of 1-(benzo[d]oxazol-2-yl)ethan-1-thiol

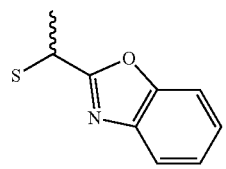

1 g of 2-aminophenol (9.16 mmol) was dissolved in 20 ml of toluene, and 1 ml of thiolactic acid (9.16 mmol) was added, followed by stirring under reflux for 5 hours. Then, 1.6 g of p-toluenesulphonic acid (9.16 mmol) was added and stirred under reflux for 15 hours. After completion of the reaction, the resultant was extracted with 50 ml of ethyl acetate, washed with 50 ml of an inorganic salt solution, dried over anhydrous sodium sulfate (Na$_2$SO$_4$), and concentrated under reduced pressure. The residue was purified by column chromatography (hexane:ethyl acetate=2:1, v/v) to give 240 mg of the title compound (1.33 mmol) in 15% yield.

Rf=0.50 (hexane:ethyl acetate=2:1, v/v)

$^1$H NMR (500 MHz, CDCl$_3$) δ 7.71-7.73 (m, 1H), 7.53-7.55 (m, 1H), 7.35-7.37 (m, 2H), 4.34-4.39 (m, 1H), 2.42 (d, J=7.4 Hz, 1H), 1.90 (d, J=6.9 Hz, 2H)

<Example 19> Preparation of 6-((1-(benzo[d]oxazol-2-yl)ethyl)thio)-1-phenyl-1,5-dihydro-4H-pyrazolo[3,4-d]pyrimidin-4-one

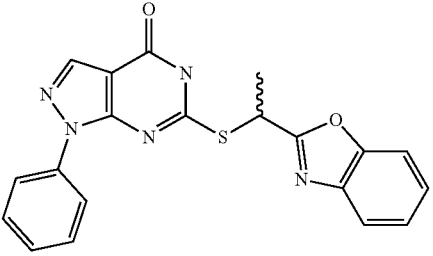 [SMILES: CC(Sc1nc2c(cnn2-c2ccccc2)c(=O)[nH]1)c1nc2ccccc2o1]

50 mg of 6-chloro-1-phenyl-1,5-dihydro-4H-pyrazolo[3,4-d]pyrimidin-4-one (0.20 mmol) obtained in Preparation Example 3 was dissolved in 3 ml of DMF, and 55 mg of 1-(benzo[d]oxazol-2-yl)ethan-1-thiol (0.30 mmol) obtained in Preparation Example 14 and 83 mg of potassium carbonate (0.61 mmol) were added, followed by stirring 60° C. for 1 hour. After completion of the reaction, the resultant was extracted was performed with 20 ml of ethyl acetate, washed with 20 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 49 mg of the title compound (0.13 mmol) in 63% yield.

Rf=0.37 (dichloromethane:methanol=20:1, v/v)

$^1$H NMR (500 MHz, DMSO-d$_6$) δ 12.90 (br s, 1H), 8.25 (s, 1H), 7.96-7.99 (m, 2H), 7.74 (d, J=7.1 Hz, 1H), 7.70 (d, J=7.1 Hz, 1H), 7.51-7.54 (m, 2H), 7.34-7.40 (m, 3H), 5.38-5.42 (m, 1H), 1.89 (d, J=5.1 Hz, 3H)

<Example 20> Preparation of 6-((1-benzo[d]oxa-zol-2-yl)ethyl)thio)-1-(4,4-difluorocyclohexyl)-1,5-dihydro-4H-pyrazolo[3,4-d]pyrimidin-4-one

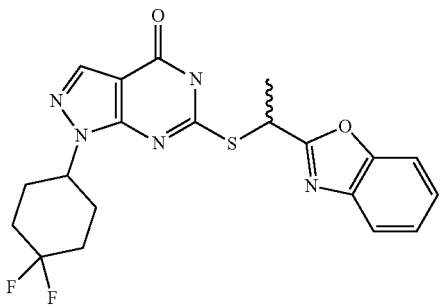 [SMILES: CC(Sc1nc2c(cnn2C2CCC(F)(F)CC2)c(=O)[nH]1)c1nc2ccccc2o1]

25 mg of 6-chloro-1-(4,4-difluorocyclohexyl)-1,5-dihydro-4H-pyrazolo[3,4-d]pyrimidin-4-one (0.08 mmol) obtained in Preparation Example 9 above was dissolved in 3 ml of DMF, and 55 mg of 1-(benzo[d]oxazol-2-yl)ethan-1-thiol (0.30 mmol) obtained in Preparation Example 14 above and 36 mg of potassium carbonate (0.24 mmol) were added, followed by stirring at 60° C. for 1 hour. After completion of the reaction, the resultant was extracted with 10 ml of ethyl acetate, washed with 40 ml of an inorganic salt solution, dried over anhydrous sodium sulfate ($Na_2SO_4$), and concentrated under reduced pressure. The residue was purified by column chromatography (dichloromethane:methanol=20:1, v/v) to give 30 mg of the title compound (0.07 mmol) in 80% yield.

Rf=0.33 (dichloromethane:methanol=20:1, v/v)

$^1$H NMR (500 MHz, DMSO-$d_6$) δ 12.65 (br s, 1H), 7.97 (s, 1H), 7.71-7.74 (m, 2H), 7.36-7.42 (m, 2H), 5.43 (q, J=7.4 Hz, 1H), 4.55-4.61 (m, 1H), 2.07-2.17 (m, 4H), 1.96-2.01 (m, 2H), 1.89 (d, J=7.4 Hz, 3H), 1.83-1.90 (m, 1H), 1.74-1.76 (m, 1H)

<Example 21> Preparation of 6-((1-benzo[d]oxa-zol-2-yl)ethyl)thio)-1-(tetrahydro-2H-pyran-4-yl)-1,5-dihydro-4H-pyrazolo[3,4-d]pyrimidin-4-one

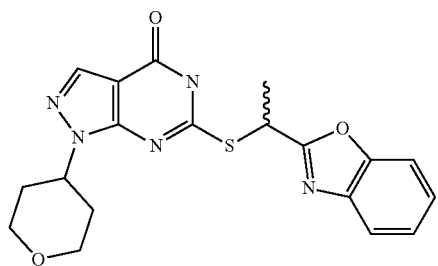 [SMILES: CC(Sc1nc2c(cnn2C2CCOCC2)c(=O)[nH]1)c1nc2ccccc2o1]

30 mg of 6-chloro-1-(tetrahydro-2H-pyran-4-yl)-1,5-dihydro-4H-pyrazolo[3,4-d]pyrimidin-4-one (0.12 mmol) obtained in Preparation Example 1 above was dissolved in 3 ml of DMF, and 42 mg of 1-(benzo[d]oxazol-2-yl)ethan-1-thiol (0.23 mmol) obtained in Preparation Example 14 above and 50 mg of potassium carbonate (0.37 mmol) were added, followed by stirring at 60° C. for 1 hour. After completion of the reaction, the resultant was extracted with 10 ml of ethyl acetate, washed with 40 ml of an inorganic salt solution, dried over anhydrous sodium sulfate ($Na_2SO_4$), and concentrated under reduced pressure. The residue was purified by column chromatography (dichloromethane:methanol=20:1, v/v) to give 17 mg of the title compound (0.04 mmol) in 36% yield.

Rf=0.33 (dichloromethane:methanol=20:1, v/v)

$^1$H NMR (500 MHz, DMSO-$d_6$) δ 12.63 (br s, 1H), 7.96 (s, 1H), 7.71-7.73 (m, 2H), 7.35-7.40 (m, 2H), 5.37 (q, J=7.3 Hz, 1H), 4.50-4.56 (m, 1H), 3.87-3.93 (m, 2H), 3.36-3.45 (m, 2H), 1.90-2.04 (m, 2H), 1.87 (d, J=7.3 Hz, 3H), 1.63-1.66 (m, 1H), 1.47-1.51 (m, 1H)

<Preparation Example 15> Preparation of 1-(6-methylbenzo[d]oxazol-2-yl)ethan-1-thiol

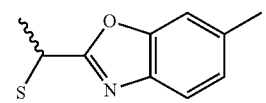

1 g of 2-amino-5-methylphenol (8.12 mmol) was dissolved in 10 ml of toluene, and 0.72 ml of thiolactic acid (8.13 mmol) was added, followed by stirring at 100° C. for 24 hours. After completion of the reaction, the residue was purified by column chromatography (hexane:ethyl acetate=10:1, v/v) to give 384 mg of the title compound (1.83 mmol) in 22% yield.

Rf=0.48 (hexane:ethyl acetate=5:1, v/v)

$^1$H NMR (500 MHz, $CDCl_3$) δ 7.59 (d, J=8.2 Hz, 1H), 7.33 (s, 1H), 7.17 (d, J=8.2 Hz, 1H), 4.31-4.37 (m, 1H), 2.50 (s, 3H), 2.40 (d, J=7.5 Hz, 1H), 1.88 (d, J=7.1 Hz, 3H)

<Example 22> Preparation of 1-(4,4-difluorocyclo-hexyl)-6-((1-(6-methylbenzo[d]oxazol-2-yl)ethyl)thio)-1,5-dihydro-4H-pyrazolo[3,4-d]pyrimidin-4-one

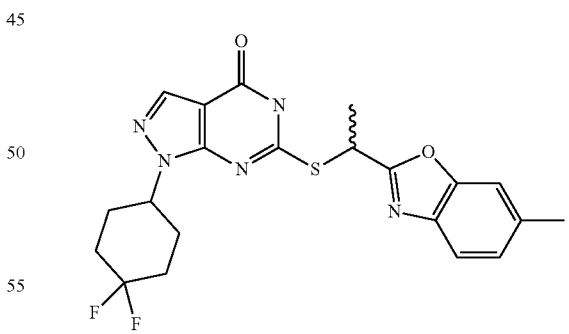

50 mg of 6-chloro-1-(4,4-difluorocyclohexyl)-1,5-dihydro-4H-pyrazolo[3,4-d]pyrimidin-4-one (0.17 mmol) obtained in Preparation Example 9 above was dissolved in 3 ml of DMF, and 72 mg of 1-(6-methylbenzo[d]oxazol-2-yl)ethan-1-thiol (0.35 mmol) obtained in Preparation Example 15 above and 72 mg of potassium carbonate (0.52 mmol) were added, followed by stirring at 60° C. for 1 hour. After completion of the reaction, the resultant was extracted with 10 ml of ethyl acetate, washed with 40 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 60 mg of the title compound (0.13 mmol) in 75% yield.

Rf=0.18 (dichloromethane:methanol=20:1, v/v)

$^1$H NMR (500 MHz, DMSO-d$_6$) δ 12.67 (br s, 1H), 7.98 (s, 1H), 7.59 (d, J=7.9 Hz, 1H), 7.53 (s, 1H), 7.20 (d, J=7.9 Hz, 1H), 5.40 (q, J=7.0 Hz, 1H), 4.54-4.59 (m, 1H), 2.42 (s, 3H), 1.91-2.19 (m, 7H), 1.87 (d, J=7.0 Hz, 3H), 1.73-1.76 (m, 1H)

<Example 23> Preparation of 6-((1-(6-methylbenzo[d]oxazol-2-yl)ethyl)thio)-1-(tetrahydro-2H-pyran-4-yl)-1,5-dihydro-4H-pyrazolo[3,4-d]pyrimidin-4-one

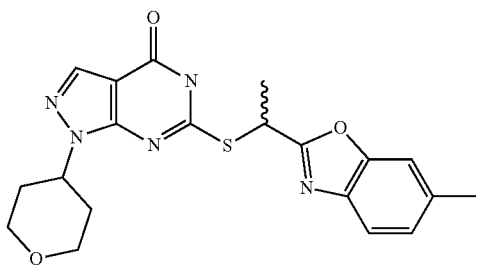 [SMILES: Cc1ccc2nc(C(C)Sc3nc4c(cnn4C4CCSCC4)c(=O)[nH]3)oc2c1]

50 mg of 6-chloro-1-(tetrahydro-2H-pyran-4-yl)-1,5-dihydro-4H-pyrazolo[3,4-d]pyrimidin-4-one (0.20 mmol) obtained in Preparation Example 1 above was dissolved in 3 ml of DMF, and 84 mg of 1-(6-methylbenzo[d]oxazol-2-yl)ethan-1-thiol (0.40 mmol) obtained in Preparation Example 15 above and 83 mg of potassium carbonate (0.60 mmol) were added, followed by stirring at 60° C. for 1 hour. After completion of the reaction, the resultant was extracted with 10 ml of ethyl acetate, washed with 40 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 50 mg of the title compound (0.12 mmol) in 66% yield.

Rf=0.11 (dichloromethane:methanol=20:1, v/v)

$^1$H NMR (500 MHz, DMSO-d$_6$) δ 12.62 (br s, 1H), 7.96 (s, 1H), 7.59 (d, J=8.2 Hz, 1H), 7.53 (s, 1H), 7.19 (d, J=8.2 Hz, 1H), 5.35 (q, J=7.1 Hz, 1H), 4.51-4.57 (m, 1H), 3.98-3.95 (m, 2H), 3.38-3.47 (m, 2H), 2.42 (s, 3H), 1.87-2.06 (m, 2H), 1.86 (d, J=7.1 Hz, 3H), 1.65-1.68 (m, 1H), 1.48-1.51 (m, 1H)

<Example 24> Preparation of 6-((1-(6-methylbenzo[d]oxazol-2-yl)ethyl)thio)-1-(tetrahydro-2H-thiopyran-4-yl)-1,5-dihydro-4H-pyrazolo[3,4-d]pyrimidin-4-one

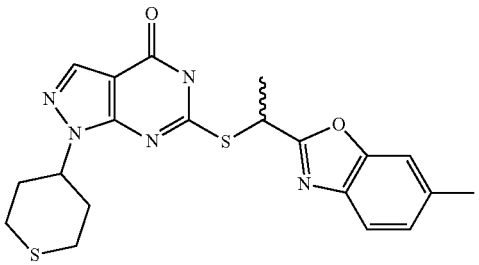

50 mg of 6-chloro-1-(tetrahydro-2H-thiopyran-4-yl)-1,5-dihydro-4H-pyrazolo[3,4-d]pyrimidin-4-one (0.18 mmol) obtained in Preparation Example 10 above was dissolved in 3 ml of DMF, and 77 mg of 1-(6-methylbenzo[d]oxazol-2-yl)ethane-1-thiol (0.37 mmol) obtained in Preparation Example 15 above and 75 mg of potassium carbonate (0.54 mmol) were added, followed by stirring at 60° C. for 1 hour. After completion of the reaction, the resultant was extracted with 10 ml of ethyl acetate, washed with 40 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 62 mg of the title compound (0.14 mmol) in 77% yield.

Rf=0.19 (dichloromethane:methanol=20:1, v/v)

$^1$H NMR (500 MHz, DMSO-d$_6$) δ 12.61 (br s, 1H), 7.96 (s, 1H), 7.60 (d, J=7.9 Hz, 1H), 7.53 (s, 1H), 7.20 (d, J=7.9 Hz, 1H), 5.37 (q, J=7.0 Hz, 1H), 4.34-4.40 (m, 1H), 2.66-2.82 (m, 4H), 2.42 (s, 3H), 1.96-2.12 (m, 3H), 1.88-1.91 (m, 1H), 1.86 (d, J=7.0 Hz, 3H)

<Preparation Example 16> Preparation of (5-phenylbenzo[d]oxazol-2-yl)methanethiol

Step 1: Preparation of 5-bromo-2-methylbenzo[d]oxazole

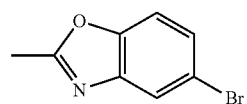

220 mg of 2-amino-4-bromophenol (1.17 mmol) was dissolved in 0.43 ml of triethylosoacetate (2.34 mmol) and 7 μl of acetic acid (0.12 mmol), followed by stirring at 100° C. for 0.5 hours. After completion of the reaction, the resultant was extracted with 10 ml of ethyl acetate, washed with 10 ml of an inorganic salt solution, dried over anhydrous sodium sulfate (Na$_2$SO$_4$), and concentrated under reduced pressure. The residue was purified by column chromatography (hexane:ethylacetate=5:1, v/v) to give 228 mg of the title compound (1.07 mmol) in 92% yield.

Rf=0.36 (hexane:ethyl acetate=5:1, v/v)

$^1$H NMR (500 MHz, CDCl$_3$) δ 7.81 (d, J=1.8 Hz, 1H), 7.44 (dd, J=8.6, 1.4 Hz, 1H), 7.37 (d, J=8.6 Hz, 1H), 2.67 (s, 3H)

Step 2: Preparation of 2-methyl-5-phenylbenzo[d]oxazole 210 mg of 5-bromo-2-methylbenzo[d]oxazole (0.99 mmol) obtained in Step 1 was dissolved in a mixture of dioxane and water, and 181 mg of phenylboronic acid (1.48 mmol), 40 mg of Pd(dppf))Cl$_2$ (0.05 mmol) and 410 mg of potassium carbonate (2.97 mmol) were added, followed by stirring under reflux for 1 hour. After completion of the reaction, the resultant was extracted with 20 ml of ethyl acetate, washed with 20 ml of an inorganic salt solution, dried over anhydrous sodium sulfate (Na$_2$SO$_4$), and concentrated under reduced pressure. The residue was purified by column chromatography (hexane:ethyl acetate=4:1, v/v) to give 199 mg of the title compound (0.95 mmol) in 96% yield.

Rf=0.25 (hexane:ethyl acetate=5:1, v/v)

$^1$H NMR (500 MHz, CDCl$_3$) δ 7.87 (s, 1H), 7.64 (d, J=7.3 Hz, 2H), 7.54-7.55 (m, 2H), 7.48 (dd, J=7.5, 7.3 Hz, 2H), 7.38 (dd, J=7.3, 7.3 Hz, 1H), 2.69 (s, 3H)

Step 3: Preparation of 2-(bromomethyl)-5-phenylbenzo[d]oxazole 199 mg of 2-methyl-5-phenylbenzo[d]oxazole (0.95 mmol) prepared in Step 2 was dissolved in chlorobenzene, and 169 mg of N-bromosuccinimide (0.95 mmol), 31 mg of AIBN (azobisisobutylonitrile) (0.19 mmol) was added, followed by stirring under reflux for 2 hours.

After completion of the reaction, the residue was purified by column chromatography (hexane:ethylacetate=8:1, v/v) to give 110 mg of the title compound (0.38 mmol) in 40% yield.

Rf=0.30 (hexane:ethyl acetate=8:1, v/v)

$^1$H NMR (500 MHz, CDCl$_3$) δ 7.94 (s, 1H), 7.61-7.66 (m, 4H), 7.49 (dd, J=7.7, 7.4 Hz, 2H), 7.40 (dd, J=7.4, 7.4 Hz, 1H), 4.64 (s, 2H)

Step 4: Preparation of S-((5-phenylbenzo[d]oxazol-2-yl)methyl)ethanethioate 100 mg of 2-(bromomethyl)-5-phenylbenzo[d]oxazole (0.34 mmol) prepared in Step 3 was dissolved in acetone, and 59 mg of potassium thioacetate (0.52 mmol) was added, followed by stirring at 50° C. for 1 hour. After completion of the reaction, the resultant was extracted with 20 ml of ethyl acetate, washed with 20 ml of an inorganic salt solution, and dried over anhydrous sodium sulfate (Na$_2$SO$_4$) to give 95 mg of the title compound (0.33 mmol) in 96% yield.

Rf=0.23 (hexane:ethyl acetate=6:1, v/v)

$^1$H NMR (500 MHz, CDCl$_3$) δ 7.90 (s, 1H), 7.58-7.62 (m, 4H), 7.48 (dd, J=7.7, 7.4 Hz, 2H), 7.39 (dd, J=7.4, 7.4 Hz, 1H), 4.44 (s, 2H), 2.47 (s, 3H)

Step 5: Preparation of (5-phenylbenzo[d]oxazol-2-yl)methanethiol 90 mg of S-((5-phenylbenzo[d]oxazol-2-yl)methyl)ethanoate (0.32 mmol) prepared in Step 4 was dissolved in 6 ml of a mixture of methanol and water, and 131 mg of potassium carbonate (0.95 mmol) was added, followed by stirring at room temperature for 1 hour. After completion of the reaction, the resultant was extracted with 20 ml of ethyl acetate, washed with 20 ml of an inorganic salt solution, and dried over anhydrous sodium sulfate (Na$_2$SO$_4$) to give 75 mg of the title compound (0.31 mmol) in 99% yield.

Rf=0.14 (hexane:ethyl acetate=3:1, v/v)

$^1$H NMR (500 MHz, CDCl$_3$) δ 7.90 (s, 1H), 7.58-7.63 (m, 4H), 7.49 (dd, J=7.8, 7.5 Hz, 2H), 7.39 (dd, J=7.5, 7.5 Hz, 1H), 4.01 (d, J=8.1 Hz, 2H), 2.27 (t, J=8.1 Hz, 1H)

<Example 25> Preparation of 1-phenyl-6-(((5-phenylbenzo[d]oxazol-2-yl)methyl)thio)-1,5-dihydro-4H-pyrazolo[3,4-d]pyrimidin-4-one

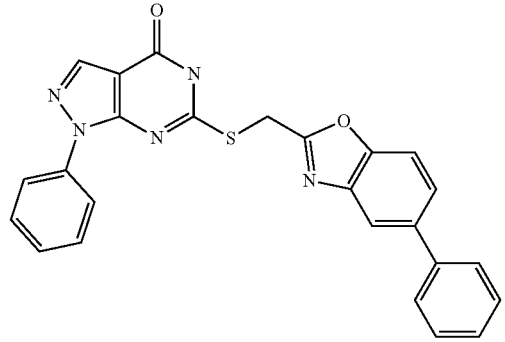 [SMILES: O=c1[nH]c(SCc2nc3cc(-c4ccccc4)ccc3o2)nc2c1cnn2-c1ccccc1]

38 mg of 6-chloro-1-phenyl-1,5-dihydro-4H-pyrazolo[3,4-d]pyrimidin-4-one (0.15 mmol) obtained in Preparation Example 3 was dissolved in 3 ml of DMF, and 75 mg of (5-phenylbenzo[d]oxazol-2-yl)methanethiol (0.31 mmol) obtained in Preparation Example 16 and 128 mg of potassium carbonate (0.93 mmol) were added, followed by stirring at 60° C. for 1 hour. After completion of the reaction, the resultant was extracted with 10 ml of ethyl acetate, washed with 40 ml of an inorganic salt solution, dried over anhydrous sodium sulfate (Na$_2$SO$_4$), and concentrated under reduced pressure. The residue was purified by column chromatography (dichloromethane:methanol=20:1, v/v) to give 50 mg of the title compound (0.11 mmol) in 71% yield.

Rf=0.35 (dichloromethane:methanol=20:1, v/v)

$^1$H NMR (500 MHz, DMSO-d$_6$) δ 12.96 (br s, 1H), 8.24 (s, 1H), 7.95-7.97 (m, 3H), 7.78 (d, J=8.7 Hz, 1H), 7.65-7.69 (m, 3H), 7.45-7.51 (m, 4H), 7.35-7.39 (m, 2H), 4.86 (s, 2H)

<Preparation Example 17> Preparation of 1-phenyl-6-thioxo-1,5,6,7-tetrahydro-4H-pyrazolo[3,4-d]pyridin-4-one

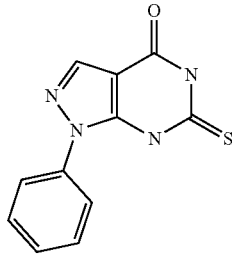 [SMILES: O=c1[nH]c(=S)[nH]c2c1cnn2-c1ccccc1]

Step 1: Preparation of ethyl 5-amino-1-phenyl-1H-pyrazole-4-carboxylate

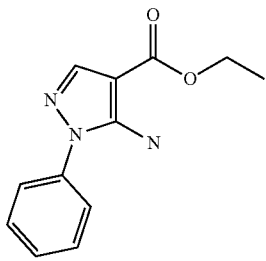 [SMILES: CCOC(=O)c1cnn(-c2ccccc2)c1N]

5 g of ethyl (E)-2-cyano-3-ethoxyacrylate (30 mmol) was dissolved in 100 ml of ethanol, and 3.9 g of phenyl hydrazine (36 mmol) was added, followed by stirring under reflux for 15 hours. After completion of the reaction, the reaction solution was concentrated under reduced pressure, and the residue was purified by column chromatography (hexane:ethylacetate=10:1, v/v) to give 7 g of the title compound (30 mmol) in 100% yield.

Rf=0.30 (hexane:ethyl acetate=4:1, v/v)

$^1$H NMR (500 MHz, CDCl$_3$) δ 7.75 (s, 1H), 7.55-7.45 (m, 4H), 7.41-7.34 (m, 1H), 5.36 (br s, 2H), 4.28 (q, J=7.1 Hz, 2H), 1.35 (t, J=7.1 Hz, 3H)

Step 2: Preparation of 1-phenyl-6-thioxo-1,5,6,7-tetrahydro-4H-pyrazolo[3,4-d]pyrimidin-4-one 7 g of ethyl 5-amino-1-phenyl-1H-pyrazole-4-carboxylate (30 mmol) obtained in Step 1 was dissolved in 60 ml of tetrahydrofuran, and 4.95 ml of benzoyl isothiocyanate (39 mmol) was added, following by stirring under reflux for 13 hours. Then, 92 ml of 2N sodium hydroxide was added and the mixture was stirred under reflux for 30 minutes. After completion of the reaction, it is neutralized with 2N hydrochloric acid and acetic acid is added to precipitate a solid. The residue was purified with water, hexane, and dichloromethane to give 4.48 g of the title compound (18.34 mmol) in 60% yield.

Rf=0.15 (dichloromethane:methanol=10:1, v/v)

$^1$H NMR (500 MHz, DMSO-d$_6$) δ 11.27 (br s, 1H), 10.46 (s, 1H), 8.13 (s, 1H), 7.87 (d, J=7.6 Hz, 2H), 7.68-7.47 (m, 3H)

<Preparation Example 18> Preparation of 2-(chloromethyl)-4-methylbenzo[d]oxazole

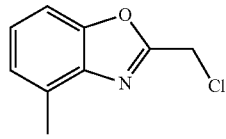

300 mg of 2-amino-3-methylphenol (2.44 mmol) was dissolved in 6 ml of xylene, and 0.29 ml of chloroacetyl chloride (3.66 mmol) was slowly added, followed by stirring at 0° C. for 2 hours. Thereafter, 0.37 ml of triethylamine (2.68 mmol) was added, and the mixture was stirred under reflux for 15 hours. After completion of the reaction, the resultant was extracted with 20 ml of ethyl acetate, washed with 30 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 363 mg of the title compound (2.0 mmol) in 82% yield.

Rf=0.5 (hexane:ethyl acetate=10:1, v/v)

$^1$H NMR (500 MHz, CDCl$_3$) δ 7.36 (d, J=8.2 Hz, 1H), 7.28-7.24 (m, 1H), 7.15 (d, J=7.4 Hz, 1H), 4.77 (s, 2H), 2.62 (s, 3H).

<Example 26> Preparation of 6-(((4-methylbenzo[d]oxazol-2-yl)methyl)thio)-1-phenyl-1,5-dihydro-4H-pyrazole[3,4-d]pyrimidin-4-one

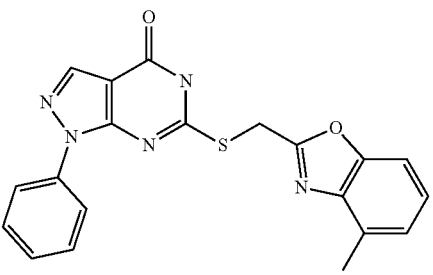 [SMILES: Cc1cccc2oc(CSc3nc4c(cnn4-c4ccccc4)c(=O)[nH]3)nc12]

40 mg of 1-phenyl-6-thioxo-1,5,6,7-tetrahydro-4H-pyrazolo[3,4-d]pyridin-4-one (0.16 mmol) obtained in Preparation Example 17 was dissolved in methanol, and 33 mg of 2-(chloromethyl)-4-methylbenzo[d]oxazole (0.18 mmol) obtained in Preparation Example 18 and 0.1 ml of 2N sodium hydroxide were added, followed by stirring under reflux for 12 hours. After completion of the reaction, the resultant was concentrated under reduced pressure and purified by column chromatography (hexane:ethyl acetate=10:1, v/v) to give 55 mg of the title compound (0.14 mmol) in 86% yield.

Rf=0.3 (hexane:ethyl acetate=10:1, v/v)

$^1$H NMR (500 MHz, DMSO-d$_6$) δ 8.22 (s, 1H), 8.06 (d, J=8.1 Hz, 2H), 7.53-7.44 (m, 3H), 7.40-7.38 (m, 1H), 7.26-7.23 (m, 1H), 7.15 (d, J=7.3 Hz, 1H), 4.82 (s, 2H), 2.48 (s, 3H)

<Preparation Example 19> Preparation of 5-(tert-butyl)-2-(chloromethyl)benzo[d]oxazole

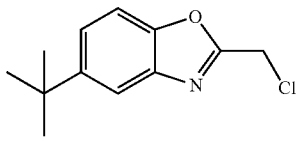

200 mg of 2-amino-4-(tert-butyl)phenol (1.21 mmol) was dissolved in 5 ml of xylene, and 0.14 ml of chloroacetyl chloride (1.81 mmol) was slowly added, followed by stirring at 0° C. for 2 hours. Thereafter, 0.19 ml of triethylamine (1.33 mmol) was added and stirred under reflux for 15 hours. After completion of the reaction, the resultant was extracted with 20 ml of ethyl acetate, washed with 20 ml of an inorganic salt solution, dried over anhydrous sodium sulfate ($Na_2SO_4$), and concentrated under reduced pressure. The residue was purified by column chromatography (hexane:ethyl acetate=20:1, v/v) to give 154 mg of the title compound (0.69 mmol) in 57% yield.

Rf=0.55 (hexane:ethyl acetate=4:1, v/v)

$^1$H NMR (500 MHz, $CDCl_3$) δ 7.77 (s, 1H), 7.50-7.46 (m, 2H), 4.76 (s, 2H), 1.40 (s, 9H)

<Example 27> Preparation of 6-(((5-(tert-butyl)benzo[d]oxazol-2-yl)methyl)thio)-1-phenyl-1,5-dihydro-4H-pyrazolo[3,4-d]pyrimidin-4-one

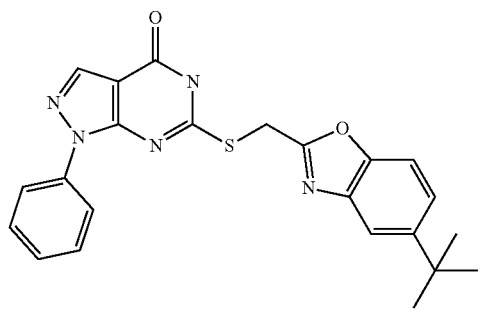 [SMILES: CC(C)(C)c1ccc2oc(CSc3nc4c(cnn4-c4ccccc4)c(=O)[nH]3)nc2c1]

20 mg of 1-phenyl-6-thioxo-1,5,6,7-tetrahydro-4H-pyrazolo[3,4-d]pyridin-4-one (0.08 mmol) obtained in Preparation Example 17 was dissolved in 3 ml of methanol, and 20 mg of 5-(tert-butyl)-2-(chloromethyl)benzo[d]oxazole (0.09 mmol) obtained in Preparation Example 19 above and 0.05 ml of 2N sodium hydroxide were added, followed by stirring under reflux for 12 hours. After completion of the reaction, the reaction solution was concentrated under reduced pressure and purified by column chromatography (hexane:ethyl acetate=10:1, v/v) to give 36 mg of the title compound (0.08 mmol) in 100% yield.

Rf=0.3 (dichloromethane:methanol=20:1, v/v)

$^1$H NMR (500 MHz, DMSO-$d_6$) δ 8.17 (s, 1H), 7.98 (d, J=8.4 Hz, 2H), 7.66 (s, 1H), 7.57 (d, J=8.6 Hz, 1H), 7.49-7.45 (m, 2H), 7.43-7.41 (d, J=8.6 Hz, 1H), 7.36-7.34 (m, 1H), 4.78 (s, 2H), 1.30 (s, 9H)

<Preparation Example 20> Preparation of 2-(chloromethyl)-6-nitrobenzo[d]oxazole

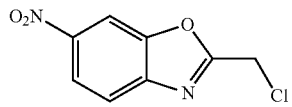 [SMILES: O=[N+]([O-])c1ccc2nc(CCl)oc2c1]

200 mg of 2-amino-5-nitrophenol (1.30 mmol) was dissolved in 5 ml of xylene, and 0.16 ml of chloroacetyl chloride (1.95 mmol) was slowly added, followed by stirring at 0° C. for 2 hours. Thereafter, 0.2 ml of triethylamine (1.43 mmol) was added and the mixture was stirred under reflux for 15 hours. After completion of the reaction, the resultant was extracted with 20 ml of ethyl acetate, washed with 20 ml of an inorganic salt solution, dried over anhydrous sodium sulfate ($Na_2SO_4$), and concentrated under reduced pressure. The residue was purified by column chromatography (hexane:ethyl acetate=10:1, v/v) to give 190 mg of the title compound (0.89 mmol) in 67% yield.

Rf=0.4 (hexane:ethyl acetate=4:1, v/v)

$^1$H NMR (500 MHz, $CDCl_3$) δ 8.47 (s, 1H), 8.33 (d, J=8.8, 1H), 7.87 (d, J=8.8, 1H), 4.82 (s, 2H)

<Example 28> Preparation of 6-(((6-nitrobenzo[d]oxazol-2-yl)methyl)thio)-1-phenyl-1,5-dihydro-4H-pyrazolol[3,4-d]pyrimidin-4-one

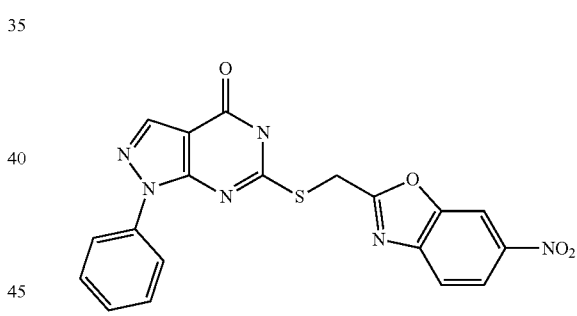

40 mg of 1-phenyl-6-thioxo-1,5,6,7-tetrahydro-4H-pyrazolo[3,4-d]pyridin-4-one (0.16 mmol) obtained in Preparation Example 17 was dissolved in 3 ml of methanol, and 38 mg of 2-(chloromethyl)-6-nitrobenzo[d]oxazole (0.18 mmol) obtained in Preparation Example 20 and 0.1 ml of 2N sodium hydroxide were added, followed by stirring under reflux for 12 hours. After completion of the reaction, the reaction solution was concentrated under reduced pressure and purified by column chromatography (dichloromethane:methanol=100:1, v/v) to give 22 mg of the title compound (0.05 mmol) in 32% yield.

Rf=0.3 (dichloromethane:methanol=20:1, v/v)

$^1$H NMR (500 MHz, DMSO-$d_6$) δ 8.59 (d, J=2.3 Hz, 1H), 8.24 (dd, J=8.8, 2.3 Hz, 1H), 8.20 (s, 1H), 7.91 (d, J=8.8 Hz, 1H), 7.87 (d, J=7.7 Hz, 2H), 7.52-7.45 (m, 2H), 7.39-7.36 (m, 1H), 4.90 (s, 2H)

<Preparation Example 21> Preparation of 2-(chloromethyl)-5-nitrobenzo[d]oxazole

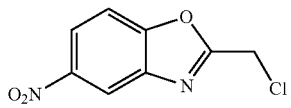

400 mg of 2-amino-4-nitrophenol (2.60 mmol) was dissolved in 5 ml of xylene, and 0.32 ml of chloroacetyl chloride (3.90 mmol) was slowly added, followed by stirring at 0° C. for 2 hours. Thereafter, 0.4 ml of triethylamine (2.86 mmol) was added and the mixture was stirred under reflux for 15 hours. After completion of the reaction, the resultant was extracted with 20 ml of ethyl acetate, washed with 20 ml of an inorganic salt solution, dried over anhydrous sodium sulfate ($Na_2SO_4$), and concentrated under reduced pressure. The residue was purified by column chromatography (hexane:ethyl acetate=10:1, v/v) to give 42 mg of the title compound (0.19 mmol) in 8% yield.

Rf=0.4 (hexane:ethyl acetate=4:1, v/v)

$^1$H NMR (500 MHz, CDCl$_3$) δ 8.66 (d, J=2.2 Hz, 1H), 8.38 (dd, J=9.0, 2.2 Hz, 1H), 7.69 (d, J=9.0 Hz, 1H), 4.80 (s, 2H)

<Example 29> Preparation of 6-(((5-nitrobenzo[d]oxazol-2-yl)methyl)thio)-1-phenyl-1,5-dihydro-4H-pyrazolo[3,4-d]pyrimidin-4-one

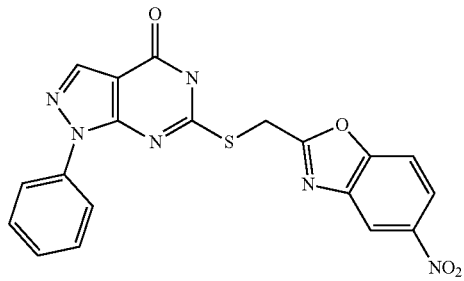 [SMILES: O=c1[nH]c(SCc2nc3cc([N+](=O)[O-])ccc3o2)nc2c1cnn2-c1ccccc1]

40 mg of 1-phenyl-6-thioxo-1,5,6,7-tetrahydro-4H-pyrazolo[3,4-d]pyridin-4-one (0.16 mmol) obtained in Preparation Example 17 was dissolved in 3 ml of methanol, and 37 mg of 2-(chloromethyl)-5-nitrobenzo[d]oxazole (0.17 mmol) obtained in Preparation Example 21 and 0.05 ml of 2N sodium hydroxide were added, followed by stirring under reflux for 12 hours. After completion of the reaction, the reaction solution was concentrated under reduced pressure and purified by column chromatography (dichloromethane:methanol=100:1, v/v) to give 28 mg of the title compound (0.06 mmol) in 41% yield.

Rf=0.3 (dichloromethane:methanol=10:1, v/v)

$^1$H NMR (500 MHz, DMSO-d$_6$) δ 12.96 (s, 1H), 8.58 (d, J=2.3 Hz, 1H), 8.28 (dd, J=9.0, 2.3 Hz, 1H), 8.21 (s, 1H), 7.94 (d, J=9.0 Hz, 1H), 7.90 (d, J=8.1 Hz, 2H), 7.48 (dd, J=7.7, 8.1 Hz, 2H), 7.36 (d, J=7.7 Hz, 1H), 4.90 (s, 2H)

<Preparation Example 22> Preparation of 2-(chloromethyl)-4-nitrobenzo[d]oxazole

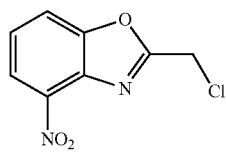

600 mg of 2-amino-3-nitrophenol (3.89 mmol) was dissolved in 10 ml of xylene, 0.66 ml of chloroacetyl chloride (5.83 mmol) was slowly added, followed by stirring at 0° C. for 2 hours. Thereafter, 0.6 ml of triethylamine (4.27 mmol) was added, and the mixture was stirred under reflux for 15 hours. After completion of the reaction, the resultant was extracted with 40 ml of ethyl acetate, washed with 40 ml of an inorganic salt solution, dried over anhydrous sodium sulfate ($Na_2SO_4$), and concentrated under reduced pressure. The residue was purified by column chromatography (hexane:ethyl acetate=10:1, v/v) to give 508 mg of the title compound (2.39 mmol) in 61% yield.

Rf=0.4 (hexane:ethyl acetate=4:1, v/v)

$^1$H NMR (500 MHz, CDCl$_3$) δ 8.27 (d, J=8.2 Hz, 1H), 7.96 (d, J=8.2 Hz, 1H), 7.61 (dd, J=8.2, 8.2 Hz, 1H), 4.90 (s, 2H)

<Example 30> Preparation of 6-(((4-nitrobenzo[d]oxazol-2-yl)methyl)thio)-1-phenyl-1,5-dihydro-4H-pyrazolo[3,4-d]pyrimidin-4-one

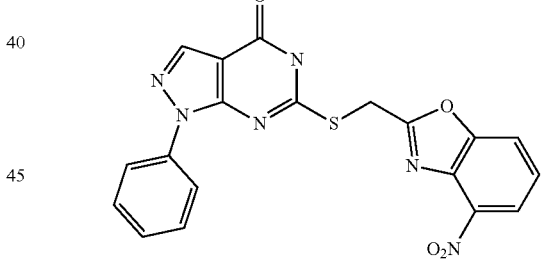

40 mg of 1-phenyl-6-thioxo-1,5,6,7-tetrahydro-4H-pyrazolo[3,4-d]pyridin-4-one (0.16 mmol) obtained in Preparation Example 17 was dissolved in 3 ml of methanol, and 38 mg of 2-(chloromethyl)-4-nitrobenzo[d]oxazole (0.17 mmol) obtained in Preparation Example 22 and 0.05 ml of 2N sodium hydroxide were added, followed by stirring under reflux for 12 hours. After completion of the reaction, the reaction solution was concentrated under reduced pressure and purified by column chromatography (dichloromethane:methanol=100:1, v/v) to give 34 mg of the title compound (0.08 mmol) in 50% yield.

Rf=0.3 (dichloromethane:methanol=10:1, v/v)

$^1$H NMR (500 MHz, DMSO-d$_6$) δ 12.88 (s, 1H), 8.24 (s, 1H), 8.17-8.14 (m, 1H), 8.01-7.96 (m, 3H), 7.60 (d, J=8.2 Hz, 1H), 7.55-7.52 (m, 2H), 7.47 (d, J=8.0 Hz, 1H), 4.13 (s, 2H)

<Preparation Example 23> Preparation of 5-chloro-2-(chloromethyl)-6-nitrobenzo[d]oxazole

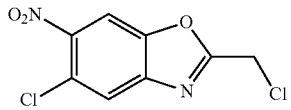 [SMILES: O=[N+]([O-])c1cc2oc(CCl)nc2cc1Cl]

500 mg of 2-amino-4-chloro-5-nitrophenol (2.65 mmol) was dissolved in 8 ml of xylene, and 0.32 ml of chloroacetyl chloride (3.97 mmol) was slowly added, followed by stirring at 0° C. for 2 hours. Thereafter, 0.41 ml of triethylamine (2.91 mmol) was added and the mixture was stirred under reflux for 15 hours. After completion of the reaction, the resultant was extracted with 40 ml of ethyl acetate, washed with 40 ml of an inorganic salt solution, dried over anhydrous sodium sulfate ($Na_2SO_4$), and concentrated under reduced pressure. The residue was purified by column chromatography (hexane:ethyl acetate=10:1, v/v) to give 329 mg of the title compound (1.33 mmol) in 50% yield.

Rf=0.4 (hexane:ethyl acetate=4:1, v/v)

$^1$H NMR (500 MHz, $CDCl_3$) δ 8.15 (s, 1H), 7.94 (s, 1H), 4.80 (s, 2H)

<Example 31> Preparation of 6-(((5-nitro-6-nitrobenzo[d]oxazol-2-yl)methyl)thio)-1-phenyl-1,5-dihydro-4H-pyrazolo[3,4-d]pyrimidin-4-one

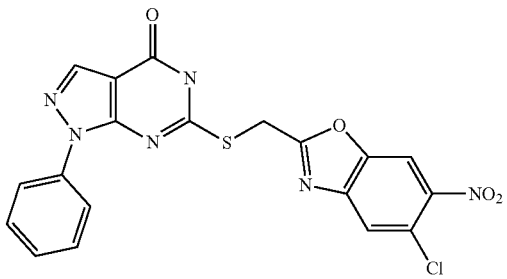 [SMILES: O=c1[nH]c(SCc2nc3cc(Cl)c([N+](=O)[O-])cc3o2)nc2c1cnn2-c1ccccc1]

40 mg of 1-phenyl-6-thioxo-1,5,6,7-tetrahydro-4H-pyrazolo[3,4-d]pyridin-4-one (0.16 mmol) obtained in Preparation Example 17 was dissolved in 3 ml of methanol, and 45 mg of 5-chloro-2-(chloromethyl)-6-nitrobenzo[d]oxazole (0.17 mmol) obtained in Preparation Example 23 and 0.1 ml of 2N sodium hydroxide were added, followed by stirring under reflux for 12 hours. After completion of the reaction, the reaction solution was concentrated under reduced pressure and purified by column chromatography (dichloromethane:methanol=100:1, v/v) to give 22 mg of the title compound (0.05 mmol) in 29% yield.

Rf=0.2 (dichloromethane:methanol=20:1, v/v)

$^1$H NMR (500 MHz, DMSO-$d_6$) δ 10.63 (s, 1H), 8.59 (s, 1H), 8.22 (s, 1H), 8.18 (s, 1H), 7.96-7.93 (m, 1H), 7.86-7.84 (m, 1H), 7.51-7.47 (m, 2H), 7.37 (d, J=7.5 Hz, 1H), 4.90 (s, 2H)

<Preparation Example 24> Preparation of 5,7-dichloro-2-(chloromethyl)-benzo[d]oxazole

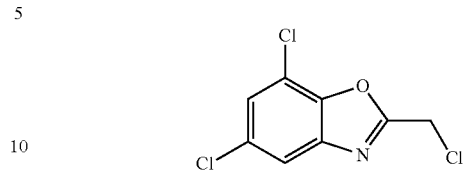

500 mg of 2-amino-4,6-dichlorophenol (2.81 mmol) was dissolved in 10 ml of xylene, and 0.34 ml of chloroacetyl chloride (4.21 mmol) was slowly added, followed by stirring at 0° C. for 2 hours. Thereafter, 0.43 ml of triethylamine (3.09 mmol) was added and stirred under reflux for 15 hours. After completion of the reaction, the resultant was extracted with 40 ml of ethyl acetate, washed with 40 ml of an inorganic salt solution, dried over anhydrous sodium sulfate ($Na_2SO_4$), and concentrated under reduced pressure. The residue was purified by column chromatography (hexane:ethyl acetate=10:1, v/v) to give 470 mg of the title compound (1.99 mmol) in 71% yield.

Rf=0.4 (hexane:ethyl acetate=4:1, v/v)

$^1$H NMR (500 MHz, $CDCl_3$) δ 7.62 (d, J=1.9 Hz, 1H), 7.38 (d, J=1.9 Hz, 1H), 4.77 (s, 2H)

<Example 32> Preparation of 6-(((5,7-dichlorobenzo[d]oxazol-2-yl)methyl)thio)-1-phenyl-1,5-dihydro-4H-pyrazolo[3,4-d]pyrimidin-4-one

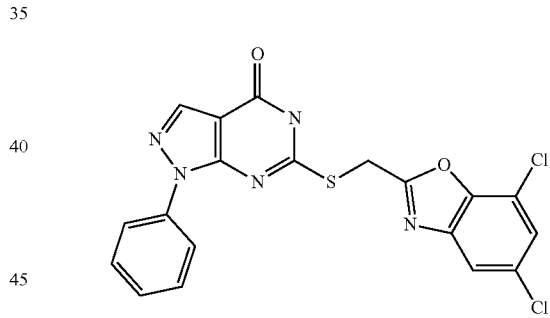

40 mg of 1-phenyl-6-thioxo-1,5,6,7-tetrahydro-4H-pyrazolo[3,4-d]pyridin-4-one (0.16 mmol) obtained in Preparation Example 17 was dissolved in 3 ml of methanol, and 43 mg of 5,7-dichloro-2-(chloromethyl)-benzo[d]oxazole (0.17 mmol) obtained in Preparation Example 24 and 0.1 ml of 2N sodium hydroxide were added, followed by stirring under reflux for 12 hours. After completion of the reaction, the precipitated solid was purified with water, ether, and ethyl acetate to give 11 mg of the title compound (0.02 mmol) in 15% yield.

Rf=0.3 (dichloromethane:methanol=20:1, v/v)

$^1$H NMR (500 MHz, DMSO-$d_6$) δ 8.20 (s, 1H), 7.92 (d, J=7.9 Hz, 2H), 7.86 (d, J=1.9 Hz, 1H), 7.68 (d, J=1.9 Hz, 1H), 7.45 (t, J=7.8 Hz, 2H), 7.34 (t, J=7.3 Hz, 1H), 4.86 (s, 2H)

\<Preparation Example 25\> Preparation of 2-(chloromethyl)-5,7-dimethylbenzo[d]oxazole

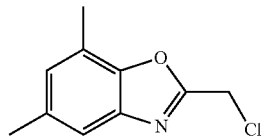

500 mg of 2-amino-4,6-dimethylphenol (3.64 mmol) was dissolved in 10 ml of xylene, and 0.44 ml of chloroacetyl chloride (5.46 mmol) was slowly added, followed by stirring at 0° C. for 2 hours. Thereafter, 0.56 ml of triethylamine (4.00 mmol) was added and stirred under reflux for 15 hours. After completion of the reaction, the resultant was extracted with 40 ml of ethyl acetate, washed with 40 ml of an inorganic salt solution, dried over anhydrous sodium sulfate ($Na_2SO_4$), and concentrated under reduced pressure. The residue was purified by column chromatography (hexane:ethyl acetate=10:1, v/v) to give 479 mg of the title compound (2.45 mmol) in 67% yield.

Rf=0.4 (hexane:ethyl acetate=4:1, v/v)

$^1$H NMR (500 MHz, $CDCl_3$) δ 7.31 (s, 1H), 6.95 (s, 1H), 4.71 (s, 2H), 2.46 (s, 3H), 2.38 (s, 3H)

\<Example 33\> Preparation of 6-(((5,7-dimethylbenzo[d]oxazol-2-yl)methyl)thio)-1-phenyl-1,5-dihydro-4H-pyrazolo[3,4-d]pyrimidin-4-one

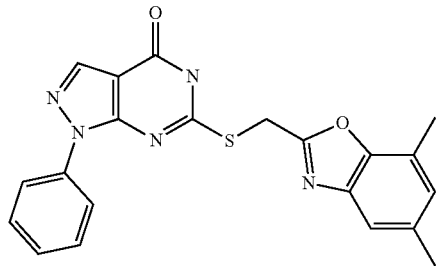 [SMILES: Cc1cc(C)c2oc(CSc3nc4c(cnn4-c4ccccc4)c(=O)[nH]3)nc2c1]

40 mg of 1-phenyl-6-thioxo-1,5,6,7-tetrahydro-4H-pyrazolo[3,4-d]pyrimidin-4-one (0.16 mmol) obtained in Preparation Example 17 was dissolved in 3 ml of methanol, and 35 mg of 2-(chloromethyl)-5,7-dimethylbenzo[d]oxazole (0.17 mmol) obtained in Preparation Example 24 and 0.1 ml of 2N sodium hydroxide were added, followed by stirring under reflux for 12 hours. After completion of the reaction, the reaction solution was concentrated under reduced pressure and purified by column chromatography (dichloromethane:methanol=100:1, v/v) to give 17 mg of the title compound (0.04 mmol) in 26% yield.

Rf=0.3 (dichloromethane:methanol=20:1, v/v)

$^1$H NMR (500 MHz, DMSO-$d_6$) δ 8.24 (s, 1H), 7.99 (d, J=7.9 Hz, 2H), 7.45 (dd, J=7.9, 7.3 Hz, 2H), 7.37 (d, J=7.3 Hz, 1H), 7.30 (s, 1H), 7.00 (s, 1H), 4.80 (s, 2H), 2.38 (s, 3H), 2.34 (s, 3H)

\<Preparation Example 26\> Preparation of 2-(chloromethyl)-5-methoxybenzo[d]oxazole

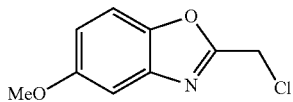 [SMILES: COc1ccc2oc(CCl)nc2c1]

412 mg of 2-amino-4-methoxyphenol (2.96 mmol) was dissolved in 10 ml of xylene, and 0.35 ml of chloroacetyl chloride (4.44 mmol) was slowly added, followed by stirring at 0° C. for 2 hours. Thereafter, 0.45 ml of triethylamine (3.25 mmol) was added, and the mixture was stirred under reflux for 15 hours. After completion of the reaction, the resultant was extracted with 40 ml of ethyl acetate, washed with 40 ml of an inorganic salt solution, dried over anhydrous sodium sulfate ($Na_2SO_4$), and concentrated under reduced pressure. The residue was purified by column chromatography (hexane:ethyl acetate=20:1, v/v) to give 254 mg of the title compound (1.29 mmol) in 43% yield.

Rf=0.4 (hexane:ethyl acetate=4:1, v/v)

$^1$H NMR (500 MHz, $CDCl_3$) δ 7.48-7.38 (m, 1H), 7.21 (d, J=2.6 Hz, 1H), 6.99 (dd, J=9.0, 2.6 Hz, 1H), 4.74 (s, 2H), 3.86 (s, 3H)

\<Example 34\> Preparation of 6-(((5-methoxybenzo[d]oxazol-2-yl)methyl)thio)-1-phenyl-1,5-dihydro-4H-pyrazolo[3,4-d]pyrimidin-4-one

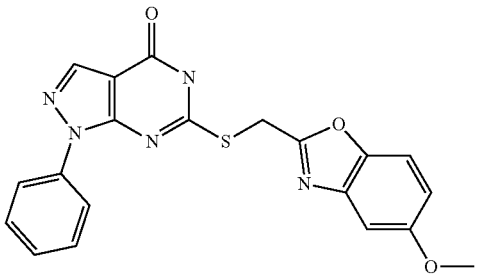 [SMILES: COc1ccc2oc(CSc3nc4c(cnn4-c4ccccc4)c(=O)[nH]3)nc2c1]

40 mg of 1-phenyl-6-thioxo-1,5,6,7-tetrahydro-4H-pyrazolo[3,4-d]pyrimidin-4-one (0.16 mmol) obtained in Preparation Example 17 was dissolved in 3 ml of methanol, and 36 mg of 2-(chloromethyl)-5methoxybenzo[d]oxazole (0.17 mmol) obtained in Preparation Example 25 and 0.1 ml of 2N sodium hydroxide were added, followed by stirring under reflux for 12 hours. After completion of the reaction, the precipitated solid was purified with water, ether, and ethyl acetate to give 15 mg of the title compound (0.04 mmol) in 23% yield.

Rf=0.2 (dichloromethane:methanol=10:1, v/v)

$^1$H NMR (500 MHz, DMSO-$d_6$) δ 12.94 (s, 1H), 8.24 (s, 1H), 7.94 (d, J=7.9 Hz, 2H), 7.59 (d, J=8.9 Hz, 1H), 7.48 (t, J=7.7 Hz, 2H), 7.37 (t, J=7.5 Hz, 1H), 7.25 (d, J=2.5 Hz, 1H), 6.94 (dd, J=8.9, 2.6 Hz, 1H), 4.80 (s, 2H), 3.77 (s, 3H)

<Preparation Example 27> Preparation of 2-(chloromethyl)-6-methoxybenzo[d]oxazole

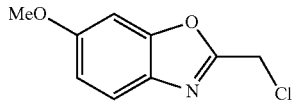

412 mg of 2-amino-5-methoxyphenol (2.96 mmol) was dissolved in 10 ml of xylene, and 0.35 ml of chloroacetyl chloride (4.44 mmol) was slowly added, followed by stirring at 0° C. for 2 hours. Thereafter, 0.45 ml of triethylamine (3.25 mmol) was added, and the mixture was stirred under reflux for 15 hours. After completion of the reaction, the resultant was extracted with 40 ml of ethyl acetate, washed with 40 ml of an inorganic salt solution, dried over anhydrous sodium sulfate ($Na_2SO_4$), and concentrated under reduced pressure. The residue was purified by column chromatography (hexane:ethyl acetate=20:1, v/v) to give 236 mg of the title compound (1.19 mmol) in 40% yield.

Rf=0.4 (hexane:ethyl acetate=4:1, v/v)

$^1$H NMR (500 MHz, $CDCl_3$) δ 7.58 (d, J=8.8 Hz, 1H), 7.03 (d, J=2.4 Hz, 1H), 6.94 (dd, J=8.8, 2.4 Hz, 1H), 4.72 (s, 2H), 3.83 (s, 3H)

<Example 35> Preparation of 6-(((6-methoxybenzo[d]oxazol-2-yl)methyl)thio)-1-phenyl-1,5-dihydro-4H-pyrazolo[3,4-d]pyrimidin-4-one

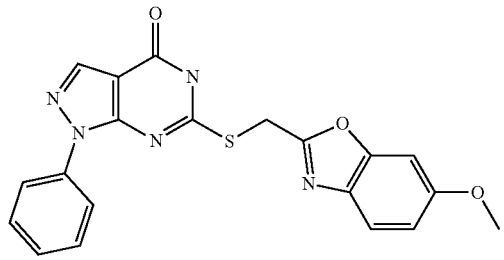 [SMILES: COc1ccc2nc(CSc3nc4c(cnn4-c4ccccc4)c(=O)[nH]3)oc2c1]

40 mg of 1-phenyl-6-thioxo-1,5,6,7-tetrahydro-4H-pyrazolo[3,4-d]pyrimidin-4-one (0.16 mmol) obtained in Preparation Example 17 was dissolved in 3 ml of methanol, and 36 mg of 2-(chloromethyl)-6-methoxybenzo[d]oxazole (0.17 mmol) obtained in Preparation Example 26 and 0.1 ml of 2N sodium hydroxide were added, followed by stirring under reflux for 12 hours. After completion of the reaction, the precipitated solid was purified with water, ether, and ethyl acetate to give 25 mg of the title compound (0.06 mmol) in 38% yield.

Rf=0.2 (dichloromethane:methanol=10:1, v/v)

$^1$H NMR (500 MHz, DMSO-$d_6$) δ 12.93 (s, 1H), 8.24 (s, 1H), 7.97 (d, J=8.0 Hz, 2H), 7.58 (d, J=8.8 Hz, 1H), 7.50 (t, J=7.7 Hz, 2H), 7.38 (t, J=7.4 Hz, 1H), 7.30 (d, J=2.4 Hz, 1H), 6.93 (dd, J=8.8, 2.4 Hz, 1H), 4.79 (s, 2H), 3.79 (s, 3H)

<Preparation Example 28> Preparation of 2-(chloromethyl)-5-(trifluoromethyl)benzo[d]oxazole

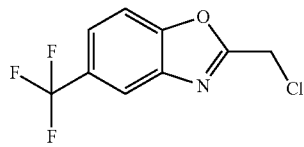 [SMILES: FC(F)(F)c1ccc2oc(CCl)nc2c1]

776 mg of 2-amino-4-(trifluoromethyl)phenol (4.38 mmol) was dissolved in 12 ml of xylene, 0.52 ml of chloroacetyl chloride (6.57 mmol) was slowly added, followed by stirring at 0° C. for 2 hours. Thereafter, 0.67 ml of triethylamine (4.82 mmol) was added and the mixture was stirred under reflux for 15 hours. After completion of the reaction, the resultant was extracted with 40 ml of ethyl acetate, washed with 40 ml of an inorganic salt solution, dried over anhydrous sodium sulfate ($Na_2SO_4$), and concentrated under reduced pressure. The residue was purified by column chromatography (hexane:ethyl acetate=10:1, v/v) to give 275 mg of the title compound (1.17 mmol) in 27% yield.

Rf=0.5 (hexane:ethyl acetate=4:1, v/v)

$^1$H NMR (500 MHz, $CDCl_3$) δ 8.09-8.02 (m, 1H), 7.73-7.64 (m, 2H), 4.81 (s, 2H)

<Example 36> Preparation of 1-phenyl-6-(((5-(trifluoromethyl)benzo[d]oxazol-2-yl)methyl)thio)-1,5-dihydro-4H-pyrazolo[3,4-d]pyrimidin-4-one

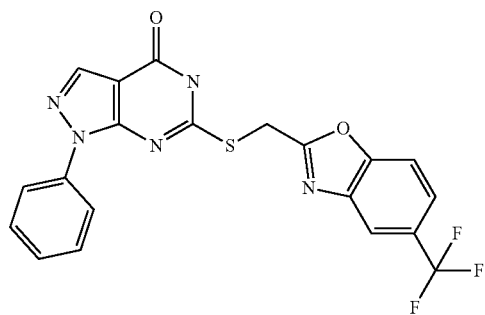 [SMILES: O=c1[nH]c(SCc2nc3cc(C(F)(F)F)ccc3o2)nc2c1cnn2-c1ccccc1]

40 mg of 1-phenyl-6-thioxo-1,5,6,7-tetrahydro-4H-pyrazolo[3,4-d]pyrimidin-4-one (0.16 mmol) obtained in Preparation Example 17 was dissolved in 3 ml of methanol, and 41 mg of 2-(chloromethyl)-5-(trifluoromethyl)benzo[d]oxazole (0.17 mmol) obtained in Preparation Example 27 and 0.1 ml of 2N sodium hydroxide were added, followed by stirring under reflux for 12 hours. After completion of the reaction, the precipitated solid was purified with water, ether, and ethyl acetate to give 25 mg of the title compound (0.06 mmol) in 34% yield.

Rf=0.25 (dichloromethane:methanol=10:1, v/v)

$^1$H NMR (500 MHz, DMSO-$d_6$) δ 12.97 (s, 1H), 8.20 (s, 1H), 8.16-8.12 (m, 1H), 7.96-7.90 (m, 3H), 7.75 (d, J=8.5 Hz, 1H), 7.47 (dd, J=7.7, 8.1 Hz, 2H), 7.35 (dd, J=7.5, 7.7 Hz, 1H), 4.88 (s, 2H)

<Preparation Example 29> Preparation of 1-(4,4-difluorocyclohexyl)-6-thioxo-1,5,6,7-tetrahydro-4H-pyrazolo[3,4-d]pyridin-4-one

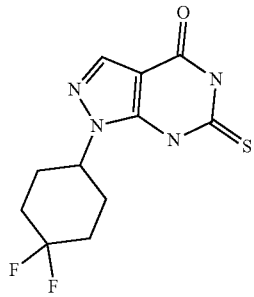 [SMILES: O=c1[nH]c(=S)[nH]c2c1cnn2C1CCC(F)(F)CC1]

Step 1: Preparation of ethyl 5-amino-1-(4,4-difluorocyclohexyl)-1H-pyrazole-4-carboxylate

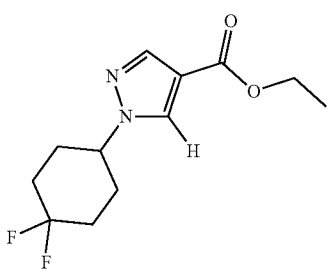 [SMILES: CCOC(=O)c1cnn(C2CCC(F)(F)CC2)c1]

1 g of ethyl (E)-2-cyano-3-ethoxyacrylate (5.91 mmol) was dissolved in 30 ml of ethanol, and 1.32 g of (4,4-difluorocyclohexyl)hydrazine (7.09 mmol) was added, followed by stirring under reflux for 15 hours. After completion of the reaction, the resultant was extracted with 50 ml of ethyl acetate, washed with 50 ml of an inorganic salt solution, dried over anhydrous sodium sulfate ($Na_2SO_4$), and concentrated under reduced pressure. The residue was purified by column chromatography (hexane:ethyl acetate=3:1, v/v) to give 1.16 g of the title compound (4.31 mmol) in 73% yield.

Rf=0.40 (hexane:ethyl acetate=3:1, v/v)

$^1$H NMR (500 MHz, $CDCl_3$) δ 7.65 (s, 1H), 5.03 (br s, 2H), 429 (q, J=8.0 Hz, 2H), 3.95-3.90 (m, 1H), 2.34-2.27 (m, 4H), 2.08-1.84 (m, 4H), 1.36 (t, J=8.0 Hz, 4H)

Step 2: Preparation of ethyl 5-(3-benzoylthioureido)-1-(4,4-difluorocyclohexyl)-1H-pyrazole-4-carboxylate 200 mg of ethyl 5-amino-1-(4,4-difluorocyclohexyl)-1H-pyrazole-4-carboxylate (0.73 mmol) obtained in Step 1 was dissolved in 5 ml of tetrahydrofuran and 0.12 ml of benzoyl isothiocyanate (0.87 mmol) was added, followed by stirring under reflux for 2 hours. After completion of the reaction, the reaction solution was concentrated under reduced pressure and purified by column chromatography (hexane:ethyl acetate=2:1, v/v) to give 312 mg of the title compound (0.72 mmol) in 98% yield.

Rf=0.55 (hexane:ethyl acetate=2:1, v/v)

$^1$H NMR (500 MHz, $CDCl_3$) δ 12.17 (s, 1H), 9.44 (s, 1H), 8.01 (s, 1H), 7.97 (d, J=7.8 Hz, 2H), 7.73 (dd, J=7.8 Hz, 7.8 Hz, 1H), 7.61 (dd, J=7.8 Hz, 7.8 Hz, 2H), 4.29 (q, J=7.3 Hz, 2H), 2.42-2.26 (m, 4H), 2.16-2.10 (m, 2H), 1.91-1.80 (m, 2H), 1.30 (t, J=7.3 Hz, 3H)

Step 3: Preparation of 1-(4,4-difluorocyclohexyl)-6-thioxo-1,5,6,7-tetrahydro-4H-pyrazolo[3,4-d]pyridin-4-one 100 mg of ethyl 5-(3-benzoylthioureido)-1-(4,4-difluorocyclohexyl)-1H-pyrazole-4-carboxylate (0.23 mmol) obtained in Step 2 was dissolved in 3 ml of ethanol, and 44 mg of sodium tertbutoxide (0.46 mmol) was added, followed by stirring at room temperature for 3 hours. After completion of the reaction, it was neutralized with 1N hydrochloric acid to precipitate a solid, which was purified with water, ether, and ethyl acetate to give 50 mg of the title compound (0.17 mmol) in 76% yield.

$^1$H NMR (500 MHz, DMSO-$d_6$) δ 13.44 (br s, 1H), 12.19 (br s, 1H), 7.96 (s, 1H), 4.77 (s, 1H), 2.37-1.81 (m, 8H)

<Example 37> Preparation of 1-(4,4-difluorocyclohexyl)-6-(((6-nitrobenzo[d]oxazol-2-yl)methyl)thio)-1,5-dihydro-4H-pyrazolo[3,4-d]pyrimidin-4-one

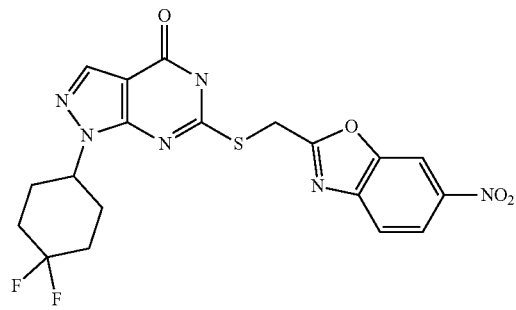 [SMILES: O=c1[nH]c(SCc2nc3ccc([N+](=O)[O-])cc3o2)nc2c1cnn2C1CCC(F)(F)CC1]

40 mg of 1-(4,4-difluorocyclohexyl)-6-thioxo-1,5,6,7-tetrahydro-4H-pyrazolo[3,4-d]pyridin-4-one (0.14 mmol) obtained in Preparation Example 29 above was dissolved in 3 ml of methanol, and 33 mg of 2-(chloromethyl)-6-nitrobenzo[d]oxazole (0.15 mmol) obtained in Preparation Example 20 above and 0.08 ml of 2N sodium hydroxide were added, followed by stirring under reflux for 12 hours. After completion of the reaction, the precipitated solid was purified with water, ether, and ethyl acetate to give 48 mg of the title compound (0.10 mmol) in 75% yield.

Rf=0.30 (dichloromethane:methanol=20:1, v/v)

$^1$H NMR (500 MHz, DMSO-$d_6$) δ 8.71 (d, J=2.3 Hz, 1H), 8.29 (dd, J=8.8, 2.3 Hz, 1H), 7.95 (s, 1H), 7.93 (d, J=8.8 Hz, 1H), 4.90 (s, 2H), 4.54-4.49 (m, 1H), 2.09-1.89 (m, 6H), 1.78-1.68 (in, 2H)

<Example 38> Preparation of 1-(4,4-difluorocyclohexyl)-6-(((5-nitrobenzo[d]oxazol-2-yl)methyl)thio)-1,5-dihydro-4H-pyrazolo[3,4-d]pyrimidin-4-one

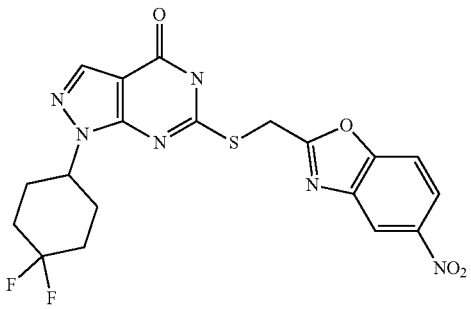 [SMILES: O=c1[nH]c(SCc2nc3cc([N+](=O)[O-])ccc3o2)nc2c1cnn2C1CCC(F)(F)CC1]

24 mg of 1-(4,4-difluorocyclohexyl)-6-thioxo-1,5,6,7-tetrahydro-4H-pyrazolo[3,4-d]pyridin-4-one (0.08 mmol) obtained in Preparation Example 29 above was dissolved in 3 ml of methanol, and 20 mg of 2-(chloromethyl)-5-nitrobenzo[d]oxazole (0.09 mmol) obtained in Preparation Example 21 above and 0.05 ml 2N sodium hydroxide were added, followed by stirring under reflux for 12 hours. After completion of the reaction, the precipitated solid was purified with water, ether, and ethyl acetate to give 41 mg of the title compound (0.09 mmol) in 63% yield.

Rf=0.20 (dichloromethane:methanol=10:1, v/v)

$^1$H NMR (500 MHz, DMSO-$d_6$) δ 12.69 (s, 1H), 8.60 (d, J=2.3 Hz, 1H), 8.32 (dd, J=8.9, 2.3 Hz, 1H), 8.00 (d, J=9.0 Hz, 1H), 7.95 (s, 1H), 4.90 (s, 2H), 4.55 (s, 1H), 2.10-1.90 (m, 6H), 1.79-1.71 (m, 2H)

<Example 39> Preparation of 1-(4,4-difluorocyclohexyl)-6-(((4-nitrobenzo[d]oxazol-2-yl)methyl)thio)-1,5-dihydro-4H-pyrazolo[3,4-d]pyrimidin-4-one

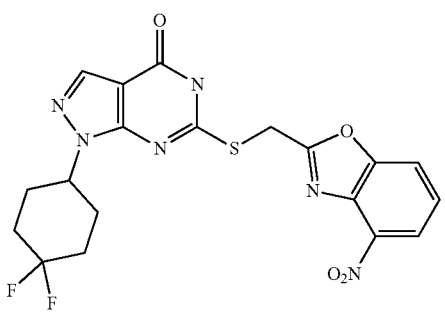 [SMILES: O=c1[nH]c(SCc2nc3c([N+](=O)[O-])cccc3o2)nc2c1cnn2C1CCC(F)(F)CC1]

40 mg of 1-(4,4-difluorocyclohexyl)-6-thioxo-1,5,6,7-tetrahydro-4H-pyrazolo[3,4-d]pyridine-4-one obtained in Preparation Example 29 above (0.14 mmol) was dissolved in 3 ml of methanol, and 33 mg of 2-(chloromethyl)-4-nitrobenzo[d]oxazole (0.15 mmol) obtained in Preparation Example 22 above and 0.08 ml of 2N sodium hydroxide were added, followed by stirring under reflux for 12 hours. After completion of the reaction, the precipitated solid was purified with water, ether, and ethyl acetate to give 13 mg of the title compound (0.03 mmol) in 21% yield.

Rf=0.20 (dichloromethane:methanol=10:1, v/v)

$^1$H NMR (500 MHz, DMSO-$d_6$) δ 12.54 (s, 1H), 7.98 (s, 1H), 7.35-7.16 (m, 3H), 4.93-4.81 (m, 1H), 4.18 (s, 2H), 2.12-1.96 (m, 5H), 1.95-1.83 (m, 3H)

<Example 40> Preparation of 6-(((5-chloro-6-nitrobenzo[d]oxazol-2-yl)methyl)thio)-1-(4,4-difluorocyclohexyl)-1,5-dihydro-4H-pyrazolo[3,4-d]pyrimidin-4-one

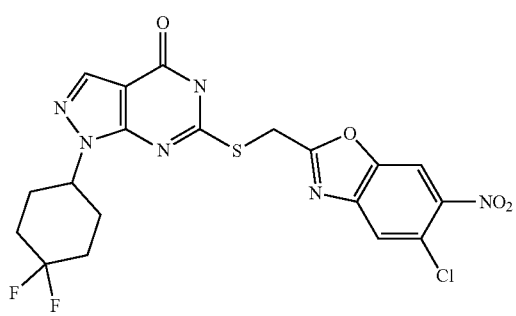 [SMILES: O=c1[nH]c(SCc2nc3cc(Cl)c([N+](=O)[O-])cc3o2)nc2c1cnn2C1CCC(F)(F)CC1]

40 mg of 1-(4,4-difluorocyclohexyl)-6-thioxo-1,5,6,7-tetrahydro-4H-pyrazolo[3,4-d]pyridine-4-one (0.14 mmol) obtained in Preparation Example 29 above was dissolved in 3 ml of methanol, and 38 mg of 5-chloro-2-(chloromethyl)-6-nitrobenzo[d]oxazole (0.15 mmol) obtained in Preparation Example 23 above and 0.08 ml of 2N sodium hydroxide were added, followed by stirring under reflux for 12 hours. After completion of the reaction, the precipitated solid was purified with water, ether, and ethyl acetate to give 70 mg of the title compound (0.14 mmol) in 100% yield.

Rf=0.20 (dichloromethane:methanol=10:1, v/v)

$^1$H NMR (500 MHz, DMSO-$d_6$) δ 8.66 (s, 1H), 8.82 (s, 1H), 7.95 (s, 1H), 4.89 (s, 1H), 4.55-4.47 (m, 1H), 2.29-1.70 (m, 8H)

<Example 41> Preparation of 1-(4,4-difluorocyclohexyl)-6-(((4-methylbenzo[d]oxazol-2-yl)methyl)thio)-1,5-dihydro-4H-pyrazolo[3,4-d]pyrimidin-4-one

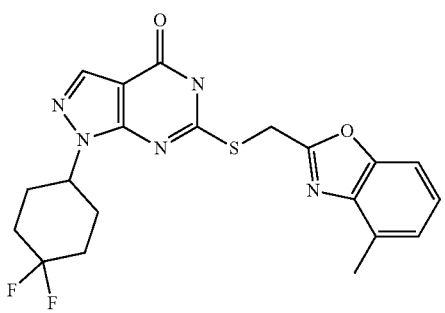 [SMILES: Cc1cccc2oc(CSc3nc4c(cnn4C4CCC(F)(F)CC4)c(=O)[nH]3)nc12]

40 mg of 1-(4,4-difluorocyclohexyl)-6-thioxo-1,5,6,7-tetrahydro-4H-pyrazolo[3,4-d]pyridine-4-one (0.14 mmol) obtained in Preparation Example 29 above was dissolved in 3 ml of methanol, and 28 mg of 2-(chloromethyl)-4-methylbenzo[d]oxazole (0.15 mmol) obtained in Preparation Example 18 and 0.08 ml of 2N sodium hydroxide were added, followed by stirring under reflux for 12 hours. After completion of the reaction, the precipitated solid was purified with water and ethyl acetate to give 39 mg of the title compound (0.09 mmol) in 66% yield.

Rf=0.30 (dichloromethane:methanol=20:1, v/v)

1H NMR (500 MHz, DMSO-d6) δ 7.97 (s, 1H), 7.48 (d, J=8.0 Hz, 1H), 7.27 (dd, J=8.0, 7.6 Hz, 1H), 7.18 (d, J=7.6 Hz, 1H), 4.83 (s, 2H), 4.67-4.54 (m, 1H), 2.49 (s, 3H), 2.18-1.96 (m, 5H), 1.95-1.77 (m, 3H)

<Example 42> Preparation of 6-(((5-(tert-butyl)benzo[d]oxazol-2-yl)methyl)thio)-1-(4,4-difluorocyclohexyl)-1,5-dihydro-4H-pyrazolo[3,4-d]pyrimidin-4-one

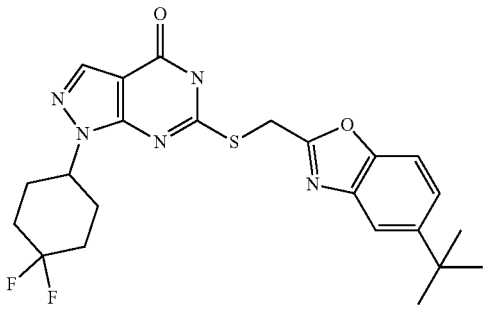 [SMILES: CC(C)(C)c1ccc2oc(CSc3nc4c(cnn4C4CCC(F)(F)CC4)c(=O)[nH]3)nc2c1]

40 mg of 1-(4,4-difluorocyclohexyl)-6-thioxo-1,5,6,7-tetrahydro-4H-pyrazolo[3,4-d]pyridine-4-one (0.14 mmol) obtained in Preparation Example 29 above was dissolved in 3 ml of methanol, and 34 mg of 5-(tert-butyl)-2-(chloromethyl)benzo[d]oxazole (0.15 mmol) obtained in Preparation Example 19 above and 0.08 ml of 2N sodium hydroxide were dissolved, followed by stirring under reflux for 12 hours. After completion of the reaction, the resultant was concentrated under reduced pressure and purified by column chromatography (dichloromethane:methanol=100:1, v/v) to give 64 mg of the title compound (0.13 mmol) in 97% yield.

Rf=0.30 (dichloromethane:methanol=20:1, v/v)

$^1$H NMR (500 MHz, DMSO-d$_6$) δ 12.67 (s, 1H), 7.95 (s, 1H), 7.64 (d, J=2.9 Hz, 1H), 7.59 (d, J=8.6 Hz, 1H), 7.44 (dd, J=8.6, 2.9 Hz, 1H), 4.79 (s, 2H), 4.55-4.50 (m, 1H), 2.09-1.86 (m, 6H), 1.76-1.71 (m, 2H), 1.32 (s, 9H)

<Example 43> Preparation of 6-(((5,7-dichlorobenzo[d]oxazol-2-yl)methyl)thio)-1-(4,4-difluorocyclohexyl)-1,5-dihydro-4H-pyrazolo[3,4-d]pyrimidin-4-one

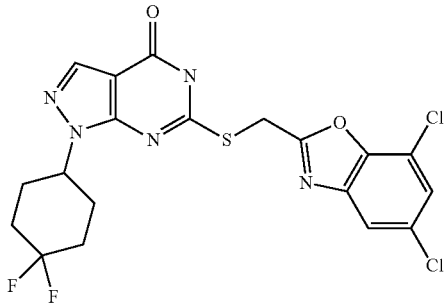 [SMILES: O=c1[nH]c(SCc2nc3cc(Cl)cc(Cl)c3o2)nc2c1cnn2C1CCC(F)(F)CC1]

40 mg of 1-(4,4-difluorocyclohexyl)-6-thioxo-1,5,6,7-tetrahydro-4H-pyrazolo[3,4-d]pyridine-4-one (0.14 mmol) obtained in Preparation Example 29 above was dissolved in 3 ml of methanol, and 36 mg of 5,7-dichloro-2-(chloromethyl)benzo[d]oxazole (0.15 mmol) obtained in Preparation Example 24 above and 0.08 ml of 2N sodium hydroxide were added, followed by stirring under reflux for 12 hours. After completion of the reaction, the precipitated solid was purified with water and ethyl acetate to give 17 mg of the title compound (0.03 mmol) in 25% yield.

Rf=0.20 (dichloromethane:methanol=10:1, v/v)

$^1$H NMR (500 MHz, DMSO-d$_6$) δ 7.94 (s, 1H), 7.85 (d, J=1.9 Hz, 1H), 7.69 (d, J=1.9 Hz, 1H), 4.85 (s, 2H), 4.55-4.50 (m, 1H), 2.12-1.74 (m, 8H)

<Example 44> Preparation of 1-(4,4-difluorocyclohexyl)-6-(((5,7-dimethylbenzo[d]oxazol-2-yl)methyl)thio)-1,5-dihydro-4H-pyrazolo[3,4-d]pyrimidin-4-one

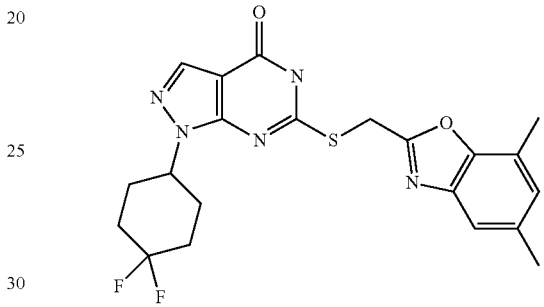

40 mg of 1-(4,4-difluorocyclohexyl)-6-thioxo-1,5,6,7-tetrahydro-4H-pyrazolo[3,4-d]pyridine-4-one (0.14 mmol) obtained in Preparation Example 29 above was dissolved in 3 ml of methanol, and 30 mg of 5,7-dimethyl-2-(chloromethyl)benzo[d]oxazole (0.15 mmol) obtained in Preparation Example 25 above and 0.08 ml of 2N sodium hydroxide were added, followed by stirring under reflux for 12 hours. After completion of the reaction, the precipitated solid was purified with water and ethyl acetate to give 22 mg of the title compound (0.05 mmol) in 36% yield.

Rf=0.20 (dichloromethane:methanol=10:1, v/v)

$^1$H NMR (500 MHz, DMSO-d$_6$) δ 7.95 (s, 1H), 7.27 (s, 1H), 7.02 (s, 1H), 4.79 (s, 2H), 4.59 (s, 1H), 2.38 (d, J=19.4 Hz, 5H), 2.04 (q, J=10.9, 9.9 Hz, 4H), 1.91 (d, J=8.3 Hz, 2H), 1.79 (d, J=11.3 Hz, 2H)

<Example 45> Preparation of 1-(4,4-difluorocyclohexyl)-6-(((5-methoxybenzo[d]oxazol-2-yl)methyl)thio)-1,5-dihydro-4H-pyrazolo[3,4-d]pyrimidin-4-one

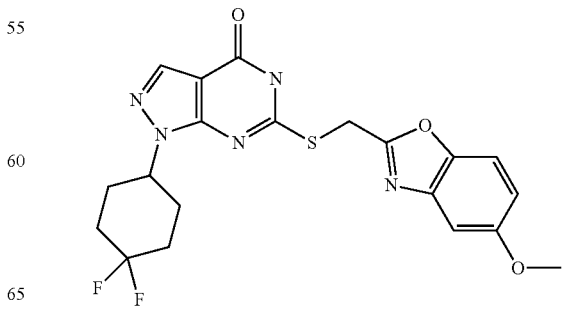

40 mg of 1-(4,4-difluorocyclohexyl)-6-thioxo-1,5,6,7-tetrahydro-4H-pyrazolo[3,4-d]pyridine-4-one (0.14 mmol) obtained in Preparation Example 29 above was dissolved in 3 ml of methanol, and 30 mg of 5-methoxy-2-(chloromethyl)benzo[d]oxazole (0.15 mmol) obtained in Preparation Example 26 above and 0.08 ml of 2N sodium hydroxide were added, followed by stirring under reflux for 12 hours. After completion of the reaction, the precipitated solid was purified with water and ethyl acetate to give 43 mg of the title compound (0.09 mmol) in 70% yield.

Rf=0.20 (dichloromethane:methanol=10:1, v/v)

¹H NMR (500 MHz, DMSO-d₆) δ 12.67 (s, 1H), 7.96 (s, 1H), 7.59 (d, J=8.9 Hz, 1H), 7.23 (d, J=2.5 Hz, 1H), 6.96 (dd, J=8.9, 2.6 Hz, 1H), 4.80 (s, 2H), 4.63-4.48 (m, 1H), 3.78 (s, 3H), 2.14-1.87 (m, 6H), 1.81-1.74 (m, 2H)

<Example 46> Preparation of 1-(4,4-difluorocyclohexyl)-6-(((6-methoxybenzo[d]oxazol-2-yl)methyl)thio)-1,5-dihydro-4H-pyrazolo[3,4-d]pyrimidin-4-one

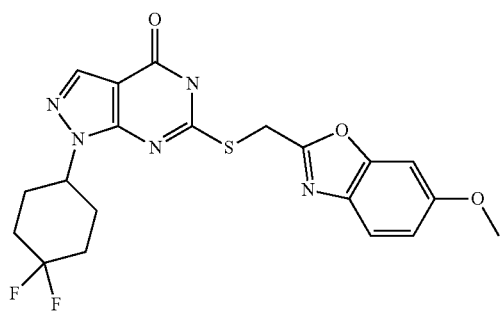 [SMILES: COc1ccc2nc(CSc3nc4c(cnn4C4CCC(F)(F)CC4)c(=O)[nH]3)oc2c1]

40 mg of 1-(4,4-difluorocyclohexyl)-6-thioxo-1,5,6,7-tetrahydro-4H-pyrazolo[3,4-d]pyridin-4-one (0.14 mmol) obtained in Preparation Example 29 above was dissolved in 3 ml of methanol, and 30 mg of 6-methoxy-2-(chloromethyl)benzo[d]oxazole (0.15 mmol) obtained in Preparation Example 27 and 0.08 ml of 2N sodium hydroxide were added, followed by stirring under reflux for 12 hours. After completion of the reaction, the precipitated solid was purified with water and ethyl acetate to give 23 mg of the title compound (0.05 mmol) in a 37% yield.

Rf=0.20 (dichloromethane:methanol=10:1, v/v)

¹H NMR (500 MHz, DMSO-d₆) δ 12.66 (s, 1H), 7.97 (s, 1H), 7.56 (d, J=8.7 Hz, 1H), 7.34 (d, J=2.4 Hz, 1H), 6.95 (dd, J=8.7, 2.4 Hz, 1H), 4.79 (s, 2H), 4.60 (s, 1H), 3.80 (s, 3H), δ 2.16-1.88 (m, 6H), 1.86-1.73 (m, 2H)

<Example 47> Preparation of 1-(4,4-difluorocyclohexyl)-6-(((5-(trifluoromethyl)benzo[d]oxazol-2-yl)methyl)thio)-1,5-dihydro-4H-pyrazolo[3,4-d]pyrimidin-4-one

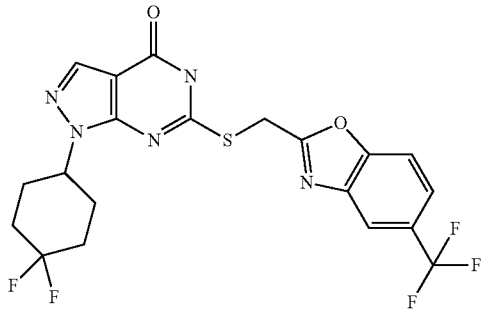 [SMILES: O=c1[nH]c(SCc2nc3cc(C(F)(F)F)ccc3o2)nc2c1cnn2C1CCC(F)(F)CC1]

40 mg of 1-(4,4-difluorocyclohexyl)-6-thioxo-1,5,6,7-tetrahydro-4H-pyrazolo[3,4-d]pyridin-4-one (0.14 mmol) obtained in Preparation Example 29 above was dissolved in 3 ml of methanol, and 36 mg of 5-(trifluoromethyl)-2-(chloromethyl)benzo[d]oxazole (0.15 mmol) obtained in Preparation Example 28 above and 0.08 ml of 2N sodium hydroxide were added, followed by stirring under reflux for 12 hours. After completion of the reaction, the precipitated solid was purified with water and ethyl acetate to give 53 mg of the title compound (0.11 mmol) in 78% yield.

Rf=0.25 (dichloromethane:methanol=10:1, v/v)

¹H NMR (500 MHz, DMSO-d₆) δ 12.71 (s, 1H), 8.15 (s, 1H), 7.97 (d, J=8.7 Hz, 1H), 7.90 (s, 1H), 7.77 (dd, J=8.7, 1.8 Hz, 1H), 4.86 (s, 2H), 4.51 (s, 1H), 2.10-1.93 (m, 6H), 1.76-1.70 (m, 2H)

<Preparation Example 30> Preparation of 1-(tetrahydro-2H-pyran-4-yl)-6-thioxo-1,5,6,7-tetrahydro-4H-pyrazolo[3,4-d]pyridin-4-one

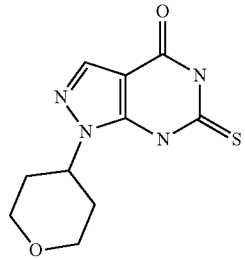 [SMILES: O=c1[nH]c(=S)[nH]c2c1cnn2C1CCOCC1]

Step 1: Preparation of ethyl 5-amino-1-(tetrahydro-2H-pyran-4-yl)-1H-pyrazole-4-carboxylate

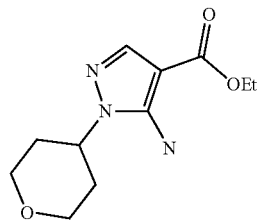 [SMILES: CCOC(=O)c1cnn(C2CCOCC2)c1N]

2.08 g of ethyl (E)-2-cyano-3-ethoxyacrylate (12.3 mmol) was dissolved in 30 ml of ethanol, and 2.25 g of (tetrahydro-2H-pyran-4-yl)hydrazine (14.76 mmol) was added, followed by stirring under reflux for 15 hours. After completion of the reaction, the resultant was extracted with 50 ml of ethyl acetate, washed with 50 ml of an inorganic salt solution, dried over anhydrous sodium sulfate ($Na_2SO_4$), and concentrated under reduced pressure. The residue was purified by column chromatography (hexane:ethyl acetate=1:1, v/v) to give 2.2 g of the title compound (9.22 mmol) in 75% yield.

Rf=0.50 (hexane:ethyl acetate=1:1, v/v)

$^1$H NMR (500 MHz, CDCl$_3$) δ 7.66 (s, 1H), 5.04 (br s, 2H), 4.29 (q, J=7.1 Hz, 2H), 4.19-4.10 (m, 2H), 4.08-3.94 (m, 1H), 3.60-3.45 (m, 2H), 2.40-2.20 (m, 2H), 1.92-1.80 (m, 2H), 1.36 (t, J=7.1 Hz, 3H)

Step 2: Preparation of ethyl 5-(3-benzoylthioureido)-1-(tetrahydro-2H-pyran-4-yl)-1H-pyrazole-4-carboxylate 2.20 g of ethyl 5-amino-1-(tetrahydro-2H-pyran-4-yl)-1H-pyrazole-4-carboxylate (9.22 mmol) obtained in Step 1 was dissolved in 30 ml of tetrahydrofuran, and 1.48 ml of benzoyl isothiocyanate (11.06 mmol) was added, followed by stirring under reflux for 2 hours. After completion of the reaction, the resultant was concentrated under reduced pressure and purified with hexane to give 3.54 g of the title compound (8.74 mmol) in 95% yield.

Rf=0.60 (hexane:ethyl acetate=1:1, v/v)

$^1$H NMR (500 MHz, CDCl$_3$) δ 12.16 (br s, 1H), 9.53 (br s, 1H), 8.02 (s, 1H), 7.98 (d, J=7.4 Hz, 2H), 7.71 (dd, J=7.4 Hz, 7.4 Hz, 1H), 7.60 (dd, J=7.4 Hz, 7.4 Hz, 2H), 4.44-4.34 (m, 1H), 4.28 (q, J=7.1 Hz, 2H), 4.17-4.09 (m, 2H), 3.58-3.50 (m, 2H), 2.37-2.30 (m, 2H), 2.10-2.00 (m, 2H), 1.31 (t, J=7.1 Hz, 3H)

Step 3: Preparation of 1-(tetrahydro-2H-pyran-4-yl)-6-thioxo-1,5,6,7-tetrahydro-4H-pyrazolo[3,4-d]pyridin-4-one 100 mg of ethyl 5-(3-benzoylthioureido)-1-(tetrahydro-2H-pyran-4-yl)-1H-pyrazole-4-carboxylate (0.25 mmol) obtained in Step 2 was dissolved in 3 ml of ethanol, and 0.75 ml of 2N sodium hydroxide (1.50 mmol) was added, followed by stirring under reflux for 30 minutes. After completion of the reaction, it was neutralized with 1N hydrochloric acid to precipitate a solid, which was purified with water and hexane to give 30 mg of the title compound (0.12 mmol) in a yield of 48%.

Rf=0.00 (hexane:ethyl acetate=1:1, v/v)

$^1$H NMR (500 MHz, DMSO-d$_6$) δ 13.48 (br s, 1H), 12.17 (br s, 1H), 7.95 (s, 1H), 4.91-4.82 (m, 1H), 4.08-3.91 (m, 2H), 3.55-3.45 (m, 2H), 2.10-1.90 (m, 2H), 1.90-1.76 (m, 2H)

<Example 48> Preparation of 6-(((6-nitrobenzo[d]oxazol-2-yl)methyl)thio)-1-(tetrahydro-2H-pyran-4-yl)-1,5-dihydro-4H-pyrazolo[3,4-d]pyrimidin-4-one

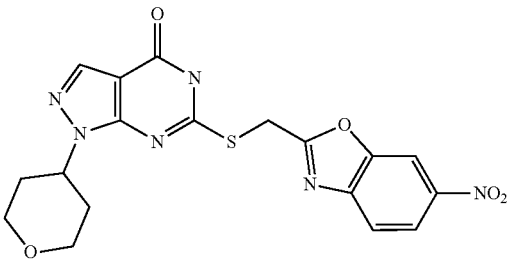 [SMILES: O=c1[nH]c(SCc2nc3ccc([N+](=O)[O-])cc3o2)nc2c1cnn2C1CCOCC1]

40 mg of 1-(tetrahydro-2H-pyran-4-yl)-6-thioxo-1,5,6,7-tetrahydro-4H-pyrazolo[3,4-d]pyridin-4-one (0.15 mmol) obtained in Preparation Example 30 above was dissolved in 3 ml of methanol, and 37 mg of 2-(chloromethyl)-6-nitrobenzo[d]oxazole (0.16 mmol) obtained in Preparation Example 20 above and 0.09 ml of 2N sodium hydroxide were added, followed by stirring under reflux for 12 hours. After completion of the reaction, the precipitated solid was purified with water, ether, and ethyl acetate to give 24 mg of the title compound (0.06 mmol) in 36% yield.

Rf=0.30 (dichloromethane:methanol=20:1, v/v)

$^1$H NMR (500 MHz, DMSO-d$_6$) δ 8.74 (d, J=2.2 Hz, 1H), 8.28 (dd, J=8.8, 2.2 Hz, 1H), 7.95 (s, 1H), 7.92 (s, 1H), 4.88 (s, 2H), 4.52-4.43 (m, 1H), 3.87-3.82 (m, 2H), 3.45-3.36 (m, 2H), 1.95-1.87 (m, 2H), 1.52-1.48 (m, 2H)

<Example 49> Preparation of 6-(((5-nitrobenzo[d]oxazol-2-yl)methyl)thio)-1-(tetrahydro-2H-pyran-4-yl)-1,5-dihydro-4H-pyrazolo[3,4-d]pyrimidin-4-one

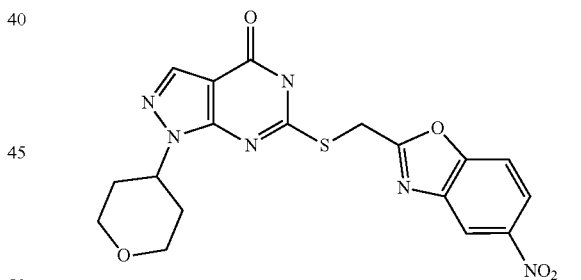

40 mg of 1-(tetrahydro-2H-pyran-4-yl)-6-thioxo-1,5,6,7-tetrahydro-4H-pyrazolo[3,4-d]pyridin-4-one (0.15 mmol) obtained in Preparation Example 30 above was dissolved in 3 ml of methanol, and 37 mg of 2-(chloromethyl)-5-nitrobenzo[d]oxazole (0.16 mmol) obtained in Preparation Example 21 above and 0.09 ml of 2N sodium hydroxide were added, followed by stirring under reflux for 12 hours. After completion of the reaction, the precipitated solid was purified with water, ether, and ethyl acetate to give 41 mg of the title compound (0.09 mmol) in 60% yield.

Rf=0.30 (dichloromethane:methanol=20:1, v/v)

$^1$H NMR (500 MHz, DMSO-d$_6$) δ 12.68 (s, 1H), 8.60 (d, J=2.3 Hz, 1H), 8.31 (dd, J=9.0, 2.3 Hz), 8.00 (d, J=9.0 Hz, 1H), 7.94 (s, 1H), 4.87 (s, 2H), 4.53-4.46 (m, 1H), 3.89-3.82 (m, 2H), 3.42-3.36 (m, 2H), 1.96-1.88 (m, 2H), 1.54-1.50 (m, 2H)

<Example 50> Preparation of 6-(((4-nitrobenzo[d]oxazol-2-yl)methyl)thio)-1-(tetrahydro-2H-pyran-4-yl)-1,5-dihydro-4H-pyrazolo[3,4-d]pyrimidin-4-one

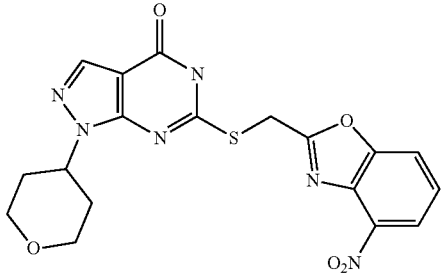 [SMILES: O=c1[nH]c(SCc2nc3c([N+](=O)[O-])cccc3o2)nc2c1cnn2C1CCOCC1]

40 mg of 1-(tetrahydro-2H-pyran-4-yl)-6-thioxo-1,5,6,7-tetrahydro-4H-pyrazolo[3,4-d]pyridin-4-one (0.15 mmol) obtained in Preparation Example 30 above was dissolved in 3 ml of methanol, and 37 mg of 2-(chloromethyl)-4-nitrobenzo[d]oxazole (0.16 mmol) obtained in Preparation Example 22 above and 0.09 ml of 2N sodium hydroxide were added, followed by stirring under reflux for 12 hours. After completion of the reaction, the precipitated solid was purified with water, ether, and ethyl acetate to give 26 mg of the title compound (0.06 mmol) in 39% yield.

Rf=0.30 (dichloromethane:methanol=20:1, v/v)

$^1$H NMR (500 MHz, DMSO-$d_6$) δ 7.97 (s, 1H), 7.29 (dd, J=7.5, 2.2 Hz, 1H), 7.25-7.18 (m, 2H), 4.90-4.84 (m, 1H), 4.18 (s, 2H), 3.90-3.86 (m, 2H), 3.39-3.35 (m, 2H), 2.04-1.96 (m, 2H), 1.77-1.70 (m, 2H)

<Example 51> Preparation of 6-(((5-chloro-6-nitrobenzo[d]oxazol-2-yl)methyl)thio)-1-(tetrahydro-2H-pyran-4-yl)-1,5-dihydro-4H-pyrazolo[3,4-d]pyrimidin-4-one

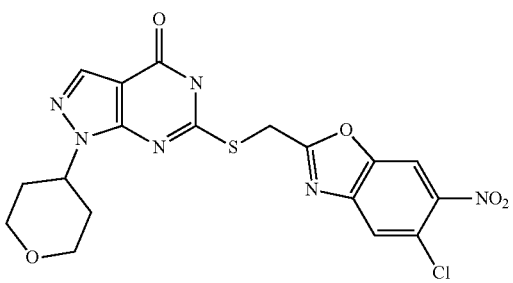 [SMILES: O=c1[nH]c(SCc2nc3cc(Cl)c([N+](=O)[O-])cc3o2)nc2c1cnn2C1CCOCC1]

40 mg of 1-(tetrahydro-2H-pyran-4-yl)-6-thioxo-1,5,6,7-tetrahydro-4H-pyrazolo[3,4-d]pyridin-4-one (0.15 mmol) obtained in Preparation Example 30 above was dissolved in 3 ml of methanol, and 43 mg of 5-chloro-2-(chloromethyl)-6-nitrobenzo[d]oxazole (0.16 mmol) obtained in Preparation Example 23 above and 0.09 ml of 2N sodium hydroxide were added, followed stirring under reflux for 12 hours. After completion of the reaction, the precipitated solid was purified with water, ether, and ethyl acetate to give 20 mg of the title compound (0.04 mmol) in 27% yield.

Rf=0.30 (dichloromethane:methanol=20:1, v/v)

$^1$H NMR (500 MHz, DMSO-$d_6$) δ 8.70 (s, 1H), 8.21 (s, 1H), 7.96 (s, 1H), 4.87 (s, 2H), 4.47-4.40 (m, 1H), 3.89-3.81 (m, 2H), 3.40-3.37 (m, 2H), 1.93-1.86 (m, 2H), 1.53-1.48 (m, 2H)

<Example 52> Preparation of 6-(((4-methylbenzo[d]oxazol-2-yl)methyl)thio)-1-(tetrahydro-2H-pyran-4-yl)-1,5-dihydro-4H-pyrazolo[3,4-d]pyrimidin-4-one

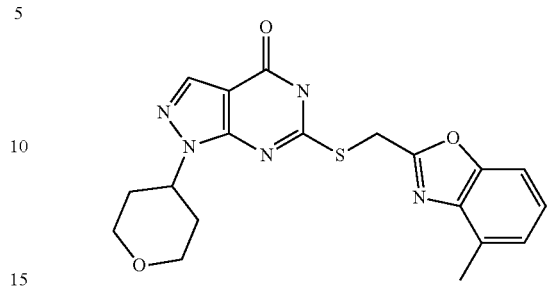

40 mg of 1-(tetrahydro-2H-pyran-4-yl)-6-thioxo-1,5,6,7-tetrahydro-4H-pyrazolo[3,4-d]pyridin-4-one (0.15 mmol) obtained in Preparation Example 30 above was dissolved in 3 ml of methanol, and 32 mg of 2-(chloromethyl)-4-methylbenzo[d]oxazole (0.16 mmol) obtained in Preparation Example 18 and 0.09 ml of 2N sodium hydroxide were added, followed by stirring under reflux for 12 hours. After completion of the reaction, the precipitated solid was purified with water and ethyl acetate to give 14 mg of the title compound (0.03 mmol) in a 22% yield.

Rf=0.30 (dichloromethane:methanol=20:1, v/v)

$^1$H NMR (500 MHz, DMSO-$d_6$) δ 12.58 (br s, 1H), 7.95 (s, 1H), 7.49 (d, J=8.1 Hz, 1H), 7.25 (dd, J=8.1, 7.5 Hz, 1H), 7.16 (d, J=7.5 Hz, 1H), 4.81 (s, 2H), 4.62-4.55 (m, 1H), 3.89 (dd, J=11.0, 4.4 Hz, 2H), 3.41-3.36 (m, 2H), 2.49 (s, 3H), 2.04-1.91 (m, 2H), 1.65-1.61 (m, 2H)

<Example 53> Preparation of 6-(((5-(tert-butyl)benzo[d]oxazol-2-yl)methyl)thio)-1-(tetrahydro-2H-pyran4-yl)-1,5-dihydro-4H-pyrazolo[3,4-d]pyrimidin-4-one

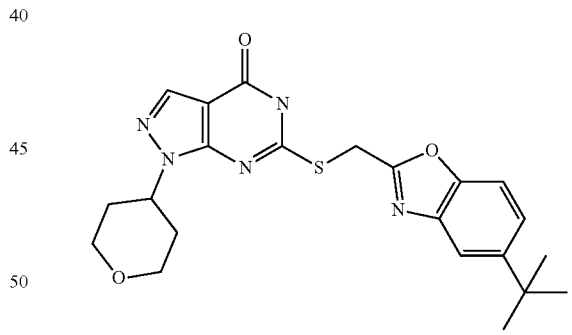

40 mg of 1-(tetrahydro-2H-pyran-4-yl)-6-thioxo-1,5,6,7-tetrahydro-4H-pyrazolo[3,4-d]pyridin-4-one (0.15 mmol) obtained in Preparation Example 30 above was dissolved in 3 ml of methanol, and 39 mg of 5-(tert-butyl)-2-(chloromethyl)benzo[d]oxazole (0.16 mmol) obtained in Preparation Example 19 above and 0.09 ml of 2N sodium hydroxide were added, followed by stirring under reflux for 12 hours. After completion of the reaction, the resultant was concentrated under reduced pressure and purified by column chromatography (dichloromethane:methanol=100:1, v/v) to give 23 mg of the title compound (0.05 mmol) in 33% yield.

Rf=0.30 (dichloromethane:methanol=20:1, v/v)

$^1$H NMR (500 MHz, DMSO-$d_6$) δ 7.94 (s, 1H), 7.64 (d, J=1.9 Hz, 1H), 7.59 (d, J=8.6 Hz, 1H), 7.42 (dd, J=8.7, 2.0

Hz, 1H), 4.77 (s, 2H), 4.55-4.49 (m, 1H), 3.87-3.84 (m, 2H), 3.39-3.35 (m, 2H), 1.99-1.90 (m, 2H), 1.56-1.50 (m, 2H), 1.31 (s, 9H)

<Example 54> Preparation of 6-(((5,7-dichlorobenzo[d]oxazol-2-yl)methyl)thio)-1-(tetrahydro-2H-pyran4-yl)-1,5-dihydro-4H-pyrazolo[3,4-d]pyrimidin-4-one

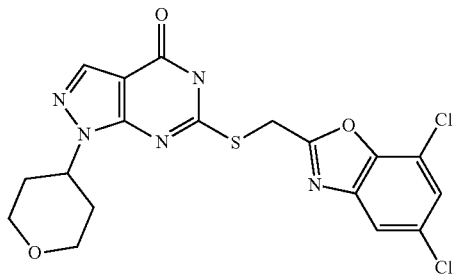 [SMILES: O=c1[nH]c(SCc2nc3cc(Cl)cc(Cl)c3o2)nc2c1cnn2C1CCOCC1]

40 mg of 1-(tetrahydro-2H-pyran-4-yl)-6-thioxo-1,5,6,7-tetrahydro-4H-pyrazolo[3,4-d]pyridin-4-one (0.15 mmol) obtained in Preparation Example 30 above was dissolved in 3 ml of methanol, and 41 mg of 5,7-dichloro-2-(chloromethyl)benzo[d]oxazole (0.16 mmol) obtained in Preparation Example 24 and 0.09 ml of 2N sodium hydroxide were added, followed by stirring under reflux for 12 hours. After completion of the reaction, the precipitated solid was purified with water and ethyl acetate to give 41 mg of the title compound (0.09 mmol) in 57% yield.

Rf=0.30 (dichloromethane:methanol=20:1, v/v)

$^1$H NMR (500 MHz, DMSO-$d_6$) δ 12.67 (br s, 1H), 7.95 (s, 1H), 7.86 (d, J=1.9 Hz, 1H), 7.69 (d, J=1.9 Hz, 1H), 4.85 (s, 2H), 4.54-4.45 (m, 1H), 3.88-3.84 (m, 2H), 3.39-3.34 (m, 2H), 1.98-1.90 (m, 2H), 1.58-1.54 (m, 2H)

<Example 55> Preparation of 6-(((5,7-dimethylbenzo[d]oxazol-2-yl)methyl)thio)-1-(tetrahydro-2H-pyran-4-yl)-1,5-dihydro-4H-pyrazolo[3,4-d]pyrimidin-4-one

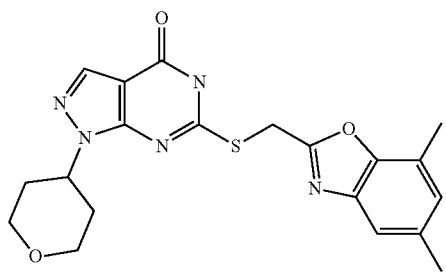 [SMILES: Cc1cc(C)c2oc(CSc3nc4c(cnn4C4CCOCC4)c(=O)[nH]3)nc2c1]

40 mg of 1-(tetrahydro-2H-pyran-4-yl)-6-thioxo-1,5,6,7-tetrahydro-4H-pyrazolo[3,4-d]pyridin-4-one (0.15 mmol) obtained in Preparation Example 30 above was dissolved in 3 ml of methanol, and 34 mg of 5,7-dimethyl-2-(chloromethyl)benzo[d]oxazole (0.16 mmol) obtained in Preparation Example 25 above and 0.09 ml of 2N sodium hydroxide were added, followed by stirring under reflux for 12 hours. After completion of the reaction, the precipitated solid was purified with water and ethyl acetate to give 22 mg of the title compound (0.05 mmol) in 36% yield.

Rf=0.30 (dichloromethane:methanol=20:1, v/v)

$^1$H NMR (500 MHz, DMSO-$d_6$) δ 12.62 (br s, 1H), 7.94 (s, 1H), 7.27 (d, J=1.6 Hz, 1H), 7.00 (s, 1H), 4.78 (s, 2H), 4.61-4.55 (m, 1H), 3.88-3.84 (m, 2H), 3.41-3.35 (m, 2H), 2.41 (s, 3H), 2.35 (s, 3H), 2.00-1.90 (m, 2H), 1.62-1.58 (m, 2H)

<Example 56> Preparation of 6-((((6-methoxybenzo[d]oxazol-2-yl)methyl)thio)-1-(tetrahydro-2H-pyran-4-yl)-1,5-dihydro-4H-pyrazolo[3,4-d]pyrimidin-4-one

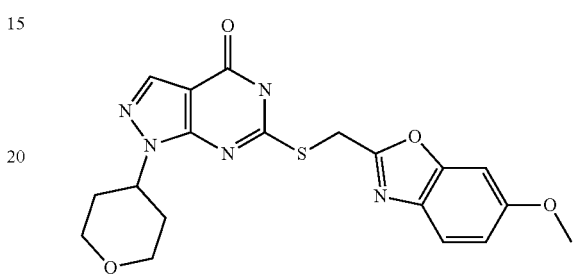

40 mg of 1-(tetrahydro-2H-pyran-4-yl)-6-thioxo-1,5,6,7-tetrahydro-4H-pyrazolo[3,4-d]pyridin-4-one (0.15 mmol) obtained in Preparation Example 30 above was dissolved in 3 ml of methanol, and 35 mg of 6-methoxy-2-(chloromethyl)benzo[d]oxazole (0.16 mmol) obtained in Preparation Example 27 above and 0.09 ml of 2N sodium hydroxide were added, followed by stirring under reflux for 12 hours. After completion of the reaction, the precipitated solid was purified with water and ethyl acetate to give 48 mg of the title compound (0.12 mmol) in 74% yield.

Rf=0.20 (dichloromethane:methanol=10:1, v/v)

$^1$H NMR (500 MHz, DMSO-$d_6$) δ 12.64 (s, 1H), 7.95 (s, 1H), 7.55 (d, J=8.7 Hz, 1H), 7.33 (d, J=2.4 Hz, 1H), 6.94 (dd, J=8.7, 2.4 Hz, 1H), 4.76 (s, 2H), 4.64-4.53 (m, 1H), 3.94-3.86 (m, 2H), 3.79 (s, 3H), 3.46-3.38 (m, 2H), 2.03-1.90 (m, 2H), 1.62-1.55 (m, 2H)

The chemical structural formulas of the compounds prepared in Example 1-56 are summarized and shown in the following table.

TABLE 1

| Example | Chemical Structure |
| --- | --- |
| 1 | 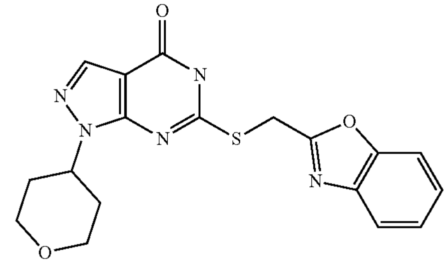 |

TABLE 1-continued
| Example | Chemical Structure |
|---|---|
| 2 | 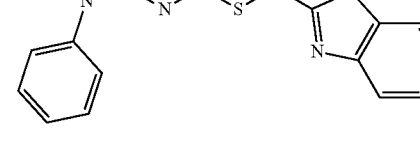 |
| 3 | 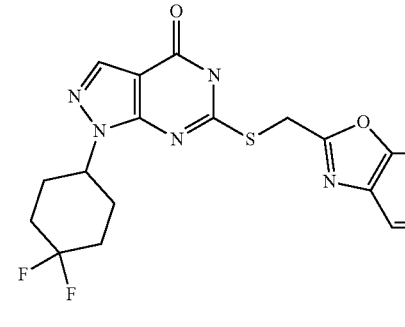 |
| 4 | 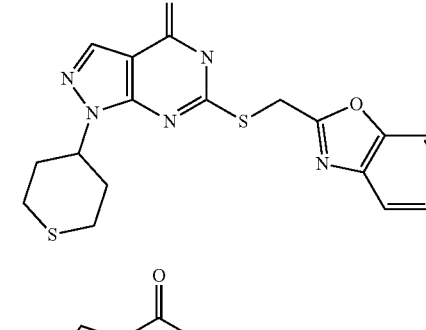 |
| 5 | 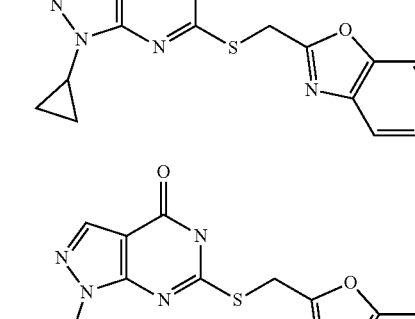 |
| 6 | 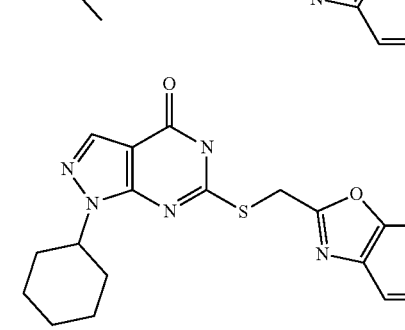 |
| 7 | 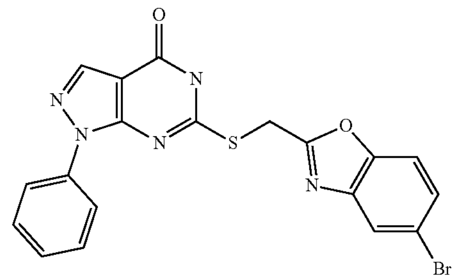 [SMILES: O=c1[nH]c(SCc2nc3cc(Br)ccc3o2)nc2c1cnn2-c1ccccc1] |
| 8 | 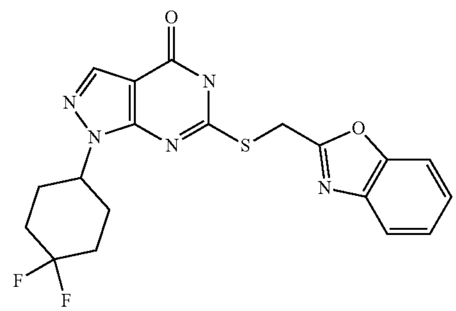 [SMILES: O=c1[nH]c(SCc2nc3ccccc3o2)nc2c1cnn2C1CCC(F)(F)CC1] |
| 9 | 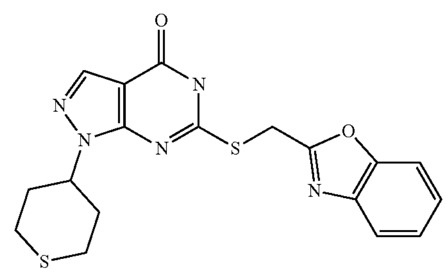 [SMILES: O=c1[nH]c(SCc2nc3ccccc3o2)nc2c1cnn2C1CCSCC1] |
| 10 | 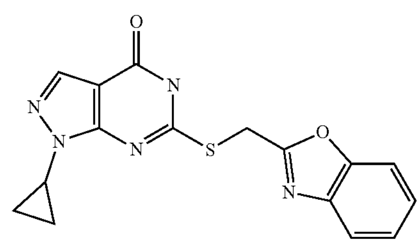 [SMILES: O=c1[nH]c(SCc2nc3ccccc3o2)nc2c1cnn2C1CC1] |
| 11 | 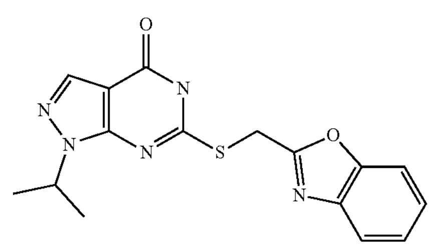 [SMILES: CC(C)n1ncc2c(=O)[nH]c(SCc3nc4ccccc4o3)nc21] |
| 12 | 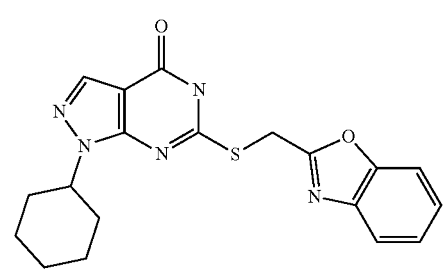 [SMILES: O=c1[nH]c(SCc2nc3ccccc3o2)nc2c1cnn2C1CCCCC1] |

TABLE 1-continued
| Example | Chemical Structure |
|---|---|
| 13 | 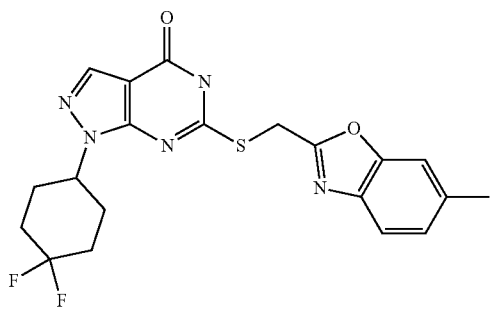 [SMILES: Cc1ccc2nc(CSc3nc4c(cnn4C4CCC(F)(F)CC4)c(=O)[nH]3)oc2c1] |
| 14 | 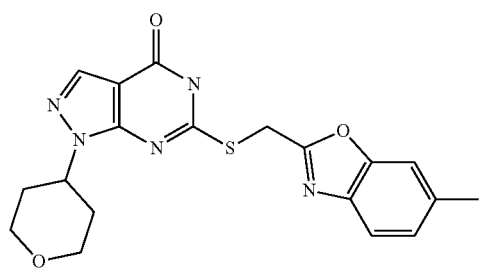 [SMILES: Cc1ccc2nc(CSc3nc4c(cnn4C4CCOCC4)c(=O)[nH]3)oc2c1] |
| 15 | 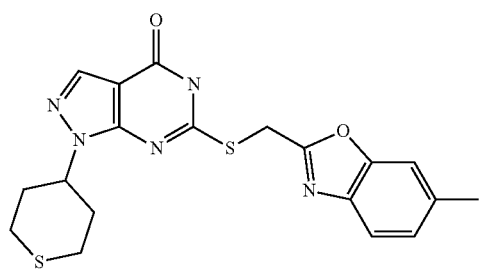 |
| 16 | 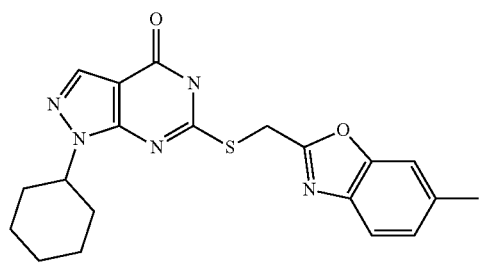 [SMILES: Cc1ccc2nc(CSc3nc4c(cnn4C4CCCCC4)c(=O)[nH]3)oc2c1] |
| 17 | 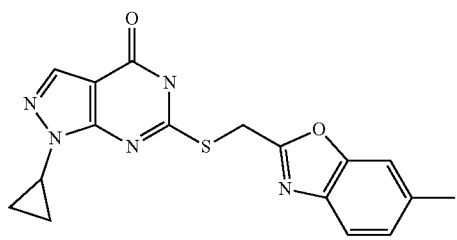 [SMILES: Cc1ccc2nc(CSc3nc4c(cnn4C4CC4)c(=O)[nH]3)oc2c1] |
| 18 | 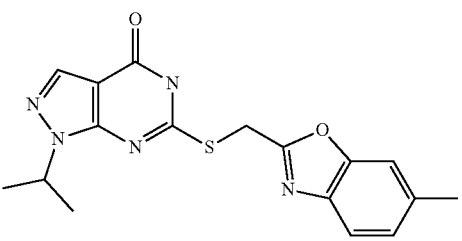 [SMILES: Cc1ccc2nc(CSc3nc4c(cnn4C(C)C)c(=O)[nH]3)oc2c1] |
| 19 | 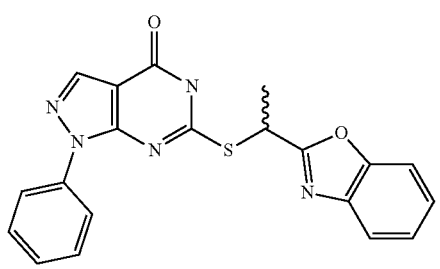 [SMILES: CC(Sc1nc2c(cnn2-c2ccccc2)c(=O)[nH]1)c1nc2ccccc2o1] |
| 20 | 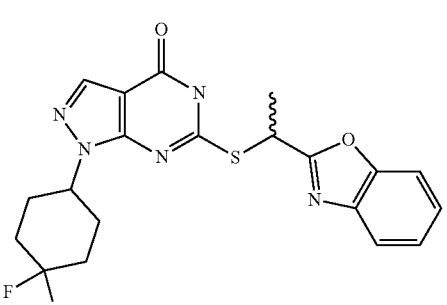 |
| 21 | 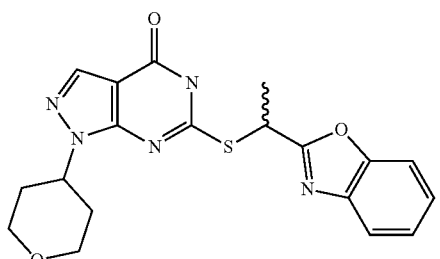 |
| 22 | 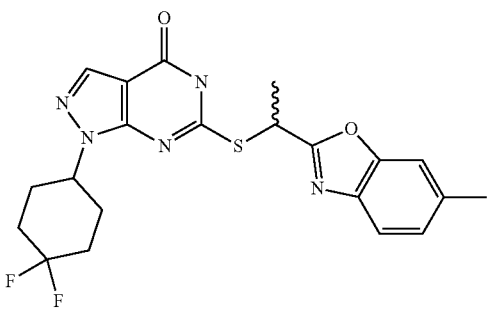 [SMILES: Cc1ccc2nc(C(C)Sc3nc4c(cnn4C4CCC(F)(F)CC4)c(=O)[nH]3)oc2c1] |

TABLE 1-continued

| Example | Chemical Structure |
|---|---|
| 23 | (pyrazolo[3,4-d]pyrimidin-4-one with N-tetrahydropyran, S-CH(–)-6-methylbenzoxazole) |
| 24 | (pyrazolo[3,4-d]pyrimidin-4-one with N-tetrahydrothiopyran, S-CH(–)-6-methylbenzoxazole) |
| 25 | (1-phenyl-pyrazolo[3,4-d]pyrimidin-4-one, S-CH₂-5-phenylbenzoxazole) |
| 26 | (1-phenyl-pyrazolo[3,4-d]pyrimidin-4-one, S-CH₂-4-methylbenzoxazole) |
| 27 | (1-phenyl-pyrazolo[3,4-d]pyrimidin-4-one, S-CH₂-5-tert-butylbenzoxazole) |
| 28 | (1-phenyl-pyrazolo[3,4-d]pyrimidin-4-one, S-CH₂-6-nitrobenzoxazole) |
| 29 | (1-phenyl-pyrazolo[3,4-d]pyrimidin-4-one, S-CH₂-5-nitrobenzoxazole) |
| 30 | (1-phenyl-pyrazolo[3,4-d]pyrimidin-4-one, S-CH₂-4-nitrobenzoxazole) |
| 31 | (1-phenyl-pyrazolo[3,4-d]pyrimidin-4-one, S-CH₂-5-chloro-6-nitrobenzoxazole) |
| 32 | (1-phenyl-pyrazolo[3,4-d]pyrimidin-4-one, S-CH₂-5,7-dichlorobenzoxazole) |

TABLE 1-continued

| Example | Chemical Structure |
|---|---|
| 33 | (structure) |
| 34 | (structure) |
| 35 | (structure) |
| 36 | (structure) |
| 37 | (structure) |"

TABLE 1-continued

| Example | Chemical Structure |
|---|---|
| 38 | (structure) |
| 39 | (structure) |
| 40 | (structure) |
| 41 | (structure) |
| 42 | (structure) |

TABLE 1-continued
| Example | Chemical Structure |
|---|---|
| 43 | 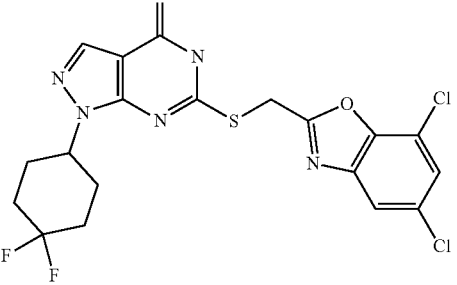 |
| 44 | 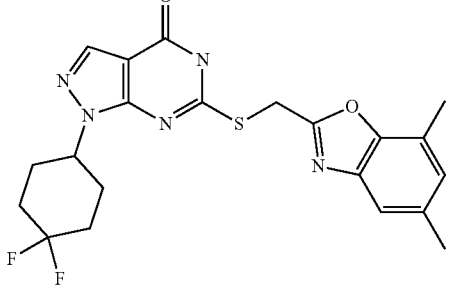 |
| 45 | 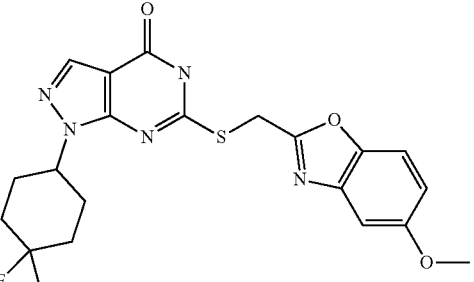 |
| 46 | 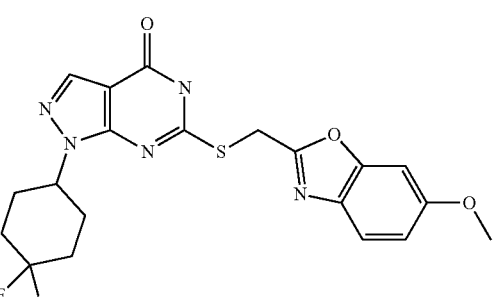 |
| 47 | 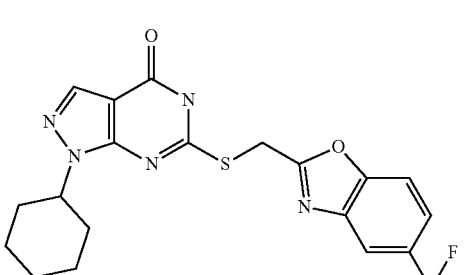 |
| 48 | 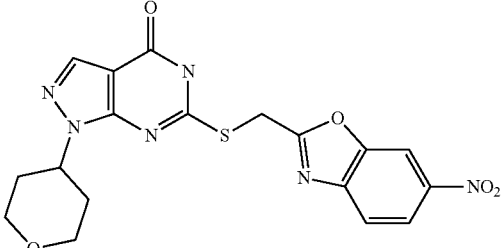 [SMILES: O=c1[nH]c(SCc2nc3ccc([N+](=O)[O-])cc3o2)nc2c1cnn2-c1ccccc1] |
| 49 | 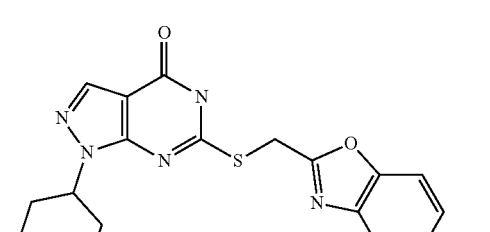 |
| 50 |  |
| 51 |  |
| 52 | 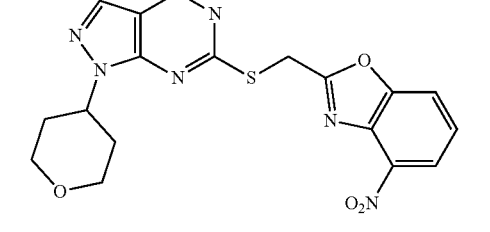 |

TABLE 1-continued

| Example | Chemical Structure |
|---------|-------------------|
| 53 | (pyrazolopyrimidinone with tetrahydropyran, S-CH2-benzoxazole with tert-butyl substituent) |
| 54 | (pyrazolopyrimidinone with tetrahydropyran, S-CH2-benzoxazole with two Cl substituents) |
| 55 | (pyrazolopyrimidinone with tetrahydropyran, S-CH2-benzoxazole with two methyl substituents) |
| 56 | (pyrazolopyrimidinone with tetrahydropyran, S-CH2-benzoxazole with methoxy substituent) |

The inhibitory activity of the representative compounds according to the present invention against phosphodiesterase 9A was tested based on the polarization assay (IMAP-FP screening express kit) provided by MDS (MDS Analytical Technologies, Sunyvale, CA, USA). As a buffer solution, a reaction solution (a reaction solution containing 0.01% Tween 20 provided by MDS was diluted 5 times, then 5 mM DTT is added) and a polarization detection solution (binding solution A and B provided by MDS were mixed at a ratio of 3:1 and IMAP binding reagent 1/600 was added) were prepared. 100 μM of the substrate (Fl-cGMP substrate; MDS) and 3.6 μg/ml of the enzyme PDE9A (ab54113; abcam) were prepared. 3.6 μg/ml PDE9A and 100 μM substrate were diluted to 20 ng/ml (final reaction concentration: 5 ng/ml) and 400 nM (final reaction concentration: 100 nM), respectively. The buffer solution used for all dilution and preparation processes was 1× reaction solution with 1 mM DTT added, and the polarization detection solution was used to induce polarization at the end.

The prepared samples were dispensed on black microplates (Multiwell 384 well plates, #3573, Corning Life Sciences, Lowell, MA, USA) using a 16-channel pipette (multi 16-channel, Finnpipette, Thermo Scientific, Essex, UK). The total reaction volume per well is 20 μl. At this time, 10 μl of 2% DMSO, 5 μl of substrate solution, and 5 μl of reaction solution were used as a negative control, and 10 μl of 2% DMSO, 5 μl of substrate solution, and 5 μl of PDE9A solution were used as a positive control. As the experimental group, 10 μl of the compound prepared in Example, 5 μl of the substrate solution, and 5 μl of the PDE9A solution were used. After pretreatment between the compound and the enzyme was performed for about 10 minutes before the enzyme-substrate reaction, 5 μl of cGMP was added to induce the enzyme reaction. During the reaction, each compound, enzyme, and substrate occupied 50%, 25%, and 25% of the total volume, respectively, and they were prepared at high concentrations of 2, 4, and 4 times, respectively, immediately before addition. After the enzymatic reaction, it was shaken lightly for 1 minute and the enzyme reaction was induced at room temperature for 1 hour. Then, 60 μl of a polarization detection solution prepared in advance was added to induce polarization.

Nanoparticles composed of trivalent metal ions are mixed in the fluorescence detection solution, which combines with phosphoric acid expose by enzymatic reaction to increase the molecular weight and induce polarization. After leaving for 2 hours at room temperature, the polarization (Fluorescence Polarization, FP) value was measured using a multi-label counter (Envision, PerkinElmer, Turku, Finland) (emission wavelength: P-535 nm, S-535 nm, excitation wavelength: 480 nm), and the result was expressed as an $IC_{50}$ value, which is the concentration of the compound that inhibited PDE9A by 50% in vitro (Table 2).

TABLE 2

| Example No. | PDE9A ($IC_{50}$, μM) |
|-------------|----------------------|
| 1  | 0.005 |
| 2  | 0.049 |
| 3  | 0.081 |
| 4  | 0.083 |
| 5  | 0.049 |
| 6  | 0.19 |
| 7  | 0.10 |
| 8  | 0.005 |
| 9  | 0.006 |
| 10 | 0.22 |
| 11 | 0.006 |
| 12 | 0.004 |
| 13 | 0.012 |
| 14 | 0.004 |
| 15 | 0.010 |
| 16 | 0.006 |
| 17 | 0.19 |
| 18 | 0.004 |
| 19 | 0.028 |
| 20 | 0.006 |
| 21 | 0.003 |
| 22 | 0.006 |
| 23 | 0.002 |
| 24 | 0.005 |
| 25 | 10.3% |
| 26 | 0.14 |
| 27 | 6.63 |
| 28 | 51.5% |
| 29 | 2.40 |
| 30 | 1.72 |
| 31 | 38.9% |
| 32 | 27.7% |
| 33 | 0.95 |
| 34 | 0.12 |

TABLE 2-continued

| Example No. | PDE9A (IC$_{50}$, µM) |
| --- | --- |
| 35 | 83.6% |
| 36 | 34.1 |
| 37 | 0.074 |
| 38 | 0.045 |
| 39 | 0.077 |
| 40 | 1.66 |
| 41 | 0.022 |
| 42 | 0.13 |
| 43 | 0.12 |
| 44 | 0.015 |
| 45 | 0.008 |
| 46 | 0.003 |
| 47 | 0.12 |
| 48 | 0.023 |
| 49 | 0.032 |
| 50 | 0.13 |
| 51 | 0.035 |
| 52 | 0.017 |
| 53 | 0.045 |
| 54 | 0.019 |
| 55 | 0.010 |
| 56 | 0.003 |

In Table 2, values expressed as % mean the % inhibition of PDE9A in 10 µM of the compound.

The invention claimed is:

1. A compound represented by the following Chemical formula 1 or a pharmaceutically acceptable salt thereof,

[Chemical Formula 1]

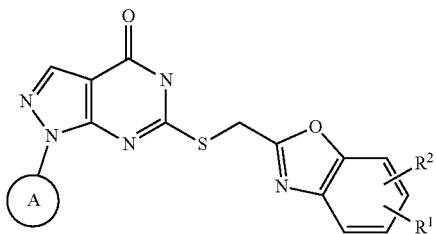

In Chemical Formula 1,

A is phenyl unsubstituted or substituted with one or more halogens, $C_{1-5}$ straight or branched alkyl unsubstituted or substituted with one or more halogens, 3 to 6 membered cycloalkyl unsubstituted or substituted with one or more halogens, or 3 to 6 membered heterocycloalkyl unsubstituted or substituted with one or more halogens, and $R^1$ and $R^2$ are each independently —H, halogen, —NO$_2$, —CF$_3$, phenyl unsubstituted or substituted with one or more halogens, $C_{1-5}$ straight or branched alkyl unsubstituted or substituted with one or more halogens, or $C_{1-5}$ straight or branched alkoxy unsubstituted or substituted with one or more halogens, with a proviso that the compound is not 6-((benzo[d]oxazol-2-ylmethyl)thio)-1-phenyl-1,5-dihydro-4H-pyrazolo[3,4-d]pyrimidin-4-one.

2. The compound or a pharmaceutically acceptable salt thereof according to claim 1, wherein A is phenyl, $C_{1-5}$ straight or branched alkyl unsubstituted or substituted with one or more halogens, or 3 to 6 membered heterocycloalkyl unsubstituted or substituted with one or more halogens, and $R^1$ and $R^2$ are each independently —H, halogen, —NO$_2$, —CF$_3$, phenyl, $C_{1-5}$ straight or branched alkyl unsubstituted or substituted with one or more halogens, or $C_{1-5}$ straight or branched alkoxy unsubstituted or substituted with one or more halogens.

3. The compound or a pharmaceutically acceptable salt thereof according claim 2, wherein A is phenyl,

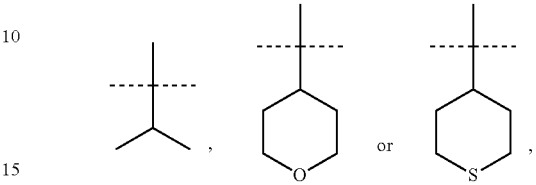

and $R^1$ and $R^2$ are each independently —H, halogen, —NO$_2$, —CF$_3$, —CH$_3$, —C(CH$_3$)$_3$, or phenyl.

4. The compound or a pharmaceutically acceptable salt thereof according to claim 1, wherein the compound is 6-((benzo[d]oxazol-2-ylmethyl)thio)-1-(tetrahydro-2H-pyran-4-yl)-1,5-dihydro-4H-pyrazolo[3,4-d]pyrimidin-4-one, 6-(((5-methylbenzo[d]oxazol-2-yl)methyl)thio)-1-phenyl-1,5-dihydro-4H-pyrazolo[3,4-d]pyrimidin-4-one, 6-(((5-fluorobenzo[d]oxazol-2-yl)methyl)thio)-1-phenyl-1,5-dihydro-4H-pyrazolo[3,4-d]pyrimidin-4-one, 6-(((6-methylbenzo[d]oxazol-2-yl)methyl)thio)-1-phenyl-1,5-dihydro-4H-pyrazolo[3,4-d]pyrimidin-4-one, 6-(((5-chlorobenzo[d]oxazol-2-yl)methyl)thio)-1-phenyl-1,5-dihydro-4H-pyrazolo[3,4-d]pyrimidin-4-one, 6-(((5-bromobenzo[d]oxazol-2-yl)methyl)thio)-1-phenyl-1,5-dihydro-4H-pyrazolo[3,4-d]pyrimidin-4-one, 6-((benzo[d]oxazol-2-ylmethyl)thio)-1-(4,4-difluorocyclohexyl)-1,5-dihydro-4H-pyrazolo[3,4-d]pyrimidin-4-one, 6-((benzo[d]oxazol-2-ylmethyl)thio)-1-(tetrahydro-2H-thiopyran-4-yl)-1,5-dihydro-4H-pyrazolo[3,4-d]pyrimidin-4-one, 6-((benzo[d]oxazol-2-ylmethyl)thio)-1-cyclopropyl-1,5-dihydro-4H-pyrazolo[3,4-d]pyrimidin-4-one, 6-((benzo[d]oxazol-2-ylmethyl)thio)-1-isopropyl-1,5-dihydro-4H-pyrazolo[3,4-d]pyrimidin-4-one, 6-((benzo[d]oxazol-2-ylmethyl)thio)-1-cyclohexyl-1,5-dihydro-4H-pyrazolo[3,4-d]pyrimidin-4-one, 6-(((6-methylbenzo[d]oxazol-2-yl)methyl)thio)-1-(4,4-difluorocyclohexyl)-1,5-dihydro-4H-pyrazolo[3,4-d]pyrimidin-4-one, 6-(((6-methylbenzo[d]oxazol-2-yl)methyl)thio)-1-(tetrahydro-2H-pyran-4-yl)-1,5-dihydro-4H-pyrazolo[3,4-d]pyrimidin-4-one, 6-(((6-methylbenzo[d]oxazol-2-yl)methyl)thio)-1-(tetrahydro-2H-thiopyran-4-yl)-1,5-dihydro-4H-pyrazolo[3,4-d]pyrimidin-4-one, 6-(((6-methylbenzo[d]oxazol-2-yl)methyl)thio)-1-cyclohexyl-1,5-dihydro-4H-pyrazolo[3,4-d]pyrimidin-4-one, 6-(((6-methylbenzo[d]oxazol-2-yl)methyl)thio)-1-cyclopropyl-1,5-dihydro-4H-pyrazolo[3,4-d]pyrimidin-4-one, 6-(((6-methylbenzo[d]oxazol-2-yl)methyl)thio)-1-isopropyl-1,5-dihydro-4H-pyrazolo[3,4-d]pyrimidin-4-one, 6-((1-(benzo[d]oxazol-2-yl)ethyl)thio)-1-phenyl-1,5-dihydro-4H-pyrazolo[3,4-d]pyrimidin-4-one, 6-((1-benzo[d]oxazol-2-yl)ethyl)thio)-1-(4,4-difluorocyclohexyl)-1,5-dihydro-4H-pyrazolo[3,4-d]pyrimidin-4-one, 6-((1-benzo[d]oxazol-2-yl)ethyl)thio)-1-(tetrahydro-2H-pyran-4-yl)-1,5-dihydro-4H-pyrazolo[3,4-d]pyrimidin-4-one, 1-(4,4-difluorocyclohexyl)-6-((1-(6-methylbenzo[d]oxazol-2-yl)ethyl)thio)-1,5-dihydro-4H-pyrazolo[3,4-d]pyrimidin-4-one, 6-((1-(6-methylbenzo[d]oxazol-2-yl)ethyl)thio)-1-(tetrahydro-2H-pyran-4-yl)-1,5-dihydro-4H-pyrazolo[3,4-d]pyrimidin-4-one, 6-((1-(6-methylbenzo[d]oxazol-2-yl)ethyl)thio)-1-(tetrahydro-2H-thiopyran-4-yl)-1,5-dihydro-4H-pyrazolo[3,4-d]pyrimidin-4-one, 1-phenyl-6-(((5-phenylbenzo[d]oxazol-2-yl)methyl)thio)-1,5-dihydro-4H-pyrazolo[3,4-d]pyrimidin-4-one, 6-(((4-methylbenzo[d]oxazol-2-yl)methyl)thio)-1-phenyl-1,5-dihydro-4H-pyrazole[3,4-d]pyrimidin-4-one, 6-(((5-(tert-butyl)benzo[d]oxazol-2-yl)methyl)thio)-1-phenyl-1,5-dihydro-4H-pyrazolo[3,4-d]pyrimidin-4-one, 6-(((6-nitrobenzo[d]oxazol-2-yl)methyl)thio)-1-phenyl-1,5-dihydro-4H-pyrazolo[3,4-d]pyrimidin-4-one, 6-(((5-nitrobenzo[d]oxazol-2-yl)methyl)thio)-1-phenyl-1,5-dihydro-4H-pyrazolo[3,4-d]pyrimidin-4-one, 6-(((4-nitrobenzo[d]oxazol-2-yl)methyl)thio)-1-phenyl-1,5-dihydro-4H-pyrazolo[3,4-d]pyrimidin-4-one, 6-(((5-nitro-6-nitrobenzo[d]oxazol-2-yl)methyl)thio)-1-phenyl-1,5-dihydro-4H-pyrazolo[3,4-d]pyrimidin-4-one, 6-(((5,7-dichlorobenzo[d]oxazol-2-yl)methyl)thio)-1-phenyl-1,5-dihydro-4H-pyrazolo[3,4-d]pyrimidin-4-one, 6-(((5,7-dimethylbenzo[d]oxazol-2-yl)methyl)thio)-1-phenyl-1,5-dihydro-4H-pyrazolo[3,4-d]pyrimidin-4-one, 6-(((5-methoxybenzo[d]oxazol-2-yl)methyl)thio)-1-phenyl-1,5-dihydro-4H-pyrazolo[3,4-d]pyrimidin-4-one, 6-(((6-methoxybenzo[d]oxazol-2-yl)methyl)thio)-1-phenyl-1,5-dihydro-4H-pyrazolo[3,4-d]pyrimidin-4-one, 1-phenyl-6-(((5-(trifluoromethyl)benzo[d]oxazol-2-yl)methyl)thio)-1,5-dihydro-4H-pyrazolo[3,4-d]pyrimidin-4-one, 1-(4,4-difluorocyclohexyl)-6-(((6-nitrobenzo[d]oxazol-2-yl)methyl)thio)-1,5-dihydro-4H-pyrazolo[3,4-d]pyrimidin-4-one, 1-(4,4-difluorocyclohexyl)-6-(((5-nitrobenzo[d]oxazol-2-yl)methyl)thio)-1,5-dihydro-4H-pyrazolo[3,4-d]pyrimidin-4-one, 1-(4,4-difluorocyclohexyl)-6-(((4-nitrobenzo[d]oxazol-2-yl)methyl)thio)-1,5-dihydro-4H-pyrazolo[3,4-d]pyrimidin-4-one, 6-(((5-chloro-6-nitrobenzo[d]oxazol-2-yl)methyl)thio)-1-(4,4-difluorocyclohexyl)-1,5-dihydro-4H-pyrazolo[3,4-d]pyrimidin-4-one, 1-(4,4-difluorocyclohexyl)-6-(((4-methylbenzo[d]oxazol-2-yl)methyl)thio)-1,5-dihydro-4H-pyrazolo[3,4-d]pyrimidin-4-one, 6-(((5-(tert-butyl)benzo[d]oxazol-2-yl)methyl)thio)-1-(4,4-difluorocyclohexyl)-1,5-dihydro-4H-pyrazolo[3,4-d]pyrimidin-4-one, 6-(((5,7-dichlorobenzo[d]oxazol-2-yl)methyl)thio)-1-(4,4-difluorocyclohexyl)-1,5-dihydro-4H-pyrazolo[3,4-d]pyrimidin-4-one, 1-(4,4-difluorocyclohexyl)-6-(((5,7-dimethylbenzo[d]oxazol-2-yl)methyl)thio)-1,5-dihydro-4H-pyrazolo[3,4-d]pyrimidin-4-one, 1-(4,4-difluorocyclohexyl)-6-(((5-methoxybenzo[d]oxazol-2-yl)methyl)thio)-1,5-dihydro-4H-pyrazolo[3,4-d]pyrimidin-4-one, 1-(4,4-difluorocyclohexyl)-6-(((6-methoxybenzo[d]oxazol-2-yl)methyl)thio)-1,5-dihydro-4H-pyrazolo[3,4-d]pyrimidin-4-one, 1-(4,4-difluorocyclohexyl)-6-(((5-(trifluoromethyl)benzo[d]oxazol-2-yl)methyl)thio)-1,5-dihydro-4H-pyrazolo[3,4-d]pyrimidin-4-one, 6-(((6-nitrobenzo[d]oxazol-2-yl)methyl)thio)-1-(tetrahydro-2H-pyran-4-yl)-1,5-dihydro-4H-pyrazolo[3,4-d]pyrimidin-4-one, 6-(((5-nitrobenzo[d]oxazol-2-yl)methyl)thio)-1-(tetrahydro-2H-pyran-4-yl)-1,5-dihydro-4H-pyrazolo[3,4-d]pyrimidin-4-one, 6-(((4-nitrobenzo[d]oxazol-2-yl)methyl)thio)-1-(tetrahydro-2H-pyran-4-yl)-1,5-dihydro-4H-pyrazolo[3,4-d]pyrimidin-4-one, 6-(((5-chloro-6-nitrobenzo[d]oxazol-2-yl)methyl)thio)-1-(tetrahydro-2H-pyran-4-yl)-1,5-dihydro-4H-pyrazolo[3,4-d]pyrimidin-4-one, 6-(((4-methylbenzo[d]oxazol-2-yl)methyl)thio)-1-(tetrahydro-2H-pyran-4-yl)-1,5-dihydro-4H-pyrazolo[3,4-d]pyrimidin-4-one, 6-(((5-(tert-butyl)benzo[d]oxazol-2-yl)methyl)thio)-1-(tetrahydro-2H-pyran4-yl)-1,5-dihydro-4H-pyrazolo[3,4-d]pyrimidin-4-one, 6-(((5,7-dichlorobenzo[d]oxazol-2-yl)methyl)thio)-1-(tetrahydro-2H-pyran4-yl)-1,5-dihydro-4H-pyrazolo[3,4-d]pyrimidin-4-one, 6-(((5,7-dimethylbenzo[d]oxazol-2-yl)methyl)thio)-1-(tetrahydro-2H-pyran-4-yl)-1,5-dihydro-4H-pyrazolo[3,4-d]pyrimidin-4-one, or 6-(((6-methoxybenzo[d]oxazol-2-yl)methyl)thio)-1-(tetrahydro-2H-pyran-4-yl)-1,5-dihydro-4H-pyrazolo[3,4-d]pyrimidin-4-one.

5. A composition comprising the compound or a pharmaceutically acceptable salt thereof according to claim 1, and a pharmaceutically acceptable carrier.

* * * * *